(12) United States Patent
Kikyo et al.

(10) Patent No.: US 9,580,689 B2
(45) Date of Patent: Feb. 28, 2017

(54) INDUCED PLURIPOTENT STEM CELLS

(75) Inventors: Nobuaki Kikyo, Edina, MN (US); Hiroyuki Hirai, Minneapolis, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 520 days.

(21) Appl. No.: 13/811,572

(22) PCT Filed: Jul. 22, 2011

(86) PCT No.: PCT/US2011/044995
§ 371 (c)(1),
(2), (4) Date: Apr. 5, 2013

(87) PCT Pub. No.: WO2012/012708
PCT Pub. Date: Jan. 26, 2012

(65) Prior Publication Data
US 2013/0195812 A1 Aug. 1, 2013

Related U.S. Application Data

(60) Provisional application No. 61/366,821, filed on Jul. 22, 2010, provisional application No. 61/390,454, filed on Oct. 6, 2010.

(51) Int. Cl.
| | |
|---|---|
| *C12N 5/00* | (2006.01) |
| *C12N 5/074* | (2010.01) |
| *C07K 14/47* | (2006.01) |
| *C12N 15/85* | (2006.01) |

(52) U.S. Cl.
CPC ........ *C12N 5/0696* (2013.01); *C07K 14/4702* (2013.01); *C12N 15/8509* (2013.01); *A01K 2207/12* (2013.01); *A01K 2227/105* (2013.01); *C07K 2319/71* (2013.01); *C12N 2501/602* (2013.01); *C12N 2501/603* (2013.01); *C12N 2501/604* (2013.01); *C12N 2501/606* (2013.01); *C12N 2506/1307* (2013.01); *C12N 2510/00* (2013.01); *C12N 2740/15041* (2013.01)

(58) Field of Classification Search
CPC .......................... C12N 5/0696; C12N 15/8509
See application file for complete search history.

(56) References Cited

U.S. PATENT DOCUMENTS

| | | | |
|---|---|---|---|
| 6,787,323 B2 * | 9/2004 | Batley et al. ................ | 435/7.23 |
| 8,129,187 B2 * | 3/2012 | Yamanaka et al. ............ | 435/377 |
| 2009/0191159 A1 | 7/2009 | Sakurada et al. | |
| 2011/0177973 A1 * | 7/2011 | Rossner ........................ | 506/10 |

FOREIGN PATENT DOCUMENTS

WO   WO-2012012708 A1   1/2012

OTHER PUBLICATIONS

Moon et al. Inter J Stem Cells 4(1):24-34, 2011.*
Sylvester et al. Arch Surg. 139:93-99, 2004.*
Hanna et al. Cell 143:508-525, 2010.*
"International Application Serial No. PCT/US2011/044995, International Preliminary Report on Patentability mailed Jan. 31, 2013", 6 pgs.
Graf, Thomas, et al., "Forcing cells to change lineages", *Nature* 462(7273), (2009), 587.
Kim, Jeong Beom, et al., "Oct4—Induced Pluripotency in Adult Neural Stem Cells", *Cell*. 136, (2009), 411-419.
Maherali, Nimet, et al., "Guidelines and Techniques for the Generation of Induced Pluripotent Stem Cells", *Cell Stem Cell*, 3, (2018), 595-605.
Sugii, Shigeki, et al., "Human and mouse adipose-derived cells support feeder-independent induction of pluripotent stem cells", *Proc. Natl. Acad. Sci. USA*. 107(8), (2010), 3558-3563.
Sun, Ning, et al., "Feeder-free derivation of induced pluripotent stem cells from adult human adipose stem cells", *Proc. Natl. Acad. Sci. USA*, 106(37), (2009), 15720-15725.
Vierbuchen, Thomas, et al., "Direct conversion of fibroblasts to functional neurons by defined factors", *Nature*, 463(7284), (2010), 1035-1041.
Zhou, Qiao, et al., "Extreme Makeover: Converting One Cell into Another", *Cell Stem Cell*, 3(4), (2008), 382-388.
"International Application Serial No. PCT/US2011/044995, International Search Report mailed Dec. 12, 2011", 2 pgs.
"International Application Serial No. PCT/US2011/044995, Written Opinion mailed Dec. 12, 2011", 5 pgs.
Sartorelli, V, et al., "Molecular mechanisms of myogenic coactivation by p300: direct interaction with the activation domain of MyoD and with the MADS box of MEF2C", Mol. Cell Biol. vol. 17 No. 2, (Feb. 1997), 1010-1026.
Wang, Y., et al., "Reprogramming of mouse and human somatic cells by high-perfomance engineered factors", EMBO Rep., 12(4), (Apr. 1, 2011), 373-8.
Weintraub, H, et al., "Muscle-specific transcriptional activation by MyoD", Genes Dev., vol. 5, Abstract Page 1381, col. 1, Para 2-3, (1991), 1377-1386.

* cited by examiner

Primary Examiner — Marcia S Noble
(74) Attorney, Agent, or Firm — Schwegman Lundberg & Woessner, P.A.

(57) ABSTRACT

Described herein is a major breakthrough in nuclear reprogramming and induced pluripotent stem cell (iPSC) technology. Fusion of the powerful transcription activation domain (TAD) of MyoD to the Oct4 protein makes iPSCs generation faster, more efficient, purer, safer and feeder-free. Also, disclosed herein is the first report of the use of a TAD fused to a transcription factor as a method for making iPSCs. By combining transcription factors and TADs, this approach to nuclear reprogramming can have a range of applications from inducing pluripotency to inducing transdifferentiation without transitioning through iPSCs.

14 Claims, 28 Drawing Sheets

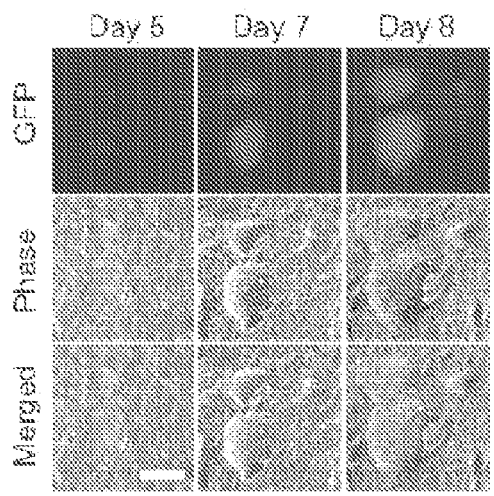
*Fig. 1C*
| M3O | Sox2 | Klf4 | c-Myc | GFP(+) |
|---|---|---|---|---|
| v | v | v | v | 3.6±0.5% |
| v |   | v | v | 0% |
| v | v |   | v | 0% |
| v | v | v |   | 0.44±0.03% |
| v | v |   |   | 0% |
| v |   | v |   | 0% |
| v |   |   | v | 0% |
| v |   |   |   | 0% |
*Fig. 1D*
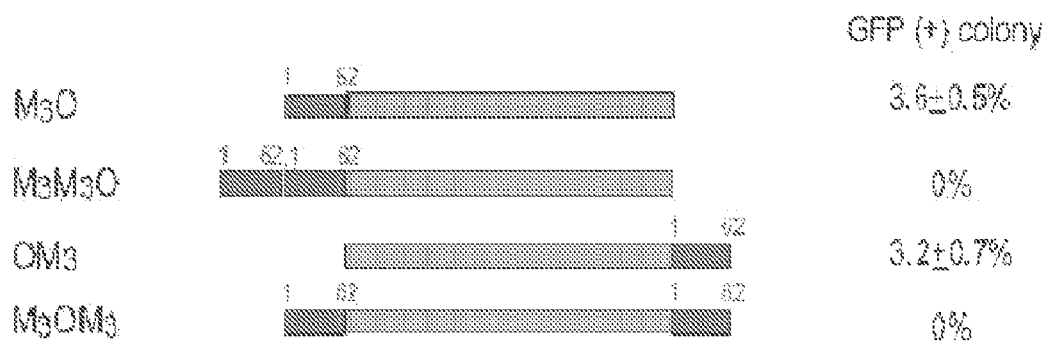
*Fig. 1E*

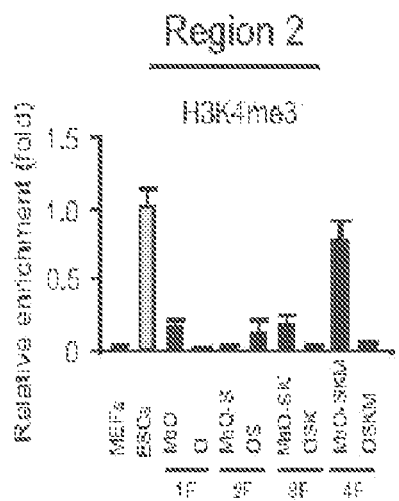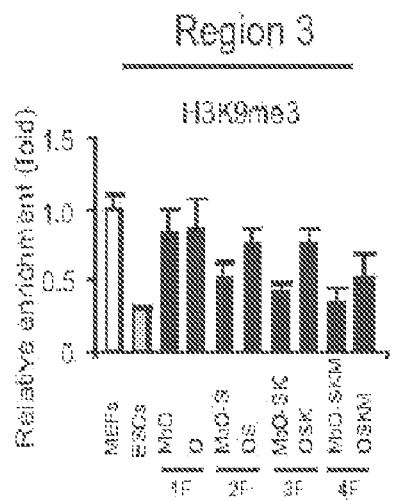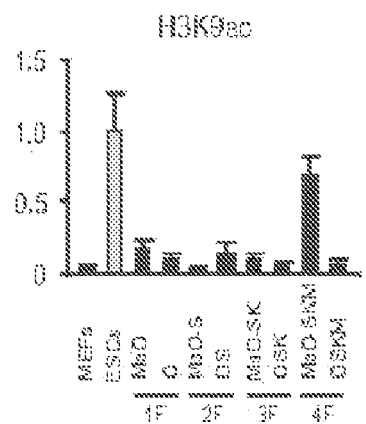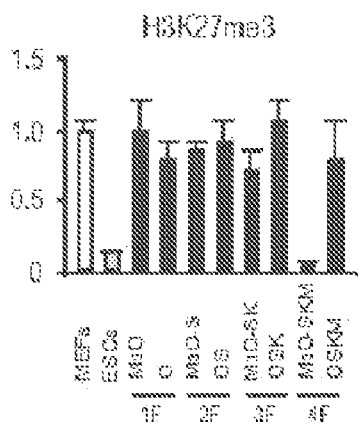
Fig. 7D          Fig. 7E

SEQUENCE LISTING

```
<160> NUMBER OF SEQ ID NOS: 88

<210> SEQ ID NO 1
<211> LENGTH: 33
<212> TYPE: DNA
<213> ORGANISM: Artificial Sequence
<220> FEATURE:
<223> OTHER INFORMATION: A synthetic primer

<400> SEQUENCE: 1
gagaattcgc catggagctt ctatcgccgc cac                           33

<210> SEQ ID NO 2
<211> LENGTH: 33
<212> TYPE: DNA
<213> ORGANISM: Artificial Sequence
<220> FEATURE:
<223> OTHER INFORMATION: A synthetic primer

<400> SEQUENCE: 2
caggtgtcca gccatgtgct cctccggttt cag                           33

<210> SEQ ID NO 3
<211> LENGTH: 33
<212> TYPE: DNA
<213> ORGANISM: Artificial Sequence
<220> FEATURE:
<223> OTHER INFORMATION: A synthetic primer

<400> SEQUENCE: 3
ctgaaaccgg aggagcacat ggctggacac ctg                           33

<210> SEQ ID NO 4
<211> LENGTH: 32
<212> TYPE: DNA
<213> ORGANISM: Artificial Sequence
<220> FEATURE:
<223> OTHER INFORMATION: A synthetic primer

<400> SEQUENCE: 4
cggaattctc tcagtttgaa tgcatgggag ag                            32

<210> SEQ ID NO 5
<211> LENGTH: 1245
<212> TYPE: DNA
<213> ORGANISM: Mus musculus

<400> SEQUENCE: 5
atggagcttc tatcgccgcc actccgggac atagacttga caggccccga cggctctctc    60
tgctcctttg agacagcaga cgacttctat gatgatccgt gtttcgactc accagacctg    120
cgcttttttg aggacctgga cccgcgcctg gtgcacgtgg gagccctcct gaaaccggag    180
gagcacatgg ctggacacct ggcttcagac ttcgccttct caccccacc aggtgggggt    240 gatgggtcag cagggctgga gccgggctgg gtggatcctc gaacctggct aagcttccaa    300
```

-continued

```
gggcctccag gtgggcctgg aatcggacca ggctcagagg tattggggat ctccccatgt    360
ccgcccgcat acgagttctg cggagggatg gcatactgtg gacctcaggt tggactgggc    420
ctagtccccc aagttggcgt ggagactttg cagcctgagg ccaggcagg agcacgagtg     480 gaaagcaact cagagggaac ctcctctgag ccctgtgccg accgcccaa tgccgtgaag     540 ttggagaagg tggaaccaac tcccgaggag tcccaggaca tgaaagccct gcagaaggag    600
ctagaacagt ttgccaagct gctgaagcag aagaggatca ccttgggta cacccaggcc    660 gacgtggggc tcaccctggg cgttctcttt ggaaaggtgt tcagccagac caccatctgt    720
cgcttcgagg ccttgcagct cagccttaag aacatgtgta agctgcggcc cctgctggag    780
aagtgggtgg aggaagccga caacaatgag aaccttcagg agatatgcaa atcggagacc    840
ctggtgcagg cccggaagag aaagcgaact agcattgaga accgtgtgag gtggagtctg    900
gagaccatgt ttctgaagtg cccgaagccc tccctacagc agatcactca catcgccaat    960
cagcttgggc tagagaagga tgtggttcga gtatggttct gtaaccggcg ccagaagggc   1020
aaaagatcaa gtattgagta ttcccaacga gaagagtatg aggctacagg gacacctttc   1080 ccagggggg ctgtatcctt tcctctgccc ccaggtcccc actttggcac cccaggctat    1140
ggaagccccc acttcaccac actctactca gtccctttc ctgagggcga ggcctttccc    1200
tctgttcccg tcactgctct gggctctccc atgcattcaa actga                   1245
```

<210> SEQ ID NO 6
<211> LENGTH: 33
<212> TYPE: DNA
<213> ORGANISM: Artificial Sequence
<220> FEATURE:
<223> OTHER INFORMATION: A synthetic primer

<400> SEQUENCE: 6
gagaattcgc catggagctt ctatcgccgc cac                                 33

<210> SEQ ID NO 7
<211> LENGTH: 33
<212> TYPE: DNA
<213> ORGANISM: Artificial Sequence
<220> FEATURE:
<223> OTHER INFORMATION: A synthetic primer

<400> SEQUENCE: 7
caggtgtcca gccatgtgct cctccggttt cag                                 33

<210> SEQ ID NO 8
<211> LENGTH: 33
<212> TYPE: DNA
<213> ORGANISM: Artificial Sequence
<220> FEATURE:
<223> OTHER INFORMATION: A synthetic primer

<400> SEQUENCE: 8
ctgaaaccgg aggagcacat ggctggacac ctg                                 33

<210> SEQ ID NO 9
<211> LENGTH: 32
<212> TYPE: DNA
<213> ORGANISM: Artificial Sequence
<220> FEATURE:
<223> OTHER INFORMATION: A synthetic primer

<400> SEQUENCE: 9

```
cggaattctc tcagtttgaa tgcatgggag ag                                    32
```

<210> SEQ ID NO 10
<211> LENGTH: 1251
<212> TYPE: DNA
<213> ORGANISM: Mus musculus

<400> SEQUENCE: 10

```
atggctggac acctggcttc agacttcgcc ttctcacccc caccaggtgg gggtgatggg     60
tcagcagggc tggagccggg ctgggtggat cctcgaacct ggctaagctt ccaagggcct    120
ccaggtgggc ctggaatcgg accaggctca gaggtattgg ggatctcccc atgtccgccc    180
gcatacgagt tctgcggagg gatggcatac tgtggacctc aggttggact gggcctagtc    240
ccccaagttg gcgtggagac tttgcagcct gagggccagg caggagcacg agtggaaagc    300
aactcagagg gaacctcctc tgagccctgt gccgaccgcc ccaatgccgt gaagttggag    360
aaggtggaac caactcccga ggagtcccag gacatgaaag ccctgcagaa ggagctagaa    420
cagtttgcca agctgctgaa gcagaagagg atcaccttgg ggtacaccca ggccgacgtg    480
gggctcaccc tgggcgttct ctttggaaag gtgttcagcc agaccaccat ctgtcgcttc    540
gaggccttgc agctcagcct taagaacatg tgtaagctgc ggcccctgct ggagaagtgg    600
gtggaggaag ccgacaacaa tgagaacctt caggagatat gcaaatcgga ccctggtg     660
caggcccgga gagaaagcg aactagcatt gagaaccgtg tgaggtggag tctggagacc    720
atgtttctga agtgcccgaa gccctcccta cagcagatca ctcacatcgc caatcagctt    780
gggctagaga aggatgtggt tcgagtatgg ttctgtaacc ggcgccagaa gggcaaaaga    840
tcaagtattg agtattccca acgagaagag tatgaggcta cagggacacc tttcccaggg    900
ggggctgtat cctttcctct gccccaggt ccccactttg gcaccccagg ctatggaagc    960
ccccacttca ccacactcta ctcagtccct tttcctgagg gcgaggcctt ccctctgtt   1020
cccgtcactg ctctgggctc tcccatgcat tcaaacgaat tcatggagct tctatcgccg   1080
ccactccggg acatagactt gacaggcccc gacggctctc tctgctcctt tgagacagca   1140
gacgacttct atgatgatcc gtgtttcgac tcaccagacc tgcgcttttt tgaggacctg   1200
gacccgcgcc tggtgcacgt gggagccctc ctgaaaccgg aggagcactg a            1251
```

<210> SEQ ID NO 11
<211> LENGTH: 24
<212> TYPE: DNA
<213> ORGANISM: Artificial Sequence
<220> FEATURE:
<223> OTHER INFORMATION: A synthetic primer

<400> SEQUENCE: 11

```
cgagaattca tggctggaca cctg                                             24
```

<210> SEQ ID NO 12
<211> LENGTH: 28
<212> TYPE: DNA
<213> ORGANISM: Artificial Sequence
<220> FEATURE:
<223> OTHER INFORMATION: A synthetic primer

<400> SEQUENCE: 12

```
cgagaattcg tttgaatgca tgggagag                                         28
```

<210> SEQ ID NO 13
<211> LENGTH: 31

```
<212> TYPE: DNA
<213> ORGANISM: Artificial Sequence
<220> FEATURE:
<223> OTHER INFORMATION: A synthetic primer

<400> SEQUENCE: 13
cgagaattca tggagcttct atcgccgcca c                              31

<210> SEQ ID NO 14
<211> LENGTH: 30
<212> TYPE: DNA
<213> ORGANISM: Artificial Sequence
<220> FEATURE:
<223> OTHER INFORMATION: A synthetic primer

<400> SEQUENCE: 14
cgactcgagt cagtgctcct ccggtttcag                                30

<210> SEQ ID NO 15
<211> LENGTH: 1437
<212> TYPE: DNA
<213> ORGANISM: Mus musculus

<400> SEQUENCE: 15
atggagcttc tatcgccgcc actccgggac atagacttga caggccccga cggctctctc    60
tgctcctttg agacagcaga cgacttctat gatgatccgt gtttcgactc accagacctg   120
cgcttttttg aggacctgga cccgcgcctg gtgcacgtgg gagccctcct gaaaccggag   180
gagcacatgg ctggacacct ggcttcagac ttcgccttct cacccccacc aggtgggggt   240
gatgggtcag cagggctgga gccgggctgg gtggatcctc gaacctggct aagcttccaa   300
gggcctccag gtgggcctgg aatcggacca ggctcagagg tattgggat ctccccatgt    360 ccgcccgcat acgagttctg cggagggatg gcatactgtg gacctcaggt tggactgggc   420
ctagtccccc aagttggcgt ggagactttg cagcctgagg ccaggcagg agcacgagtg     480 gaaagcaact cagagggaac ctcctctgag ccctgtgccg accgcccaa tgccgtgaag    540 ttggagaagg tggaaccaac tcccgaggag tcccaggaca tgaaagccct gcagaaggag    600
ctagaacagt tgccaagct gctgaagcag aagaggatca ccttggggta cacccaggcc     660
gacgtggggc tcaccctggg cgttctcttt ggaaaggtgt tcagccagac caccatctgt    720
cgcttcgagg ccttgcagct cagccttaag aacatgtgta gctgcgcgcc cctgctggag   780
aagtgggtgg aggaagccga caacaatgag aaccttcagg agatatgcaa atcggagacc    840
ctggtgcagg cccggaagag aaagcgaact agcattgaga accgtgtgag gtggagtctg    900
gagaccatgt ttctgaagtg cccgaagccc tccctacagc agatcactca catcgccaat   960
cagcttgggc tagagaagga tgtggttcga gtatggttct gtaaccggcg ccagaagggc   1020
aaaagatcaa gtattgagta ttcccaacga gaagagtatg aggctacagg acacctttc    1080 ccagggggg ctgtatcctt tcctctgccc caggtccccc actttggcac cccaggctat    1140
ggaagccccc acttcaccac actctactca gtcccttttc ctgagggcga ggcctttccc   1200
tctgttcccg tcactgctct gggctctccc atgcattcaa acgaattcat ggagcttcta   1260
tcgccgccac tccgggacat agacttgaca ggccccgacg ctctctctg ctccttgag    1320 acagcagacg acttctatga tgatccgtgt ttcgactcac cagacctgcg cttttttgag   1380
gacctggacc cgcgcctggt gcacgtggga gccctcctga aaccggagga gcactga       1437

<210> SEQ ID NO 16
```

```
<211> LENGTH: 33
<212> TYPE: DNA
<213> ORGANISM: Artificial Sequence
<220> FEATURE:
<223> OTHER INFORMATION: A synthetic primer

<400> SEQUENCE: 16
gagaattcgc catggagctt ctatcgccgc cac                          33

<210> SEQ ID NO 17
<211> LENGTH: 31
<212> TYPE: DNA
<213> ORGANISM: Artificial Sequence
<220> FEATURE:
<223> OTHER INFORMATION: A synthetic primer

<400> SEQUENCE: 17
caggtgtcca gccatatcag cgttggtggt c                            31

<210> SEQ ID NO 18
<211> LENGTH: 31
<212> TYPE: DNA
<213> ORGANISM: Artificial Sequence
<220> FEATURE:
<223> OTHER INFORMATION: A synthetic primer

<400> SEQUENCE: 18
gaccaccaac gctgatatgg ctggacacct g                            31

<210> SEQ ID NO 19
<211> LENGTH: 28
<212> TYPE: DNA
<213> ORGANISM: Artificial Sequence
<220> FEATURE:
<223> OTHER INFORMATION: A synthetic primer

<400> SEQUENCE: 19
cgagaattcg tttgaatgca tgggagag                                28

<210> SEQ ID NO 20
<211> LENGTH: 1269
<212> TYPE: DNA
<213> ORGANISM: Homo sapiens

<400> SEQUENCE: 20
atggagctac tgtcgccacc gctccgcgac gtagacctga cggcccccga cggctctctc     60
tgctcctttg ccacaacgga cgacttctat gacgacccgt gtttcgactc cccggacctg    120
cgcttcttcg aagacctgga cccgcgcctg atgcacgtgg gcgcgctcct gaaacccgaa    180
gagcacatgg cgggacacct ggcttcggat ttcgccttct cgccccctcc aggtggtgga    240
ggtgatgggc cagggggggcc ggagccgggc tgggttgatc ctcggacctg gctaagcttc    300
caaggccctc ctggagggcc aggaatcggg ccggggggttg gccaggctc tgaggtgtgg    360 gggattcccc catgcccccc gccgtatgag ttctgtgggg gatggcgta ctgtgggccc    420 caggttggag tggggctagt gccccaaggc ggcttggaga cctctcagcc tgagggcgaa    480
gcaggagtcg gggtggagag caactccgat ggggcctccc cggagccctg caccgtcacc    540
cctggtgccg tgaagctgga aaggagaag ctggagcaaa acccggagga gtcccaggac    600
atcaaagctc tgcagaaaga actcgagcaa tttgccaagc tcctgaagca gaaggaggatc    660 accctgggat atacacaggc cgatgtgggg ctcaccctgg gggttctatt tgggaaggta    720
ttcagccaaa cgaccatctg ccgctttgag gctctgcagc ttagcttcaa gaacatgtgt    780
```

-continued

```
aagctgcggc ccttgctgca gaagtgggtg gaggaagctg acaacaatga aaatcttcag      840
gagatatgca aagcagaaac cctcgtgcag gcccgaaaga gaaagcgaac cagtatcgag      900
aaccgagtga gaggcaacct ggagaatttg ttcctgcagt gcccgaaacc cacactgcag      960
cagatcagcc acatcgccca gcagcttggg ctcgagaagg atgtggtccg agtgtggttc     1020
tgtaaccggc gccagaaggg caagcgatca agcagcgact atgcacaacg agaggatttt     1080
gaggctgctg ggtctccttt ctcaggggga ccagtgtcct ttcctctggc cccagggccc     1140
cattttggta ccccaggcta tgggagccct cacttcactg cactgtactc ctcggtccct     1200
ttccctgagg gggaagcctt tccccctgtc tccgtcacca ctctgggctc tcccatgcat     1260
tcaaactga                                                             1269
```

<210> SEQ ID NO 21
<211> LENGTH: 31
<212> TYPE: DNA
<213> ORGANISM: Artificial Sequence
<220> FEATURE:
<223> OTHER INFORMATION: A synthetic primer

<400> SEQUENCE: 21
cgagaattcg ccatggagct actgtcgcca c                                    31

<210> SEQ ID NO 22
<211> LENGTH: 33
<212> TYPE: DNA
<213> ORGANISM: Artificial Sequence
<220> FEATURE:
<223> OTHER INFORMATION: A synthetic primer

<400> SEQUENCE: 22
caggtgtccc gccatgtgct cttcgggttt cag                                  33

<210> SEQ ID NO 23
<211> LENGTH: 33
<212> TYPE: DNA
<213> ORGANISM: Artificial Sequence
<220> FEATURE:
<223> OTHER INFORMATION: A synthetic primer

<400> SEQUENCE: 23
ctgaaacccg aagagcacat ggcgggacac ctg                                  33

<210> SEQ ID NO 24
<211> LENGTH: 39
<212> TYPE: DNA
<213> ORGANISM: Artificial Sequence
<220> FEATURE:
<223> OTHER INFORMATION: A synthetic primer

<400> SEQUENCE: 24
cgtgaattcc tcgagtctca gtttgaatgc atgggagag                            39

<210> SEQ ID NO 25
<211> LENGTH: 39
<212> TYPE: DNA
<213> ORGANISM: Artificial Sequence
<220> FEATURE:
<223> OTHER INFORMATION: A synthetic primer

<400> SEQUENCE: 25
cgaggatccg ccatgtcgac ggccccccg accgatgtc                             39

<210> SEQ ID NO 26
<211> LENGTH: 30
<212> TYPE: DNA
<213> ORGANISM: Artificial Sequence
<220> FEATURE:
<223> OTHER INFORMATION: A synthetic primer

<400> SEQUENCE: 26
cgactcgagg aattccccac cgtactcgtc                                    30

<210> SEQ ID NO 27
<211> LENGTH: 1307
<212> TYPE: DNA
<213> ORGANISM: Artificial Sequence
<220> FEATURE:
<223> OTHER INFORMATION: A synthetic sequence

<400> SEQUENCE: 27
atgtcgacgc cccccgacc gatgtcagcc tggggacga gctccactta gacggcgagg     60
acgtggcgat ggcgcatgcc gacgcgctag acgatttcga tctggacatg ttggggacg    120 gggattcccc gggtccggga tttacccccc acgactccgc cccctacggc gctctggata   180
tggccgactt cgagtttgag cagatgttta ccgatgccct tggaattgac gagtacggtg   240 ggaattcat ggctggacac ctggcttcag acttcgcctt ctcacccca ccaggtgggg     300 gtgatgggtc agcagggctg gagccgggct gggtggatcc tcgaacctgg ctaagcttcc   360
aagggcctcc aggtgggcct ggaatcggac caggctcaga ggtattgggg atctccccat   420
gtccgcccgc atacgagttc tgcggaggga tggcatactg tggacctcag gttggactgg   480
gcctagtccc ccaagttggc gtggagactt tgcagcctga gggccaggca ggagcacgag   540
tggaaagcaa ctcagaggga acctcctctg agccctgtgc cgaccgcccc aatgccgtga   600
agttggagaa ggtggaacca actcccgagg agtcccagga catgaaagcc ctgcagaagg   660
agctagaaca gtttgccaag ctgctgaagc agaagaggat caccttgggg tacacccagg   720
ccgacgtggg gctcacccctg ggcgttctct ttggaaaggt gttcagccag accaccatct   780
gtcgcttcga ggccttgcag ctcagcctta gaacatgtg taagctgcgg ccctgctgg    840 agaagtgggt ggaggaagcc gacaacaatg agaaccttca ggagatatgc aaatcggaga   900
ccctggtgca ggcccggaag agaaagcgaa ctagcattga gaaccgtgtg aggtggagtc   960
tggagaccat gtttctgaag tgcccgaagc cctccctaca gcagatcact cacatcgcca  1020
atcagcttgg gctagagaag gatgtggttc gagtatggtt ctgtaaccgg cgccagaagg  1080
gcaaaagatc aagtattgag tattcccaac gagaagagta tgaggctaca gggacacctt  1140
tcccaggggg ggctgtatcc tttcctctgc ccccaggtcc ccactttggc ccccaggct    1200 atggaagccc ccacttcacc acactctact cagtcccttt tcctgagggc gaggcctttc   1260
cctctgttcc cgtcactgct ctgggctctc ccatgcattc aaactga                1307

<210> SEQ ID NO 28
<211> LENGTH: 32
<212> TYPE: DNA
<213> ORGANISM: Artificial Sequence
<220> FEATURE:
<223> OTHER INFORMATION: A synthetic primer

<400> SEQUENCE: 28
cgagaattcg ccatgttggg ggacggggat tc                                 32

<210> SEQ ID NO 29
<211> LENGTH: 30
<212> TYPE: DNA
<213> ORGANISM: Artificial Sequence
<220> FEATURE:
<223> OTHER INFORMATION: A synthetic primer

<400> SEQUENCE: 29
caggtgtcca gccatcccac cgtactcgtc                              30

<210> SEQ ID NO 30
<211> LENGTH: 30
<212> TYPE: DNA
<213> ORGANISM: Artificial Sequence
<220> FEATURE:
<223> OTHER INFORMATION: A synthetic primer

<400> SEQUENCE: 30
gacgagtacg gtgggatggc tggacacctg                              30

<210> SEQ ID NO 31
<211> LENGTH: 33
<212> TYPE: DNA
<213> ORGANISM: Artificial Sequence
<220> FEATURE:
<223> OTHER INFORMATION: A synthetic primer

<400> SEQUENCE: 31
gcgctcgagt ctcagtttga atgcatggga gag                          33

<210> SEQ ID NO 32
<211> LENGTH: 32
<212> TYPE: DNA
<213> ORGANISM: Artificial Sequence
<220> FEATURE:
<223> OTHER INFORMATION: A synthetic primer

<400> SEQUENCE: 32
cgagaattcg ccatgttggg ggacggggat tc                           32

<210> SEQ ID NO 33
<211> LENGTH: 30
<212> TYPE: DNA
<213> ORGANISM: Artificial Sequence
<220> FEATURE:
<223> OTHER INFORMATION: A synthetic primer

<400> SEQUENCE: 33
caggtgtcca gccatcccac cgtactcgtc                              30

<210> SEQ ID NO 34
<211> LENGTH: 30
<212> TYPE: DNA
<213> ORGANISM: Artificial Sequence
<220> FEATURE:
<223> OTHER INFORMATION: A synthetic primer

<400> SEQUENCE: 34
gacgagtacg gtgggatggc tggacacctg                              30

<210> SEQ ID NO 35
<211> LENGTH: 33
<212> TYPE: DNA
<213> ORGANISM: Artificial Sequence
<220> FEATURE:
<223> OTHER INFORMATION: A synthetic primer

```
<400> SEQUENCE: 35
gcgctcgagt ctcagtttga atgcatggga gag                          33

<210> SEQ ID NO 36
<211> LENGTH: 23
<212> TYPE: DNA
<213> ORGANISM: Artificial Sequence
<220> FEATURE:
<223> OTHER INFORMATION: A synthetic primer

<400> SEQUENCE: 36
tctttccacc aggcccccgg ctc                                     23

<210> SEQ ID NO 37
<211> LENGTH: 23
<212> TYPE: DNA
<213> ORGANISM: Artificial Sequence
<220> FEATURE:
<223> OTHER INFORMATION: A synthetic primer

<400> SEQUENCE: 37
tgcgggcgga catggggaga tcc                                     23

<210> SEQ ID NO 38
<211> LENGTH: 24
<212> TYPE: DNA
<213> ORGANISM: Artificial Sequence
<220> FEATURE:
<223> OTHER INFORMATION: A synthetic primer

<400> SEQUENCE: 38
aaaggagaga agtttggagc ccga                                    24

<210> SEQ ID NO 39
<211> LENGTH: 24
<212> TYPE: DNA
<213> ORGANISM: Artificial Sequence
<220> FEATURE:
<223> OTHER INFORMATION: A synthetic primer

<400> SEQUENCE: 39
gggcgaagtg caattgggat gaaa                                    24

<210> SEQ ID NO 40
<211> LENGTH: 24
<212> TYPE: DNA
<213> ORGANISM: Artificial Sequence
<220> FEATURE:
<223> OTHER INFORMATION: A synthetic primer

<400> SEQUENCE: 40
agcagaagat gcggactgtg ttct                                    24

<210> SEQ ID NO 41
<211> LENGTH: 24
<212> TYPE: DNA
<213> ORGANISM: Artificial Sequence
<220> FEATURE:
<223> OTHER INFORMATION: A synthetic primer

<400> SEQUENCE: 41
ccgcttgcac ttcatccttt ggtt                                    24

<210> SEQ ID NO 42
<211> LENGTH: 23
```

```
<212> TYPE: DNA
<213> ORGANISM: Artificial Sequence
<220> FEATURE:
<223> OTHER INFORMATION: A synthetic primer

<400> SEQUENCE: 42
gcctgacccg agagaagaag aag                                              23

<210> SEQ ID NO 43
<211> LENGTH: 25
<212> TYPE: DNA
<213> ORGANISM: Artificial Sequence
<220> FEATURE:
<223> OTHER INFORMATION: A synthetic primer

<400> SEQUENCE: 43
tggtggtgaa gttcgctaga gtaag                                            25

<210> SEQ ID NO 44
<211> LENGTH: 22
<212> TYPE: DNA
<213> ORGANISM: Artificial Sequence
<220> FEATURE:
<223> OTHER INFORMATION: A synthetic primer

<400> SEQUENCE: 44
ccaccactga aaggaacaac aa                                               22

<210> SEQ ID NO 45
<211> LENGTH: 23
<212> TYPE: DNA
<213> ORGANISM: Artificial Sequence
<220> FEATURE:
<223> OTHER INFORMATION: A synthetic primer

<400> SEQUENCE: 45
tccaacacga aatacacgtt gac                                              23

<210> SEQ ID NO 46
<211> LENGTH: 20
<212> TYPE: DNA
<213> ORGANISM: Artificial Sequence
<220> FEATURE:
<223> OTHER INFORMATION: A synthetic primer

<400> SEQUENCE: 46
ccatgaacaa ggaagggaaa                                                  20

<210> SEQ ID NO 47
<211> LENGTH: 20
<212> TYPE: DNA
<213> ORGANISM: Artificial Sequence
<220> FEATURE:
<223> OTHER INFORMATION: A synthetic primer

<400> SEQUENCE: 47
tccgctgtgt gtccatttag                                                  20

<210> SEQ ID NO 48
<211> LENGTH: 19
<212> TYPE: DNA
<213> ORGANISM: Artificial Sequence
<220> FEATURE:
<223> OTHER INFORMATION: A synthetic primer

<400> SEQUENCE: 48
```
tgcaccacca actgcttag                                                   19

<210> SEQ ID NO 49
<211> LENGTH: 18
<212> TYPE: DNA
<213> ORGANISM: Artificial Sequence
<220> FEATURE:
<223> OTHER INFORMATION: A synthetic primer

<400> SEQUENCE: 49
gatgcaggga tgatgttc                                                    18

<210> SEQ ID NO 50
<211> LENGTH: 20
<212> TYPE: DNA
<213> ORGANISM: Artificial Sequence
<220> FEATURE:
<223> OTHER INFORMATION: A synthetic primer

<400> SEQUENCE: 50
cctcacttca ctgcactgta                                                  20

<210> SEQ ID NO 51
<211> LENGTH: 20
<212> TYPE: DNA
<213> ORGANISM: Artificial Sequence
<220> FEATURE:
<223> OTHER INFORMATION: A synthetic primer

<400> SEQUENCE: 51
caggttttct ttccctagct                                                  20

<210> SEQ ID NO 52
<211> LENGTH: 19
<212> TYPE: DNA
<213> ORGANISM: Artificial Sequence
<220> FEATURE:
<223> OTHER INFORMATION: A synthetic primer

<400> SEQUENCE: 52
cccagcagac ttcacatgt                                                   19

<210> SEQ ID NO 53
<211> LENGTH: 20
<212> TYPE: DNA
<213> ORGANISM: Artificial Sequence
<220> FEATURE:
<223> OTHER INFORMATION: A synthetic primer

<400> SEQUENCE: 53
cctcccattt ccctcgtttt                                                  20

<210> SEQ ID NO 54
<211> LENGTH: 20
<212> TYPE: DNA
<213> ORGANISM: Artificial Sequence
<220> FEATURE:
<223> OTHER INFORMATION: A synthetic primer

<400> SEQUENCE: 54
gatgaactga ccaggcacta                                                  20

<210> SEQ ID NO 55
<211> LENGTH: 20
<212> TYPE: DNA
<213> ORGANISM: Artificial Sequence

```
<220> FEATURE:
<223> OTHER INFORMATION: A synthetic primer

<400> SEQUENCE: 55
gtgggtcata tccactgtct                                               20

<210> SEQ ID NO 56
<211> LENGTH: 20
<212> TYPE: DNA
<213> ORGANISM: Artificial Sequence
<220> FEATURE:
<223> OTHER INFORMATION: A synthetic primer

<400> SEQUENCE: 56
tgcctcaaat tggactttgg                                               20

<210> SEQ ID NO 57
<211> LENGTH: 22
<212> TYPE: DNA
<213> ORGANISM: Artificial Sequence
<220> FEATURE:
<223> OTHER INFORMATION: A synthetic primer

<400> SEQUENCE: 57
gattgaaatt ctgtgtaact gc                                            22

<210> SEQ ID NO 58
<211> LENGTH: 20
<212> TYPE: DNA
<213> ORGANISM: Artificial Sequence
<220> FEATURE:
<223> OTHER INFORMATION: A synthetic primer

<400> SEQUENCE: 58
tgaacctcag ctacaaacag                                               20

<210> SEQ ID NO 59
<211> LENGTH: 20
<212> TYPE: DNA
<213> ORGANISM: Artificial Sequence
<220> FEATURE:
<223> OTHER INFORMATION: A synthetic primer

<400> SEQUENCE: 59
tggtggtagg aagagtaaag                                               20

<210> SEQ ID NO 60
<211> LENGTH: 24
<212> TYPE: DNA
<213> ORGANISM: Artificial Sequence
<220> FEATURE:
<223> OTHER INFORMATION: A synthetic primer

<400> SEQUENCE: 60
gagcatgcag aagcgcagat caaa                                          24

<210> SEQ ID NO 61
<211> LENGTH: 24
<212> TYPE: DNA
<213> ORGANISM: Artificial Sequence
<220> FEATURE:
<223> OTHER INFORMATION: A synthetic primer

<400> SEQUENCE: 61
tatggctgat gctctggcag aagt                                          24
```

<210> SEQ ID NO 62
<211> LENGTH: 24
<212> TYPE: DNA
<213> ORGANISM: Artificial Sequence
<220> FEATURE:
<223> OTHER INFORMATION: A synthetic primer

<400> SEQUENCE: 62
aggcttcata ggcatgctta ccct                                              24

<210> SEQ ID NO 63
<211> LENGTH: 24
<212> TYPE: DNA
<213> ORGANISM: Artificial Sequence
<220> FEATURE:
<223> OTHER INFORMATION: A synthetic primer

<400> SEQUENCE: 63
tgaagccttg ctctcttggt cact                                              24

<210> SEQ ID NO 64
<211> LENGTH: 24
<212> TYPE: DNA
<213> ORGANISM: Artificial Sequence
<220> FEATURE:
<223> OTHER INFORMATION: A synthetic primer

<400> SEQUENCE: 64
agacacagat ggttgggttc acct                                              24

<210> SEQ ID NO 65
<211> LENGTH: 24
<212> TYPE: DNA
<213> ORGANISM: Artificial Sequence
<220> FEATURE:
<223> OTHER INFORMATION: A synthetic primer

<400> SEQUENCE: 65
tgcactcact ctcccttctt gctt                                              24

<210> SEQ ID NO 66
<211> LENGTH: 24
<212> TYPE: DNA
<213> ORGANISM: Artificial Sequence
<220> FEATURE:
<223> OTHER INFORMATION: A synthetic primer

<400> SEQUENCE: 66
acacctgtgc cagactaaga tgct                                              24

<210> SEQ ID NO 67
<211> LENGTH: 24
<212> TYPE: DNA
<213> ORGANISM: Artificial Sequence
<220> FEATURE:
<223> OTHER INFORMATION: A synthetic primer

<400> SEQUENCE: 67
tgacggtggc agaggttctt acaa                                              24

<210> SEQ ID NO 68
<211> LENGTH: 24
<212> TYPE: DNA
<213> ORGANISM: Artificial Sequence
<220> FEATURE:
<223> OTHER INFORMATION: A synthetic primer -continued

<400> SEQUENCE: 68
tgaatagctg accaccagca cact                                          24

<210> SEQ ID NO 69
<211> LENGTH: 24
<212> TYPE: DNA
<213> ORGANISM: Artificial Sequence
<220> FEATURE:
<223> OTHER INFORMATION: A synthetic primer

<400> SEQUENCE: 69
acaggctcca gcctcagtac attt                                          24

<210> SEQ ID NO 70
<211> LENGTH: 20
<212> TYPE: DNA
<213> ORGANISM: Artificial Sequence
<220> FEATURE:
<223> OTHER INFORMATION: A synthetic primer

<400> SEQUENCE: 70
tgtgcaccaa catctacaag                                               20

<210> SEQ ID NO 71
<211> LENGTH: 20
<212> TYPE: DNA
<213> ORGANISM: Artificial Sequence
<220> FEATURE:
<223> OTHER INFORMATION: A synthetic primer

<400> SEQUENCE: 71
gcgttcttgg ctttcaggat                                               20

<210> SEQ ID NO 72
<211> LENGTH: 24
<212> TYPE: DNA
<213> ORGANISM: Artificial Sequence
<220> FEATURE:
<223> OTHER INFORMATION: A synthetic primer

<400> SEQUENCE: 72
tgcccaagaa gtgttccctg tgta                                          24

<210> SEQ ID NO 73
<211> LENGTH: 24
<212> TYPE: DNA
<213> ORGANISM: Artificial Sequence
<220> FEATURE:
<223> OTHER INFORMATION: A synthetic primer

<400> SEQUENCE: 73
aaagtggtag tacgtgcaga cggt                                          24

<210> SEQ ID NO 74
<211> LENGTH: 20
<212> TYPE: DNA
<213> ORGANISM: Artificial Sequence
<220> FEATURE:
<223> OTHER INFORMATION: A synthetic primer

<400> SEQUENCE: 74
aacagcgaca cccactcctc                                               20

<210> SEQ ID NO 75

```
<211> LENGTH: 24
<212> TYPE: DNA
<213> ORGANISM: Artificial Sequence
<220> FEATURE:
<223> OTHER INFORMATION: A synthetic primer

<400> SEQUENCE: 75
cataccagga aatgagcttg acaa                                              24

<210> SEQ ID NO 76
<211> LENGTH: 22
<212> TYPE: DNA
<213> ORGANISM: Artificial Sequence
<220> FEATURE:
<223> OTHER INFORMATION: A synthetic primer

<400> SEQUENCE: 76
aggttgaaaa tgaaggtttt tt                                                22

<210> SEQ ID NO 77
<211> LENGTH: 23
<212> TYPE: DNA
<213> ORGANISM: Artificial Sequence
<220> FEATURE:
<223> OTHER INFORMATION: A synthetic primer

<400> SEQUENCE: 77
tccaacccta ctaacccatc acc                                               23

<210> SEQ ID NO 78
<211> LENGTH: 24
<212> TYPE: DNA
<213> ORGANISM: Artificial Sequence
<220> FEATURE:
<223> OTHER INFORMATION: A synthetic primer

<400> SEQUENCE: 78
ggaactgggt gtgggaggt tgta                                               24

<210> SEQ ID NO 79
<211> LENGTH: 29
<212> TYPE: DNA
<213> ORGANISM: Artificial Sequence
<220> FEATURE:
<223> OTHER INFORMATION: A synthetic primer

<400> SEQUENCE: 79
agcagattaa ggaagggcta ggacgagag                                         29

<210> SEQ ID NO 80
<211> LENGTH: 26
<212> TYPE: DNA
<213> ORGANISM: Artificial Sequence
<220> FEATURE:
<223> OTHER INFORMATION: A synthetic primer

<400> SEQUENCE: 80
aggtcaaggg gctagagggt gggatt                                            26

<210> SEQ ID NO 81
<211> LENGTH: 23
<212> TYPE: DNA
<213> ORGANISM: Artificial Sequence
<220> FEATURE:
<223> OTHER INFORMATION: A synthetic primer

<400> SEQUENCE: 81
```
tgagaaggcg aagtctgaag cca                                           23

<210> SEQ ID NO 82
<211> LENGTH: 24
<212> TYPE: DNA
<213> ORGANISM: Artificial Sequence
<220> FEATURE:
<223> OTHER INFORMATION: A synthetic primer

<400> SEQUENCE: 82
taggagctct tgtttgggcc atgt                                          24

<210> SEQ ID NO 83
<211> LENGTH: 24
<212> TYPE: DNA
<213> ORGANISM: Artificial Sequence
<220> FEATURE:
<223> OTHER INFORMATION: A synthetic primer

<400> SEQUENCE: 83
acaagggtct gctcgtgtaa aggt                                          24

<210> SEQ ID NO 84
<211> LENGTH: 30
<212> TYPE: DNA
<213> ORGANISM: Artificial Sequence
<220> FEATURE:
<223> OTHER INFORMATION: A synthetic primer

<400> SEQUENCE: 84
ttttggtttt tagggtaagg tactgggaag                                    30

<210> SEQ ID NO 85
<211> LENGTH: 30
<212> TYPE: DNA
<213> ORGANISM: Artificial Sequence
<220> FEATURE:
<223> OTHER INFORMATION: A synthetic primer

<400> SEQUENCE: 85
ccacgtgaat aatcctatat gcatcacaat                                    30

<210> SEQ ID NO 86
<211> LENGTH: 24
<212> TYPE: DNA
<213> ORGANISM: Artificial Sequence
<220> FEATURE:
<223> OTHER INFORMATION: A synthetic primer

<400> SEQUENCE: 86
cacatgaagg agcacccgga ttat                                          24

<210> SEQ ID NO 87
<211> LENGTH: 24
<212> TYPE: DNA
<213> ORGANISM: Artificial Sequence
<220> FEATURE:
<223> OTHER INFORMATION: A synthetic primer

<400> SEQUENCE: 87
tccgggaagc gtgtacttat cctt                                          24

<210> SEQ ID NO 88
<211> LENGTH: 1194
<212> TYPE: DNA

<213> ORGANISM: Artificial Sequence
<220> FEATURE:
<223> OTHER INFORMATION: A synthetic sequence

<400> SEQUENCE: 88

```
atgttggggg acggggattc cccgggtccg ggatttaccc cccacgactc cgcccctac      60
ggcgctctgg atatggccga cttcgagttt gagcagatgt ttaccgatgc ccttggaatt    120
gacgagtacg gtgggatggc tggacacctg gcttcagact tcgccttctc accccacca    180
ggtgggggtg atgggtcagc agggctggag ccgggctggg tggatcctcg aacctggcta    240
agcttccaag ggcctccagg tgggcctgga atcggaccag gctcagaggt attggggatc    300
tccccatgtc cgcccgcata cgagttctgc ggagggatgg catactgtgg acctcaggtt    360
ggactgggcc tagtccccca agttggcgtg gagactttgc agcctgaggg ccaggcagga    420
gcacgagtgg aaagcaactc agagggaacc tcctctgagc cctgtgccga ccgcccaat    480
gccgtgaagt tggagaaggt ggaaccaact cccgaggagt cccaggacat gaaagccctg    540
cagaaggagc tagaacagtt tgccaagctg ctgaagcaga agaggatcac cttggggtac    600
acccaggccg acgtggggct caccctgggc gttctctttg gaaaggtgtt cagccagacc    660
accatctgtc gcttcgaggc cttgcagctc agccttaaga acatgtgtaa gctgcggccc    720
ctgctggaga agtgggtgga ggaagccgac aacaatgaga accttcagga gatatgcaaa    780
tcggagaccc tggtgcaggc ccggaagaga aagcgaacta gcattgagaa ccgtgtgagg    840
tggagtctgg agaccatgtt tctgaagtgc ccgaagccct ccctacagca gatcactcac    900
atcgccaatc agcttgggct agagaaggat gtggttcgag tatggttctg taaccggcgc    960
cagaagggca aaagatcaag tattgagtat tcccaacgag aagagtatga ggctacaggg   1020
acacctttcc caggggggc tgtatccttt cctctgcccc caggtcccca ctttggcacc   1080
ccaggctatg gaagccccca cttcaccaca ctctactcag tcccttttcc tgagggcgag   1140
gcctttccct ctgttcccgt cactgctctg ggctctccca tgcattcaaa ctga         1194
```

INDUCED PLURIPOTENT STEM CELLS

RELATED APPLICATIONS

This application is a U.S. National Stage Filing under 35 U.S.C. 371 from International Application No. PCT/US2011/044995, filed on 22 Jul. 2011, and published as WO 2012/012708 A1 on 26 Jan. 2012, which claims priority from U.S. Provisional Application Ser. No. 61/366,821 filed Jul. 22, 2010 and 61/390,454 filed Oct. 6, 2010, which applications and publication are incorporated herein by reference in their entirety.

STATEMENT OF GOVERNMENT RIGHTS

This invention was made with government support under United States Grant No. R01 DK082430-01 from National Institute of Diabetes and Digestive and Kidney Diseases, National Institutes of Health. The government has rights in the invention.

BACKGROUND OF THE INVENTION

Nuclear reprogramming, the process of converting one cell type into another by resetting the pattern of gene expression, can be achieved through forced expression of defined transcription factors. One example is the induced pluripotent stem cells (iPSCs) prepared by transducing four genes (e.g., Oct4, Sox2, Klf4 and c-Myc, called OSKM hereafter) into a cell type to be dedifferentiated. iPSCs are a type of pluripotent stem cell artificially derived by reprogramming a somatic cell. iPSCs are morphologically similar to embryonic stem cells and are capable of differentiating into a variety of different somatic cell types. This technology allows researchers to obtain pluripotent stem cells for use in a research setting. iPSCs also have therapeutic uses for the treatment of disease without the need for stem cells derived from an embryonic source.

However, generally less than 1% of transduced cells are reprogrammed to form iPSCs, and the entire process of establishing iPSC clones is long (over a month).

SUMMARY OF THE INVENTION

Described herein is a novel approach to nuclear reprogramming using a fusion protein (a protein created through the joining of two or more genes or portions thereof in any orientation or copy number (e.g., from about 1 to about 2, about 3, about 4, about 5 or more copies of genes for example) which originally coded for separate proteins or portions thereof) of a transcription activation domain (TAD) of a gene, for example, MyoD and a transcription factor, for example, Oct4 (such a fusion protein is designated herein as $M_3O$) that greatly improves the efficiency of reprogramming and accelerates iPSC production. iPSC colonies emerged five days after transduction of Sox2, Klf4 and c-Myc (SKM) and $M_3O$ into fibroblasts, with colonies rapidly enlarging in the absence of feeder cells. The pluripotency of iPSCs was confirmed by genome-wide gene expression analysis, teratoma formation, and chimera formation, including germline transmission. Transduction of $M_3O$ and SKM increased chromatin accessibility at the Oct4 promoter, facilitated recruitment of the Oct4-binding Paf1 complex, and remodeled many histone modifications at pluripotency genes to an embryonic stem cell (ESC)-like state more efficiently than transduction of OSKM. Thus, discussed herein is a novel approach to nuclear reprogramming in which a wide variety of TADs can be combined with related or unrelated transcription factors to reprogram the pattern of gene expression, with applications ranging from induction of pluripotency to direct transdifferentiation.

One embodiment provides iPSCs derived by nuclear reprogramming of a somatic cell with a fusion protein. The somatic cell can be a mammalian cell, for example a mouse cell or a human cell. One embodiment provides a fusion protein for induction of pluripotent stem cells. Another embodiment provides such a pluripotent stem cell, wherein the reprogramming comprises contacting the somatic cell with a fusion protein or DNA encoding the fusion protein. The disclosed methods and fusion proteins can be used to conveniently and reproducibly establish iPSCs having pluripotency and growth ability similar to that of ES cells (ESCs).

One embodiment provides a method for preparing an induced pluripotent stem cell by nuclear reprogramming of a somatic cell, which comprises introducing a nucleic acid sequence, by methods available to one of skill in the art, coding for a fusion protein of an unrelated/heterologous transactivation domain and a transcription factor into the somatic cell. One embodiment provides an induced pluripotent stem cell obtained by such a method. The fusion protein can be the fusion of an unrelated/heterologous transactivation domain and a transcription factor (e.g., the TAD is not normally associated with the transcription factor), such as the transactivation domain of MyoD (sequence information for MyoD is provided, for example, at NM_002478.4; NM_010866.2; NP_002469.2; NP_034996.2) or VP16 fused with Oct4 (full length or a bioactive fragment thereof; octamer-binding transcription factor 4 also known as POU5F1 (POU domain, class 5, transcription factor 1); sequence includes, for example, NM_002701; NM_013633.2; NP_002692; NP_038661.2; NM_001009178; NP_001009178; NM_131112; NP_571187). Additional trans-activating domains can include, for example, but are not limited to, those found in p53, VP16, MLL, E2A, HSF1, NF-IL6, NFAT1 and NF-κB.

Additional factors to be introduced into the cell, and/or used to generate a fusion protein with a transactivation domain, can include, but is not limited to, a gene from the Sox family (e.g., SOX genes encode a family of transcription factors that bind to the minor groove in DNA, and belong to a super-family of genes characterized by a homologous sequence called the HMG (high mobility group) box and include, but are not limited to, SoxA, SRY (e.g., NM_003140.1; NM_011564; NP_003131.1; NP_035694), SoxB1, Sox1 (e.g., NM_005986), Sox2 (e.g., NM_003106; NM_011443; NP_003097; NP_035573), Sox3 (e.g., NM_005634; XM_988206; NP_005625; XP_993300), SoxB2, Sox14 (e.g., NM_004189; XM_284529; NP_004180; XP_284529), Sox21 (e.g., NM_007084; XM_979432; NP_009015; XP_984526), SoxC, Sox4 (e.g., NM_003107; NM_009238; NP_003098; NP_033264), Sox11 (e.g., XM_001128542; NM_009234; XP_001128542; NP_033260), Sox12 (e.g., NM_006943; XM_973626; NP_008874; XP_978720), SoxD, Sox5 (e.g., NM_006940; NM_011444; NP_008871; NP_035574), Sox6 (e.g., NM_017508; NM_001025560; NP_059978; NP_001020731), Sox13 (e.g., NM_005686; NM_011439; NP_005677; NP_035569), SoxE, Sox8 (e.g., NM_014587; NM_011447; NP_055402; NP_035577), Sox9 (e.g., NM_000346; NM_011448; NP_000337; NP_035578), Sox10 (e.g., NM_006941; XM_001001494; NP_008872; XP_001001494), SoxF, Sox7, Sox17, Sox18 (e.g., NM_018419; NM_009236; NP_060889; NP_033262), SoxG, Sox15 (e.g., NM_006942; NM_009235; NP_008873; NP_033261), SoxH, Sox30), the Klf (Krueppel-like factor) family (e.g., KLF1 (e.g., NM_006563), KLF2 (e.g., NM_016270; XM_982078; NP_057354; XP_987172), KLF3 (e.g., NM_016531; XM_994052; NP_057615; XP_999146), KLF4 (e.g., NM_004235; NM_010637; NP_004226; NP_034767), KLF5 (e.g., NM_001730; NM_009769; NP_001721; NP_033899), KLF6 (e.g., NM_001008490; NM_011803; NP_001008490; NP_035933), KLF7 (e.g., NM_003709; XM_992457; NP_003700; XP_997551), KLF8 (e.g., NM_007250; NM_173780; NP_009181; NP_776141), KLF9 (e.g., NM_001206; XM_988516; NP_001197; XP_993610), KLF10 (e.g., NM_001032282; NM_013692; NP_001027453; NP_038720), KLF11 (e.g., XM_001129527; NM_178357; XP_001129527; NP_848134), KLF12 (e.g., NM_016285; NM_010636; NP_057369; NP_034766), KLF13 (e.g., NM_015995; NM_021366; NP_057079; NP_067341), KLF14 (e.g., NM_138693; NM_001135093; NP_619638; NP_001128565), KLF15 (e.g., NM_014079; NM_023184; NP_054798; NP_075673), KLF16, KLF17 (e.g., NM_173484.3; NM_029416.2; NP_775755.3; NP_083692.2)), the Myc family (e.g., c-Myc (e.g., NM_002467.4; NM_010849; NP_002458.2; NP_034979)), nanog (e.g., NM_024865.2; NM_028016.2; NP_079141.2; NP_082292.1), Lin28 (e.g., NM_024674; NM_145833; NP_078950; NP_665832) or a combination thereof. Additionally, the cell can also be contacted with a cytokine, such as basic fibroblast growth factor (bFGF) and/or stem cell factor (SCF). In one embodiment, the somatic cell is further contacted with a DNA demethylation reagent.

One embodiment provides a somatic cell derived by inducing differentiation of an induced pluripotent stem cell as disclosed herein. One embodiment also provides a method for stem cell therapy comprising: (1) isolating and collecting a somatic cell from a subject; (2) inducing said somatic cell from the subject into an iPSC (3) inducing differentiation of said iPSCs, and (4) transplanting the differentiated cell from (3) into the subject (e.g., a mammal, such as a human).

Figure 1A:
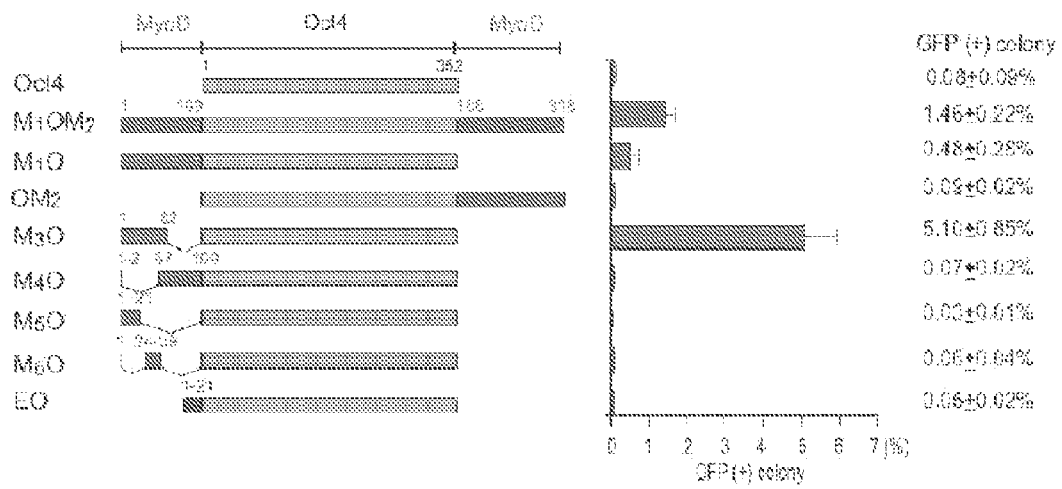
FIG. 1. Establishment of mouse iPSCs with $M_3$O-SKM. (A) Schematic drawing of MyoD-Oct4 chimeric constructs. Numbers indicate amino acid positions delimiting MyoD fragments. The basic helix-loop-helix (bHLH) domain of MyoD corresponds to amino acids 108-167, which was not used in these chimeric constructs. EO indicates a polypeptide consisting of one methionine and a chain of 20 glutamic acids fused to Oct4 (E for glutamic acid). Right column shows percentage of GFP-positive colonies derived from mouse embryonic fibroblasts (MEFs) transduced with each MyoD-Oct4 chimeric construct along with SKM and cultured on feeder cells (FIG. 1B, Protocol A). Data represent the mean±SEM from three independent experiments. (B) Schematic drawings of two protocols for iPSC creation. Whereas transduced MEFs were transferred onto feeder cells on day 4 in Protocol A, MEFs were maintained feeder-free until the end of experiments in Protocol B. (C) Emergence of GFP-positive colonies obtained with $M_3$O-SKM with Protocol B. Bar, 200 μm. (D) Summary of the efficiency of making GFP-positive colonies with various combinations of the $M_3$O, Sox2, Klf4, and c-Myc genes with Protocol B. Number of GFP-positive colonies peaked by day 14. (E) Drawings of various combinations of the $M_3$ domain and Oct4. The efficiency of making GFP-positive colonies with Protocol B in the presence of SKM is shown on the right. (F) Drawings of TAD replacement constructs in which TADs of Oct4 were replaced with the $M_3$ domain. Constructs were transduced with SKM. (G) Drawings of fusion constructs between the $M_3$ domain and Sox2 or Klf4. Sox2 mutants were transduced with OKM or $M_3$O-KM. The Klf4 mutant was transduced with OSM or $M_3$O-SM. (H) Drawings of fusion constructs between Oct4 and TADs taken from other transactivators. Constructs were transduced with SKM.

DETAILED DESCRIPTION OF THE INVENTION iPSC technology is the process of converting an adult specialized cell, such as a skin cell, into a stem cell, a process known as dedifferentiation. iPSCs can be very useful in clinical as well as preclinical settings. For example, iPSCs can be created from human patients and differentiated into many tissues to provide new materials for autologous transplantation, which can avoid immune rejection of the transplanted tissues. For example, pancreatic beta cells differentiated from a patient's iPSCs can be transplanted into the original patient to treat diabetes. Also, iPSCs derived from a patient can be differentiated into the ailing tissue to be used in an in vitro disease model. For example, study of dopaninergic neurons differentiated from a Parkinson's disease patient can provide unprecedented clues for the pathogenesis of the disease. In vitro-differentiated cells derived from iPSCs can be used for drug screening. For instance, many drugs are metabolized in the liver, but there have been no ideal liver cells that can be cultured for a long term for in vitro screening of drug toxicity. Also, iPSCs provide a new opportunity to understand the mechanisms underlying the plasticity of cell differentiation. Thus, the potential of iPSCs for many fields of life science is tremendous.

However, the process of generating iPSCs is slow and inefficient. With the standard protocol, MEFs are transduced with OSKM on day 1 and the cells are transferred onto feeder cells composed of irradiated fibroblasts, which provide a poorly characterized, but optimal environment for the generation of iPSCs, on day 5. iPSC colonies emerge around day 10, which are then picked up and expanded over the next two to three weeks on feeder cells to establish purified iPSC lines. Eventually, only 0.1% of the transduced fibroblasts turn into iPSCs. This slow process and extremely low efficiency make production of iPSCs costly.

It is disclosed herein that a fusion protein combining, for example, the stem cell factor Oct4 (a homeodomain transcription factor associated with undifferentiated cells) with a portion of another protein factor, for example, a transactivation domain, such as that of MyoD, can accelerate the process of making iPSCs. It is also shown herein that heterologous transactivation domains, including the MyoD TAD, promote global chromatin remodeling of stem cell genes. Thus, the process disclosed herein improves the efficiency and quality of iPSCs.

DEFINITIONS

As used herein, the terms below are defined by the following meanings:

Induced pluripotent stem cells, commonly abbreviated as iPSCs, are a type of pluripotent stem cell obtained from a non-pluripotent cell, typically an adult somatic cell (a cell of the body, rather than gametes or an embryo), by inducing a "forced" expression of certain genes. iPSCs are believed to be similar to natural pluripotent stem cells, such as ESCs in many respects, such as the expression of certain stem cell genes and proteins, chromatin methylation patterns, doubling time, embryoid body formation, teratoma formation, viable chimera formation, and potency and differentiability.

iPSCs are not adult stem cells, but rather reprogrammed cells (e.g., epithelial cells) given pluripotent capabilities. Using genetic reprogramming with protein transcription factors, pluripotent stem cells equivalent to embryonic stem cells have been derived from human adult skin tissue. Shinya Yamanaka and his colleagues at Kyoto University used the transcription factors Oct3/4, Sox2, c-Myc, and Klf4 in their experiments on cells from humans. Junying Yu, James Thomson, and their colleagues at the University of Wisconsin—Madison used a different set of factors, Oct4, Sox2, Nanog and Lin28, and carried out their experiments using cells from human foreskin to generate iPS cells.

The term "isolated" refers to a factor(s), cell or cells which are not associated with one or more factors, cells or one or more cellular components that are associated with the factor(s), cell or cells in vivo.

"Cells" include cells from, or the "subject" is, a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, orangutan), rat, sheep, goat, cow and bird.

An "effective amount" generally means an amount which provides the desired local or systemic effect and/or performance.

"Pluripotency" refers to a stem cell that has the potential to differentiate into one, two or three of the three germ layers: endoderm (e.g., interior stomach lining, gastrointestinal tract, the lungs), mesoderm (e.g., muscle, bone, blood, urogenital), or ectoderm (e.g., epidermal tissues and nervous system). Pluripotent stem cells can give rise to any fetal or adult cell type.

"Transdifferentiation" is when a non-stem cell transforms into a different type of cell, or when an already differentiated stem cell creates cells outside its already established differentiation path.

A "transcription factor" (sometimes called a sequence-specific DNA-binding factor) is a protein that binds to specific DNA sequences, thereby controlling the transfer (or transcription) of genetic information from DNA to mRNA. Transcription factors perform this function alone or with other proteins or factors in a complex, by promoting (as an activator), or blocking (as a repressor) the recruitment of RNA polymerase (the enzyme that performs the transcription of genetic information from DNA to RNA) to specific genes. Generally, a defining feature of transcription factors is that they contain one or more DNA-binding domains (DBDs), which attach to specific sequences of DNA adjacent to the genes that they regulate.

A "transcription activation domain," "transactivation domain" or "trans-activating domain" is generally that portion of a transcription factor that is responsible for recruitment of the transcription machinery needed to transcribe RNA. Transactivation is an increased rate of gene expression triggered either by biological processes or by artificial means. Transactivation can be triggered either by endogenous cellular or viral proteins—transactivators. These protein factors act in trans (i.e., intermolecularly). An "unrelated" or "heterologous transactivation domain" refers to a transactivation domain that is not normally associated with the gene/protein (e.g., transcription factor) of interest (not wild-type).

By "pure" it is meant that the population of cells has the desired purity. For example, iPSC populations can comprise mixed populations of cells. Those skilled in the art can readily determine the percentage of iPSCs in a population using various well-known methods, such as fluorescence activated cell sorting (FACS). Preferable ranges of purity in populations comprising iPSCs are about 1 to about 5%, about 5 to about 10%, about 10 to about 15%, about 15 to about 20%, about 20 to about 25%, about 25 to about 30%, about 30 to about 35%, about 35 to about 40%, about 40 to about 45%, about 45 to about 50%, about 50 to about 55%, about 55 to about 60%, about 60 to about 65%, about 65 to about 70%, about 70 to about 75%, about 75 to about 80%, about 80 to about 85%, about 85 to about 90%, about 90% to about 95% or about 95 to about 100%. Purity of the cells can be determined for example according to the cell surface marker profile within a population.

The terms "comprises," "comprising," and the like can have the meaning ascribed to them in U.S. Patent Law and can mean "includes," "including" and the like. As used herein, "including" or "includes" or the like means including, without limitation.

Rapid and Efficient Production of iPSCs

Through the processes disclosed herein, iPSC colonies emerge as early as about five days (day 5) after transduction of a transactivator domain (or a portion thereof) fused to a transcription factor (or a portion thereof), e.g., $M_3O$ (short transactivation domain of MyoD (about 50 to 60 amino acids) fused to the amino terminus of the full-length Oct4), Sox2, Klf4, and c-Myc without feeder cells. The preparation of the nucleic acid molecule coding for the fusion protein(s) as well as the construct(s) of Sox, Klf, c-Myc etc. (either singly or on a polycistronic RNA) can be carried out by methods available to an art worker as well as the transduction thereof into cells (see, for example, Sambrook, Molecular Cloning: A Laboratory Manual).

iPSCs established with the standard OSKM protocol frequently contain partially reprogrammed cells and even established iPSCs occasionally lose pluripotency during prolonged cultures. In contrast, the iPSCs disclosed herein retain pluripotency more tightly and heterogeneity among different colonies is much less apparent than that with the OSKM iPSCs. In addition, iPSC colonies can be obtained without c-Myc (use only $M_3O$, Sox2 and Klf4) at the efficiency of 0.44% around day 7. iPSCs have been prepared without c-Myc (use OSK) before, but the efficiency was low (<0.01%) and it generally took 30 to 40 days for iPSCs to emerge[2,3]. Additionally, this transactivation domain-based strategy can be applied to amplify the effects of other transcription factors to facilitate their reprogramming capability of cell differentiation. In summary, the use of a TAD, such as the $M_3$ domain, has made iPSC production faster, easier, feeder-free and more efficient than the standard OSKM or other protocols.

Thus, as discussed above, the fusion technology, such as the $M_3O$, technology disclosed herein has significant advantages over wild-type Oct4 (or other transcription factors) in generating iPSCs. First, the fusion technology is faster. While iPSC colonies appear at about day 10 with the standard OSKM protocol (see, Cell Stem Cell 2008, 3, 595 for a general protocol for making iPSCs), iPSC colonies emerge on day 5 with the fusion technology (e.g., $M_3O$-SKM). Second, efficiency of making iPSCs is more than 50-fold higher with the fusions technology (e.g., $M_3O$-SKM) than that with OSKM. Third, purer iPSCs populations can be obtained with the fusions technology described herein (e.g., $M_3O$-SKM) compared with OSKM. Fourth, the fusion technology described herein (e.g., $M_3O$-SKM) does not require feeder cells unlike OSKM. This is noted especially for making iPSCs for transplantation purposes because one would generally need to use patient-derived fibroblasts as feeder cells to avoid immune rejection. Also, the use of feeder cells adds an extra step to make iPSCs. Feeder-free iPSCs have been reported, but they are derived from already undifferentiated cells, such as adipose stem cells. Fibroblasts generally require feeder cells to become iPSCs. Finally, iPSCs can be prepared using only $M_3O$, Sox2 and Klf4 (without c-Myc).

Generally, genes which can be used to create induced pluripotent stem cells, either singly, in combination or as fusions with transactivation domains, include, but are not limited to, one or more of the following: Oct4 (Oct3/4, Pou5f1), Sox (e.g., Sox1, Sox2, Sox3, Sox18, or Sox15), Klf (e.g., Klf4, Klf1, Klf3, Klf2 or Klf5), Myc (e.g., c-myc, N-myc or L-myc), nanog, or LIN28. As examples of sequences for these genes and proteins, the following accession numbers are provided: Mouse MyoD: M84918, NM_010866; Mouse Oct4 (POU5F1): NM_013633; Mouse Sox2: NM_011443; Mouse Klf4: NM_010637; Mouse c-Myc: NM_001177352, NM_001177353, NM_001177354; Mouse Nanog: NM_028016; Mouse Lin28: NM_145833; Human MyoD: NM_002478; Human Oct4 (POU5F1): NM_002701, NM_203289, NM_001173531; Human Sox2: NM_003106; Human Klf4: NM_004235; Human c-Myc: NM_002467; Human Nanog: NM_024865; and/or Human Lin28: NM_024674, for portions or fragments thereof and/ or any related sequence available to an art worker (these sequences are incorporated by referenced herein). For example, sequences for use in the invention have at least about 50% or about 60% or about 70%, about 71%, about 72%, about 73%, about 74%, about 75%, about 76%, about 77%, about 78%, or about 79%, or at least about 80%, about 81%, about 82%, about 83%, about 84%, about 85%, about 86%, about 87%, about 88%, or about 89%, or at least about 90%, about 91%, about 92%, about 93%, or about 94%, or at least about 95%, about 96%, about 97%, about 98%, or about 99% sequence identity compared to the sequences and/or accession numbers provided herein and/or any other such sequence available to an art worker, using one of alignment programs available in the art using standard parameters or hybridization techniques. In one embodiment, the differences in sequence are due to conservative amino acid changes. In another embodiment, the protein sequence or DNA sequence has at least 80% sequence identity with the sequences disclosed herein and is bioactive (e.g., retains activity).

Methods of alignment of sequences for comparison are available in the art. Thus, the determination of percent identity between any two sequences can be accomplished using a mathematical algorithm. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

During and after preparation of iPSCs, the cells can be cultured in culture medium that is established in the art and commercially available from the American Type Culture Collection (ATCC), Invitrogen and other companies. Such media include, but are not limited to, Dulbecco's Modified Eagle's Medium (DMEM), DMEM F12 medium, Eagle's Minimum Essential Medium, F-12K medium, Iscove's Modified Dulbecco's Medium, Knockout DMEM, or RPMI-1640 medium. It is within the skill of one in the art to modify or modulate concentrations of media and/or media supplements as needed for the cells used. It will also be apparent that many media are available as low-glucose formulations, with or without sodium pyruvate.

Also contemplated is supplementation of cell culture medium with mammalian sera. Sera often contain cellular factors and components that are needed for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, rat serum (RS), serum replacements (including, but not limited to, KnockOut Serum Replacement (KSR, Invitrogen)), and bovine embryonic fluid. It is understood that sera can be heat-inactivated at 55-65° C. if deemed needed to inactivate components of the complement cascade. Modulation of serum concentrations, or withdrawal of serum from the culture medium can also be used to promote survival of one or more desired cell types. In one embodiment, the cells are cultured in the presence of FBS/or serum specific for the species cell type. For example, cells can be isolated and/or expanded with total serum (e.g., FBS) or serum replacement concentrations of about 0.5% to about 5% or greater including about 5% to about 15% or greater, such as about 20%, about 25% or about 30%. Concentrations of serum can be determined empirically.

Additional supplements can also be used to supply the cells with trace elements for optimal growth and expansion. Such supplements include insulin, transferrin, sodium selenium, and combinations thereof. These components can be included in a salt solution such as, but not limited to, Hanks'

Balanced Salt Solution™ (HBSS), Earle's Salt Solution™, antioxidant supplements, MCDB-201™ supplements, phosphate buffered saline (PBS), N-2-hydroxyethylpiperazine-N'-ethanesulfonic acid (HEPES), nicotinamide, ascorbic acid and/or ascorbic acid-2-phosphate, as well as additional amino acids. Many cell culture media already contain amino acids; however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-inositol, L-isoleucine, L-leucine, L-lysine, L-methionine, L-phenylalanine, L-proline, L-serine, L-threonine, L-tryptophan, L-tyrosine, and L-valine.

Antibiotics are also typically used in cell culture to mitigate bacterial, mycoplasmal, and fungal contamination. Typically, antibiotics or anti-mycotic compounds used are mixtures of penicillin/streptomycin, but can also include, but are not limited to, amphotericin (Fungizone™), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Hormones can also be advantageously used in cell culture and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine. β-mercaptoethanol can also be supplemented in cell culture media.

Lipids and lipid carriers can also be used to supplement cell culture media, depending on the type of cell and the fate of the differentiated cell. Such lipids and carriers can include, but are not limited to cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulation.

Cells in culture can be maintained either in suspension or attached to a solid support, such as extracellular matrix components and synthetic or biopolymers. Cells often require additional factors that encourage their attachment to a solid support (e.g., attachment factors) such as type I, type II, and type IV collagen, concanavalin A, chondroitin sulfate, fibronectin, "superfibronectin" and/or fibronectin-like polymers, gelatin, laminin, poly-D and poly-L-lysine, Matrigel™, thrombospondin, and/or vitronectin.

Cells can be cultured at different densities, e.g., cells can be seeded or maintained in the culture dish at different densities. For example, for cells to be dedifferentiated or iPSCs, the cells can be seeded or maintained at low or high cell densities. For example, at densities, including, but not limited to, densities of less than about 2000 cells/well of a 12-well plate (for example, 12-well flat-bottom growth area: 3.8 cm$^2$ well volume: 6.0 ml or well ID×depth (mm) 22.1×17.5; well capacity (ml) 6.5, growth area (cm$^2$) 3.8), including less than about 1500 cells/well of a 12-well plate, less than about 1,000 cells/well of a 12-well plate, less than about 500 cells/well of a 12-well plate, or less than about 200 cells/well of a 12-well plate. The cells can also be seeded or maintained at higher densities, for example, great than about 2,000 cells/well of a 12-well plate, greater than about 2,500 cells/well of a 12-well plate, greater than about 3,000 cells/well of a 12-well plate, greater than about 3,500 cells/well of a 12-well plate, greater than about 4,000 cells/well of a 12-well plate, greater than about 4,500 cells/well of a 12-well plate, greater than about 5,000 cells/well of a 12-well plate, greater than about 5,500 cells/well of a 12-well plate, greater than about 6,000 cells/well of a 12-well plate, greater than about 6,500 cells/well of a 12-well plate, greater than about 7,000 cells/well of a 12-well plate, greater than about 7,500 cells/well of a 12-well plate or greater than about 8,000 cells/well of a 12-well plate.

The maintenance conditions of cells cultures can also contain cellular factors that allow cells, such as the iPSCs of the invention, to remain in an undifferentiated form. It may be advantageous under conditions where the cell must remain in an undifferentiated state of self-renewal for the medium to contain epidermal growth factor (EGF), platelet derived growth factor (PDGF), leukemia inhibitory factor (LIF), basic fibroblast growth factor (bFGF) and combinations thereof. It is apparent to those skilled in the art that supplements that allow the cell to self-renew (e.g., to produce replicate daughter cells having differentiation potential that is identical to those from which they arose; a similar term used in this context is "proliferation"), but not differentiate should be removed from the culture medium prior to differentiation. It is also apparent that not all cells will require these factors.

EXAMPLES

The following examples are provided in order to demonstrate and further illustrate certain embodiments and aspects of the present invention and are not to be construed as limiting the scope thereof.

Example 1

Materials and Methods

Preparation of Mouse iPSCs

Full-length and deletion mutants of mouse Oct4 cDNA were fused with various TADs and inserted into the pMXs-IP vector[4]. Polycistronic cDNAs encoding Sox2, Klf4 and c-Myc were transferred from the 4F2A lentiviral vector[5] to the pMXs-IP vector. pMXs-IP vectors encoding OSKM separately (Addgene) were also used in some experiments. These pMXs-IP vectors were transfected into Plat-E cells[6] with Fugene 6 (Roche). Virus supernatant was harvested 48 and 72 hr later and filtered through a 0.45 μm syringe filter. MEFs were prepared from Oct4-GFP mice which harbour an IRES-green fluorescence protein (GFP) fusion cassette downstream of the stop codon of the Oct4 gene (Jackson Laboratory #008214)[7]. All animal experiments were conducted in accordance with the animal experiment guidelines of University of Minnesota. For chimera experiments, MEFs were prepared from mice that harbour the Oct4-GFP allele and ROSA26-lacZ allele. MEFs were seeded at 3×10$^5$ cells/6 cm dish on day −2 in DMEM with 10% fetal bovine serum (FBS). Fresh virus supernatant was added to MEFs on day −1 and day 0 with 10 μg/ml polybrene. Culture medium was then changed to iPSC medium (DMEM, 15% fetal bovine serum, 100 μM MEM non-essential amino acids, 55 μM 2-mercaptoethanol, 2 mM L-glutamine and 1000 u/ml leukemia inhibitory factor) on day 1. Transduced MEFs were subcultured onto irradiated SNL feeder cells at 2×10$^5$ cells/6 cm dish on day 4 and maintained on the feeder cells in Protocol A. The maximum number of GFP-positive colonies obtained around day 18 was divided by 2×10$^5$ to obtain the efficiency of making iPSCs. In Protocol B, transduced MEFs were maintained without feeder cells.

GFP-positive colonies were picked up around day 10 to clone without feeder cells for pluripotency analyses. Retrovirus titer was measured using NIH3T3 cells as described[8]. All recombinant DNA research was conducted following the NIH guidelines.

Preparation of Human iPSCs

Full-length human OCT4 cDNA fused with the $M_3$ domain of human MYOD at the amino terminus was inserted into the pMXs-IP vector. pMXs-IP vectors encoding human $M_3$O, OCT4, SOX2, KLF4 and c-MYC (Addgene) were transfected into Plat-A cells (Cell Biolabs) with Lipofectamin 2000 (Invitrogen). Virus supernatant was harvested 48 and 72 hrs later (day −1 and 0, respectively below), filtered through a 0.45 μm syringe filter and transduced into dermal fibroblasts obtained from a 34-year-old Caucasian female (Cell Applications). On day −2, $2.7 \times 10^4$ fibroblasts were plated in each well of a 12-well plate in DMEM with 10% fetal bovine serum. Fresh virus supernatant was added to the fibroblasts on day −1 and day 0 with 10 μg/ml polybrene. On day 3 cells were harvested with trypsin and subcultured at $1.7 \times 10^4$ cells per well in 12-well plates coated with BD Matrigel hESC-qualified Matrix (BD Biosciences) in human iPSC medium (KnockOut DMEM/F-12 (Invitrogen), 20% Knockout Serum Replacement (Invitrogen), 1001.1M MEM non-essential amino acids, 1% insulin-transferrin-selenium (Invitrogen), 0.1 mM 2-mercaptoethanol, 2 mM L-glutamine and 4 ng/ml basic FGF). The medium was changed every other day.

Chromatin Accessibility to NsiI

One million cells were resuspended in ice-cold lysis buffer containing 0.1% NP40 and incubated on ice for 5 min as previously described[9]. Nuclei were isolated with centrifugation at 4,000×g for 5 min and digested with 200 u/ml NsiI for 2 hr at 37° C. DNA was purified and double-digested with MspI and BamHI, followed by Southern blotting using the radioactive probe shown in FIG. 5D.

Immunoblotting

MEFs were transduced with MyoD-Oct4 fusion genes and analyzed with immunoblotting five days after transduction. All antibodies are listed in supplemental Table 1. SuperSignal West Dura (Thermo Scientific) was used to detect chemiluminescence signal.

TABLE 1

Antibodies used in immunoblotting, immunofluorescence staining and ChIP

Immunoblotting (primary antibodies)

| Antigen | Manufacturer | Catalog # |
|---|---|---|
| Oct4 | Santa Cruz Biotechnology | sc-9081 |
| Histone H2A | IMAGENEX | IMG-358 |

Immunoblotting (secondary antibodies)

| Name | Manufacturer | Catalog # |
|---|---|---|
| Peroxidase-conjugated anti-rabbit IgG | Jackson ImmunoResearch | 211-032-171 |
| Peroxidase-conjugated anti-mouse IgG | Jackson ImmunoResearch | 115-035-174 |

Immunofluorescence staining (primary antibodies)

| Antigen | Manufacturer | Catalog # |
|---|---|---|
| Oct4 | Santa Cruz Biotechnology | sc-8628 |
| Nanog | Abcam | ab21624 |
| SSEA1 | R&D Systems | FAB2155P |
| SSEA4, Alexa Fluor 488-labeled | BD Biosciences | 560308 |
| TRA-1-60, Alexa Fluor 555-labeled | BD Biosciences | 560121 |
| TRA-1-81, phycoerythrin-labeled | BD Biosciences | 560161 |

Immunofluorescence staining (secondary antibodies)

| Name | Manufacturer | Catalo g# |
|---|---|---|
| PE-labeled anti-mouse Ig(M + G) | BD Biosciences | 550589 |
| Alexa Fluor 555-labeled anti-rabbit IgG | Invitrogen | A21429 |
| Alexa Fluor 488-labeled anti-goat IgG | Invitrogen | A11055 |

ChIP

| Antigen | Manufacturer | Catalog # |
|---|---|---|
| Oct4 | Santa Cruz Biotechnology | sc-9081 |
| Sox2 | Santa Cruz Biotechnology | sc-17320 |
| Parafibromin | Bethyl Laboratories | A300-170A |
| Paf1 | Abcam | ab-20662 |
| Leo1 | Abcam | ab-70630 |
| H3K4me3 | Abcam | ab-1012 |
| H3K9ac | Abcam | ab-4441 |
| H3K14ac | Millipore | 07-353 |
| H3K9me3 | Millipore | 07-523 |
| H3K27me3 | Millipore | 07-449 |
| Control IgG | Santa Cruz Biotechnology | sc-2027 |

Fluorescence Microscopy iPSCs were fixed with 4% formaldehyde for 10 min and permeabilized with 0.5% Triton X-100 for 3 min. Cells were then incubated with primary antibody and secondary antibody for 1 hr each at 25° C. DNA was counterstained with Hoechst 33342. Used antibodies are listed in Table 1. Fluorescence signal was captured with a 10×A-Plan Ph1 Var1 objective (numerical aperture 0.25) and an AxioCam charge coupled device camera attached to an Axiovert 200M fluorescence microscope (all from Zeiss). Photoshop 7.0 (Adobe Systems) was used for image processing.

Alkaline Phosphatase Staining

Alkaline phosphatase was detected with an Alkaline Phosphatase Detection Kit (Millipore SCR004).

Flow Cytometry

The percentage of GFP-positive or SSEA1-positive cells at each time point was determined with a FACSCalibur flow cytometer and analyzed using CellQuest Pro software (both BD Biosciences).

Quantitative RT-PCR (qRT-PCR)

cDNA for mRNA was prepared from iPSC colonies using a Cells-to-cDNA II kit (Ambion). qRT-PCR was performed with GoTaq qPCR Master mix (Promega) on a Realplex 2S system (Eppendorf). PCR primer sequences are listed in Table 2. Expression level of glyceraldehyde 3-phosphate dehydrogenase (GAPDH) was used to normalize the expression levels of mRNAs. The feeder-free ESC line CGR8.8 was used as a positive control.

| Gene | Forward | Reverse |
|---|---|---|
| \multicolumn{3}{c}{Primers used for quantitative RT-PCR, bisulfite sequencing and ChIP} |
| \multicolumn{3}{c}{Quantitative RT-PCR (mouse)} |
| Oct4 endogenous | TCTTTCCACCAGGCCCCCGGCTC (SEQ ID NO: 36) | TGCGGGCGGACATGGGGAGATCC (SEQ ID NO: 37) |
| Sox2 endogenous | AAAGGAGAGAAGTTTGGAGCCCGA (SEQ ID NO: 38) | GGGCGAAGTGCAATTGGGATGAAA (SEQ ID NO: 39) |
| Nanog | AGCAGAAGATGCGGACTGTGTTCT (SEQ ID NO: 40) | CCGCTTGCACTTCATCCTTTGGTT (SEQ ID NO: 41) |
| Thy1 | GCCTGACCCGAGAGAAGAAGAAG (SEQ ID NO: 42) | TGGTGGTGAAGTTCGCTAGAGTAAG (SEQ ID NO: 43) |
| Col6a2 | CCACCACTGAAAGGAACAACAA (SEQ ID NO: 44) | TCCAACACGAAATACACGTTGAC (SEQ ID NO: 45) |
| Fgf7 | CCATGAACAAGGAAGGGAAA (SEQ ID NO: 46) | TCCGCTGTGTGTCCATTTAG (SEQ ID NO: 47) |
| GAPDH | TGCACCACCAACTGCTTAG (SEQ ID NO: 48) | GATGCAGGGATGATGTTC (SEQ ID NO: 49) |
| \multicolumn{3}{c}{Quantitative RT-PCR (human)} |
| OCT4 endogenous | CCTCACTTCACTGCACTGTA (SEQ ID NO: 50) | CAGGTTTTCTTTCCCTAGCT (SEQ ID NO: 51) |
| SOX2 endogenous | CCCAGCAGACTTCACATGT (SEQ ID NO: 52) | CCTCCCATTTCCCTCGTTTT (SEQ ID NO: 53) |
| KLF4 endogenous | GATGAACTGACCAGGCACTA (SEQ ID NO: 54) | GTGGGTCATATCCACTGTCT (SEQ ID NO: 55) |
| c-MYC endo. | TGCCTCAAATTGGACTTTGG (SEQ ID NO: 56) | GATTGAAATTCTGTGTAACTGC (SEQ ID NO: 57) |
| NANOG | TGAACCTCAGCTACAAACAG (SEQ ID NO: 58) | TGGTGGTAGGAAGAGTAAAG (SEQ ID NO: 59) |
| LIN28 | GAGCATGCAGAAGCGCAGATCAAA (SEQ ID NO: 60) | TATGGCTGATGCTCTGGCAGAAGT (SEQ ID NO: 61) |
| DPPA2 | AGGCTTCATAGGCATGCTTACCCT (SEQ ID NO: 62) | TGAAGCCTTGCTCTCTTGGTCACT (SEQ ID NO: 63) |
| DPPA4 | AGACACAGATGGTTGGGTTCACCT (SEQ ID NO: 64) | TGCACTCACTCTCCCTTCTTGCTT (SEQ ID NO: 65) |
| GDF3 | ACACCTGTGCCAGACTAAGATGCT (SEQ ID NO: 66) | TGACGGTGGCAGAGGTTCTTACAA (SEQ ID NO: 67) |
| REX1 | TGAATAGCTGACCACCAGCACACT (SEQ ID NO: 68) | ACAGGCTCCAGCCTCAGTACATTT (SEQ ID NO: 69) |
| TERT | TGTGCACCAACATCTACAAG (SEQ ID NO: 70) | GCGTTCTTGGCTTTCAGGAT (SEQ ID NO: 71) |
| TDGF1 | TGCCCAAGAAGTGTTCCCTGTGTA (SEQ ID NO: 72) | AAAGTGGTAGTACGTGCAGACGGT (SEQ ID NO: 73) |
| GAPDH | AACAGCGACACCCACTCCTC (SEQ ID NO: 74) | CATACCAGGAAATGAGCTTGACAA (SEQ ID NO: 75) |
| \multicolumn{3}{c}{Bisulfite sequencing} |
| Oct4 | AGGTTGAAAATGAAGGTTTTTT (SEQ ID NO: 76) | TCCAACCCTACTAACCCATCACC (SEQ ID NO: 77) |
| Oct4 Region 1 | GGAACTGGGTGTGGGGAGGTTGTA (SEQ ID NO: 78) | AGCAGATTAAGGAAGGGCTAGGACGAGAG (SEQ ID NO: 79) |
| Oct4 Region 2 | AGGTCAAGGGGCTAGAGGGTGGGATT (SEQ ID NO: 80) | TGAGAAGGCGAAGTCTGAAGCCA (SEQ ID NO: 81) |
| Oct4 Region 3 | TAGGAGCTCTTGTTTGGGCCATGT (SEQ ID NO: 82) | ACAAGGGTCTGCTCGTGTAAAGGT (SEQ ID NO: 83) |

| Primers used for quantitative RT-PCR, bisulfite sequencing and ChIP | | |
|---|---|---|
| Gene | Forward | Reverse |
| Sox2 Region 1 | TTTTGGTTTTTAGGGTAAGGTACTGGGAAG (SEQ ID NO: 84) | CCACGTGAATAATCCTATATGCATCACAAT (SEQ ID NO: 85) |
| Sox2 Region 2 | CACATGAAGGAGCACCCGGATTAT (SEQ ID NO: 86) | TCCGGGAAGCGTGTACTTATCCTT (SEQ ID NO: 87) |

DNA Microarray Analysis

RNA was prepared from CGR8.8 cells, MEFs, and a mouse iPSC clone prepared with the fusion gene between the $M_3$ domain of MyoD and Oct4 ($M_3$O-iPSC) on day 60 with the PureLink RNA total RNA purification system (Invitrogen). RNA was amplified and labeled using the Agilent Quick AmpLabeling Kit (Agilent Technologies) following the manufacturer's protocol. cRNA was hybridized overnight to Agilent Whole Murine Genome Oligo Microarray using the Agilent Gene Expression Hybridization Kit. The fluorescence signals of the hybridized microarrays were detected using Agilent's DNA Microarray Scanner. The Agilent Feature Extraction Software was used to read out and process the image files. Data were processed and visualized with Spotfire DecisionSite for Functional Genomics software. DNA microarray data have been deposited in the NCBI GEO database under the accession number GSE22327.

Karyotyping of Human iPSCs

Adherent cells were arrested with colcemid, harvested, treated with 75 mM KCl hypotonic solution, and fixed with methanol and acetic acid at 3:1. The cells were spread onto glass slides and stained with Wright-Giemsa stain. G-banded metaphases were evaluated using an Olympus BX61 microscope outfitted with 10× and 100× objectives. Metaphase cells were imaged and karyotyped using Applied Spectral Imaging (ASI) software.

Aggregation Chimera and Teratoma Formation

Ten $M_3$O-iPSCs of a cloned line were transferred into a microdrop of KSOMaa solution (Millipore) with a zona-free 8-cell stage mouse embryo of the ICR strain (albino) after brief exposure to acidic Tyrode's solution (Millipore). Aggregated morula stage embryos at 2.5 days post coitum (dpc) that contained GFP-positive iPSCs were transferred into the uteri of 2.5 dpc pseudopregnant recipient mice. Embryos at 13.5 dpc were analyzed for chimera formation with X gal stain or for germline transmission with a fluorescence microscope. To prepare teratomas, one million cloned mouse or human $M_3$O-iPSCs were injected into the limb muscle of NOD/SCID mice. Teratomas were fixed with 10% formalin and embedded with paraffin after three weeks for mouse iPSCs and eight weeks for human iPSCs. Five-µm thick sections were stained with haematoxylin and eosin for histological analysis.

Chromatin Immunoprecipitation (ChIP)

ChIP was performed as described in the instruction of the EZ Magna ChIP G kit (Millipore). All antibodies are listed in Table 1. PCR primer sequences are listed in Table 2. PCR amplification levels were first normalized against the value obtained with control IgG. The normalized values with ESCs or MEFs were then defined as 1.0 depending on antibodies to obtain relative expression levels in other cells.

DNA Methylation Analysis

Genomic DNA from mouse iPSCs was treated with bisulfite with an EZ DNA Methylation-Gold kit (Zymo Research). The DNA sequence at the Oct4 proximal promoter region was amplified with PCR using the primers listed in Table 2 and cloned into the pCR2.1-TOPO vector (Invitrogen) for sequencing.

Results

Generation of Mouse iPSCs with Heterologous Transactivation Domains

Figure 1B:
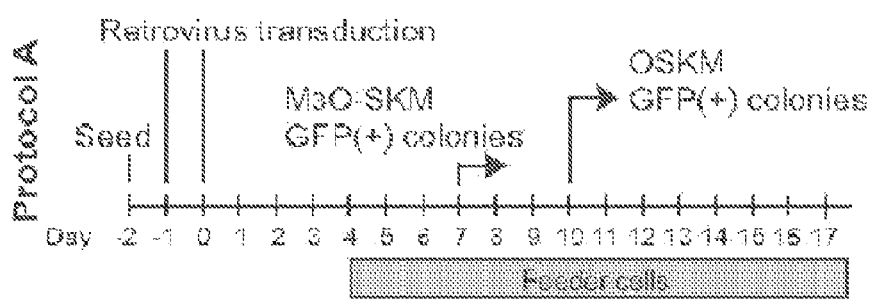
Figure 1B:
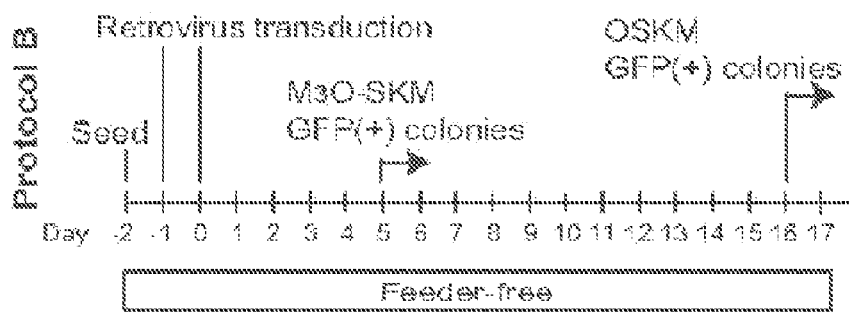
Figure 8:
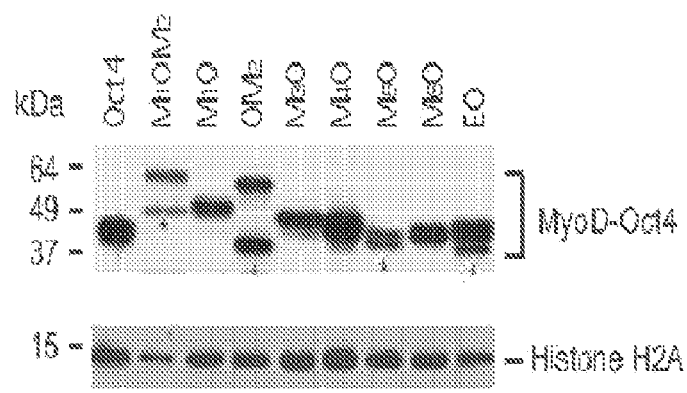
FIG. 8. Immunoblotting of MyoD-Oct4 fusion proteins. Expression of transduced MyoD-Oct4 fusion genes was evaluated with an antibody against Oct4 (top). Expression of histone H2A was examined as a loading control (bottom). Bands correspond to the predicted molecular mass of each protein. Identities of extra bands marked with asterisks are unknown.
Figure 9A:
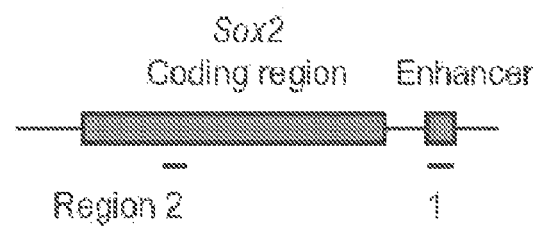
FIG. 9. ChIP analyses of the Sox2 gene. (A) Binding of Oct4 and Sox2 at the enhancer. (B) Binding of parafibromin and the levels of histone modifications associated with active genes on day 9. (C) Levels of histone modifications associated with suppressive genes on day 9.
Figure 9A:
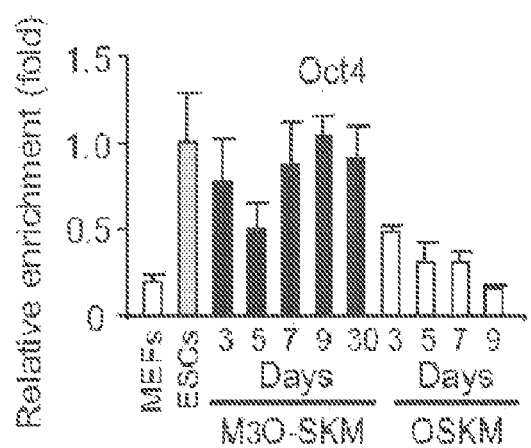
Figure 9A:
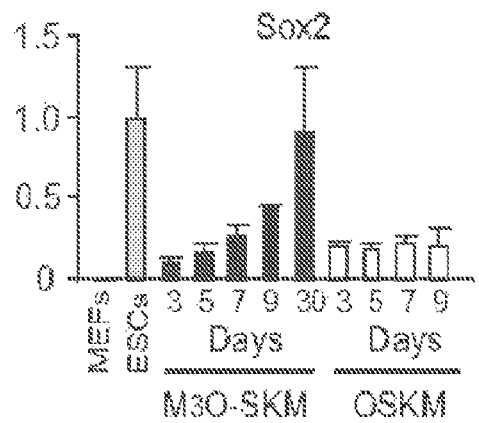
Figures 9B, 9C:
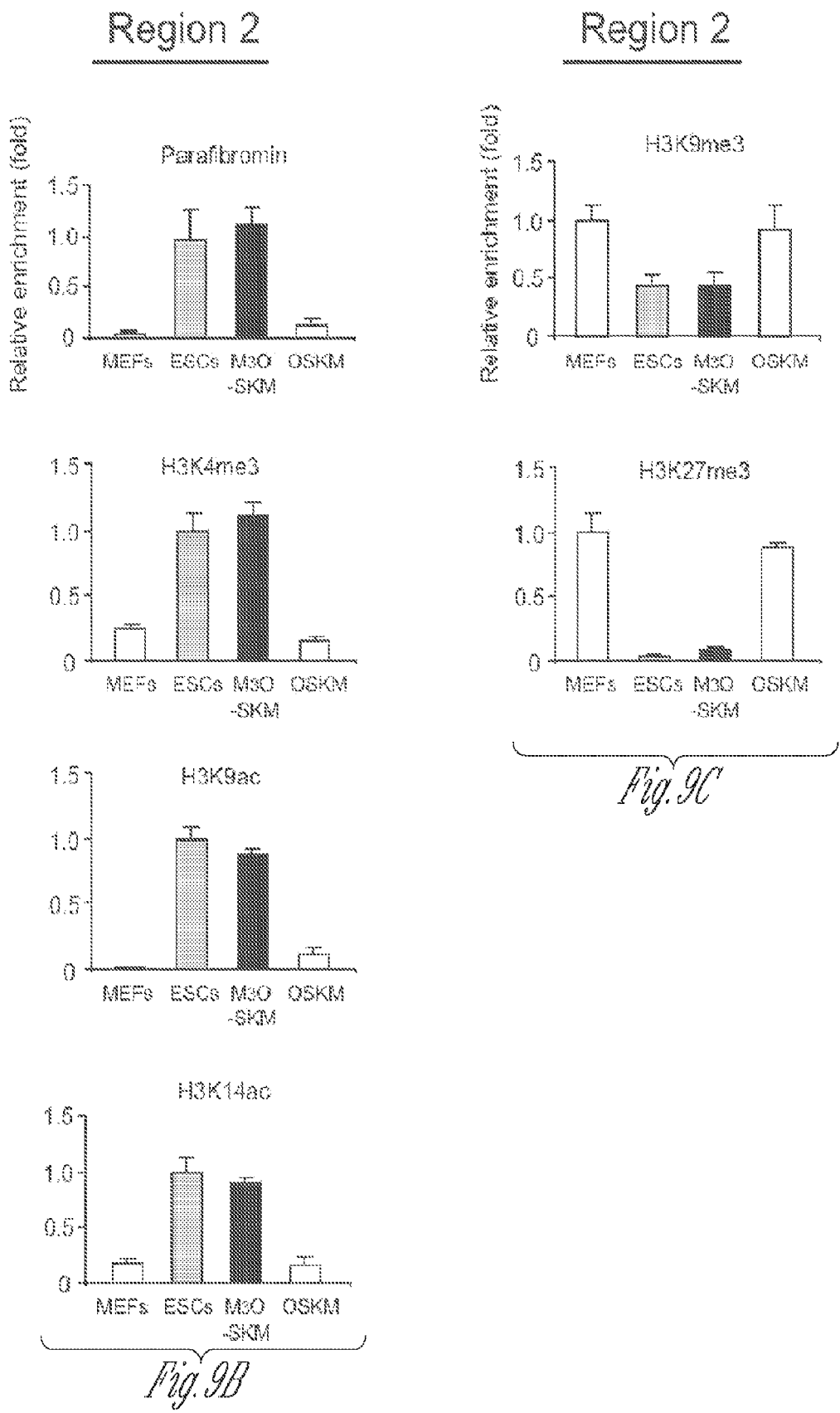

Full-length mouse Oct4 was fused with various fragments of mouse MyoD (FIG. 1A). The basic helix-loop-helix (bHLH) domain of MyoD, used for dimerization and DNA binding, was not included in these constructs to avoid activation of MyoD-target genes. Each chimeric gene was co-transduced with a polycistronic retroviral vector encoding mouse Sox2, Klf4, and c-Myc (SKM)[5] into MEFs derived from Oct4-GFP mice, which contain the GFP gene knocked into the Oct4 locus[7]. In this model, formation of GFP-positive colonies indicates that individual MEFs develop into Oct4-expressing cells capable of clonal growth. Expression of chimeric proteins was confirmed through immunoblotting with antibodies against Oct4 (FIG. 8). As a control, MEFs were transduced with OSKM (O-MEFs) on day −1 and 0 and transferred these cells onto SNL feeder cells on day 4 following a standard protocol (FIG. 1B, Protocol A). GFP-positive colonies emerged around day 10, gradually increasing in number until reaching a peak by day 18. To calculate the percentage of MEFs that were reprogrammed into iPSCs, the number of GFP-positive colonies were divided by the total number of MEFs seeded in a culture dish. It was estimated that 0.08±0.09% of O-MEFs were converted into GFP-positive cells, which is similar to previous reports[8,10] (FIG. 1A, right column). MEFs were then transduced with each chimeric gene along with SKM and followed the protocol described above (Protocol A). $M_3$O with SKM ($M_3$O-SKM) increased the percentage of GFP-positive colonies most drastically, with 5.10±0.85% of MEFs ($M_3$O-MEFs) being transformed into GFP-positive cells by day 15. The $M_3$ region encompasses the acidic transactivation domain (TAD) of MyoD (amino acids 3-56)[11]. However, the simple presence of acidity was insufficient to facilitate iPSC formation, as evidenced by a lack of increase in GFP-positive colonies in MEFs transduced with $M_6$O, which also contains the main acidic amino acid cluster, or a chain of 20 glutamic acids attached to Oct4 (EO) (FIG. 1A). The high efficiency with which $M_3$O created iPSCs as compared to Oct4 was not simply due to a difference in the retrovirus titer for the two virus suspensions. The titer for the $M_3$O virus and Oct4 virus was 1.8±0.2×10⁷ and 2.1±0.4×10⁷ colony forming units/ml, respectively.

While conducting the above experiments, it was noticed that GFP-positive colonies emerged from $M_3$O-MEFs on about day 5 without transfer onto feeder cells (FIG. 1B, Protocol B), and these colonies steadily increased in size and number (FIG. 1C). By around day 12, 3.6±0.5% of $M_3O$-MEFs formed GFP-positive colonies in the absence of feeder cells, perhaps supported by the surrounding MEFs serving as "autologous" feeder cells (FIG. 1D). In contrast, GFP-positive colonies emerged from O-MEFs between day 16 and 18 at an extremely low efficiency (0.0035±0.0006%) with the same protocol. It was next tested if GFP-positive colonies could be obtained without Sox2, Klf4, or c-Myc in the presence of $M_3O$ with Protocol B (FIG. 1D). Although $M_3O$ still required Sox2 and Klf4, c-Myc was dispensable. Previous studies have reported that iPSCs can be established without c-Myc[2,3]; however, the uniqueness of $M_3O$-SK lies in the speed and efficiency with which GFP-positive colonies form. While it requires three to four weeks and the presence of feeder cells for OSK to induce GFP-positive colonies at an efficiency of around 0.01%[2,3], $M_3O$-SK could generate GFP-positive colonies without feeder cells by day 7 after transduction at an efficiency of 0.44%, over 40-fold more efficient than OSK.

Figure 1F:
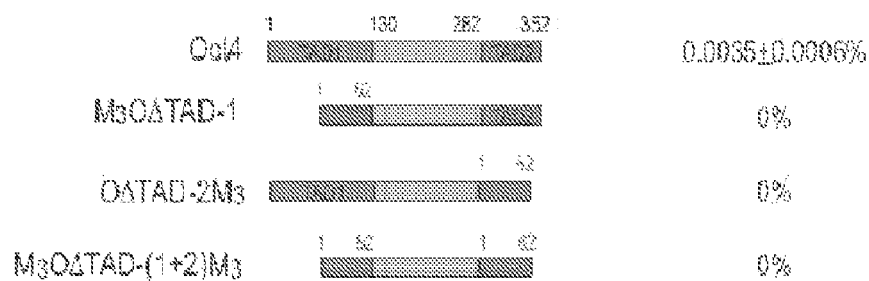
Figure 1G:
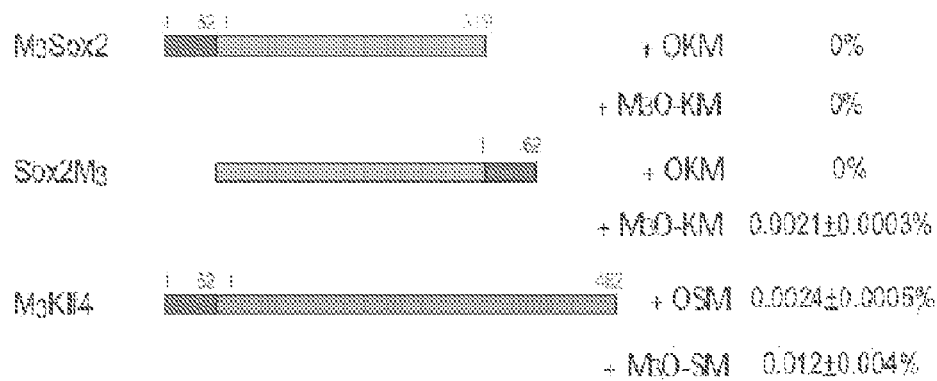
Figure 1H:
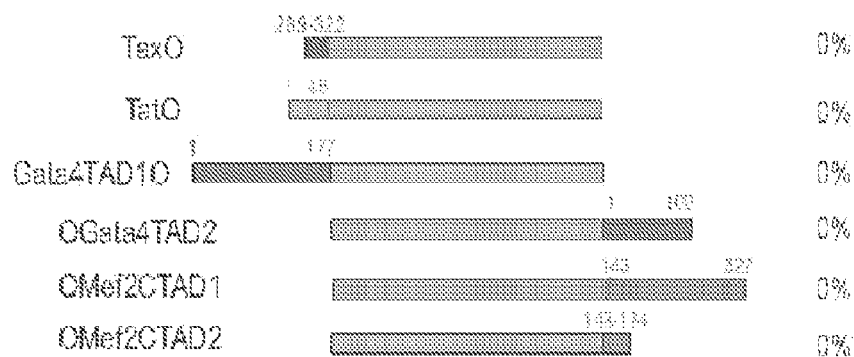

These striking differences between $M_3O$ and Oct4 prompted the evaluation of the specificity of the $M_3O$ configuration in relation to other host factors and TADs taken from other transcription factors using Protocol B. First, the location and number of the $M_3$ domains in the fusion protein with Oct4 were changed (FIG. 1E). Second, the two TADs in Oct4[12] were replaced with the $M_3$ domain in various combinations (FIG. 1F). Third, the $M_3$ domain was fused to Sox2 or Klf4 and tested in combination with other members of OSKM and $M_3O$ (FIG. 1G). $OM_3$ was as effective as $M_3O$ in iPSC creation. In a fourth experiment, TADs taken from other powerful transactivators were fused to Oct4 (FIG. 1H), including the TADs from Tax of human T-lymphotropic virus type 1 (HTLV-1)[13], Tat of human immunodeficiency virus type 1 (HIV-1)[14,15] Gata4[16,17] and Mef2c[17].

Characterization of $M_3O$-iPSCs

Figure 2A:
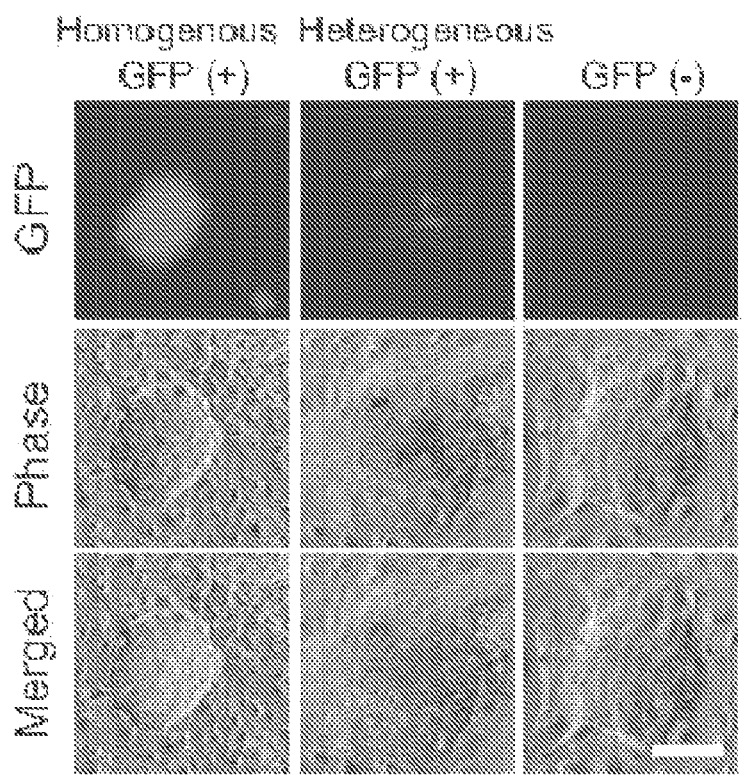
FIG. 2. Characterization of mouse iPSCs prepared with $M_3$O-SKM ($M_3$O-iPSCs). (A) Comparison of GFP-positivity between colonies obtained with $M_3$O-SKM and OSKM using Protocol B. Representative images of the GFP expression patterns used to categorize colonies are shown (top). Percentages of colonies with different GFP expression patterns were calculated from 300 colonies for $M_3$O-SKM and OSKM (bottom). Bar, 200 μm. (B) qRT-PCR analysis of expression levels of three pluripotency genes in MEFs and GFP-positive colonies obtained with $M_3$O-SKM and OSKM. PCR primers specific to endogenous Oct4 and Sox2 were used for these two genes. Although GFP-positive colonies were harvested on different days based on the time when the GFP signal first emerged for $M_3$O-SKM (day 5) and OSKM (day 10), the intervals between time points is equivalent (bottom of graphs). Expression level of each gene in ESCs (CGR8.8 cells) was defined as 1.0. Five colonies were examined for each condition. Results represent the mean±SEM of three independent experiments. (C) qRT-PCR analysis of expression levels of three fibroblast-enriched genes in MEFs and GFP-positive colonies obtained with $M_3$O-SKM and OSKM.

The GFP-positive colonies that emerged on day 5 following transduction with $M_3O$-SKM using Protocol B contained 31-143 cells in 12 colonies, with a median of 43 cells/colony. This number of cells would be produced after less than seven cell divisions assuming even division for each cell, which is strikingly small compared to the median of 70 cell divisions needed before GFP-positive cells appear with OSKM[18]. The colonies that emerged with $M_3O$-SKM were usually homogenously GFP-positive from the beginning. On day 7 over 97% of these colonies were homogeneously GFP-positive with Protocol B compared to around 5% of colonies derived with OSKM obtained on day 12 with Protocol A (FIG. 2A). Protocol A was used for OSKM. As a result, GFP-positive colonies were harvested at different time points corresponding to two days after the onset of GFP activation.

Figure 2B:
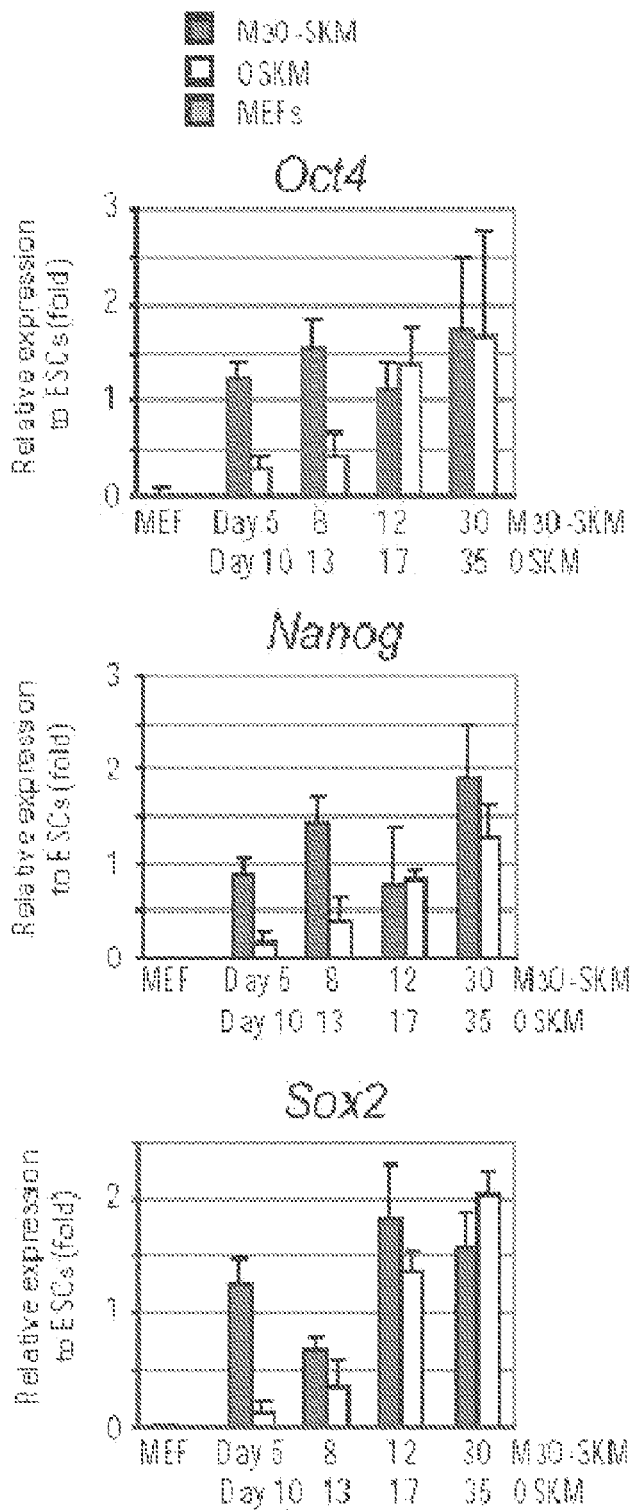
Figure 2C:
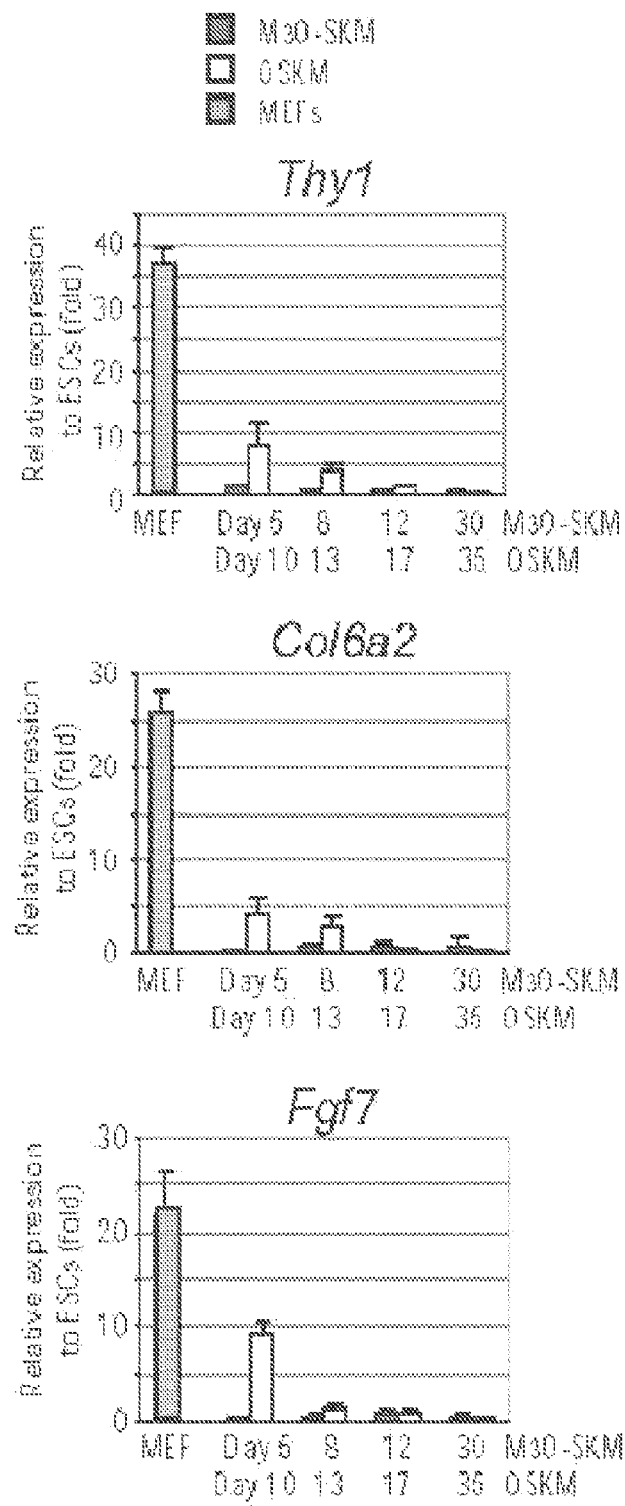

The quality of GFP-positive colonies obtained with $M_3O$-SKM and OSKM were compared by quantitative RT-PCR (qRT-PCR) analysis of three pluripotency genes (endogenous Oct4, endogenous Sox2, and Nanog) and three fibroblast-enriched genes (Thy1, Col6a2, and Fgf7)[19-21]. Homogeneously GFP-positive colonies obtained with $M_3O$-SKM using Protocol B and those with OSKM using Protocol A were selected to represent the colonies for each group. Although cells were harvested at different time points corresponding to the onset of GFP activation, the interval between time points is the same. For OSKM, expression of the three pluripotency genes gradually increased during the initial week after emergence of GFP-positive colonies, indicating a slow maturation process toward pluripotency (FIG. 2B). For $M_3O$-SKM, in contrast, levels of these transcripts reached or exceeded those seen in ESCs at the time of the emergence of GFP-positive colonies and remained at similar levels until day 30. This differential efficiency of transcriptional reprogramming was also evident with suppression of the three fibroblast-enriched genes. For $M_3O$-SKM, expression levels of these genes on day 5 when the GFP signal was apparent were comparable to those seen in ESCs, but it took around one week after the activation of GFP for OSKM to accomplish the same level of gene suppression (FIG. 2C). Together, these results indicate that $M_3O$-SKM can reprogram MEFs to an iPSC state more efficiently than OSKM.

Figure 3A:
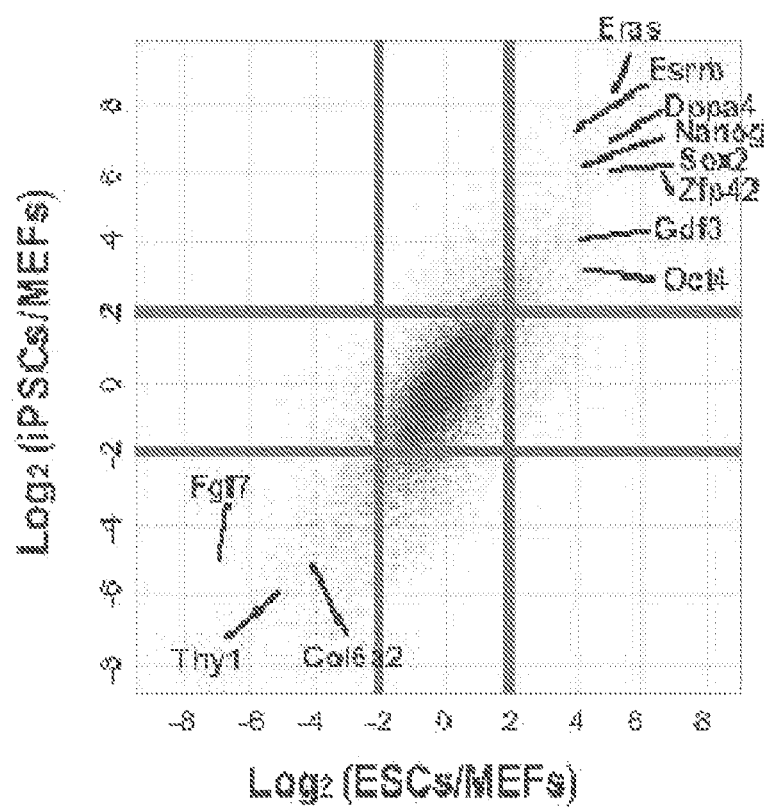
FIG. 3. Verification of pluripotency of mouse $M_3$O-iPSCs. (A) Expression level of transcripts in $M_3$O-iPSCs and ESCs relative to MEFs. Log 2 ratios are plotted for transcripts in ESCs/MEFs and iPSCs/MEFs. Red lines indicate a 4-fold difference in transcript levels. Transcripts in $M_3$O-iPSCs were assayed 60 days after transduction. (B) Hematoxylin and eosin staining of teratoma sections derived from $M_3$O-iPSCs. Neural tube and epidermis (ectoderm), striated muscle and bone (mesoderm), and mucous gland and respiratory epithelium (endoderm) are shown. Bar, 50 μm. (C) X gal staining for cells expressing the lacZ gene in a chimeric embryo prepared with $M_3$O-iPSCs and a control embryo at 13.5 dpc. (D) Chimeric mice prepared with $M_3$O-iPSCs. The agouti coat color indicates a high (right) and low (left) contribution of iPSCs to the skin. The host embryos used to generate mice were derived from the albino mouse strain ICR. (E) Germline contribution of $M_3$O-iPSCs as shown by GFP expression in the gonad of a 13.5 dpc chimeric embryo. (F) Pups obtained from crossing a wild-type ICR female (bottom) with an $M_3$O-iPSC chimeric male (left mouse in panel D).
Figure 3B:
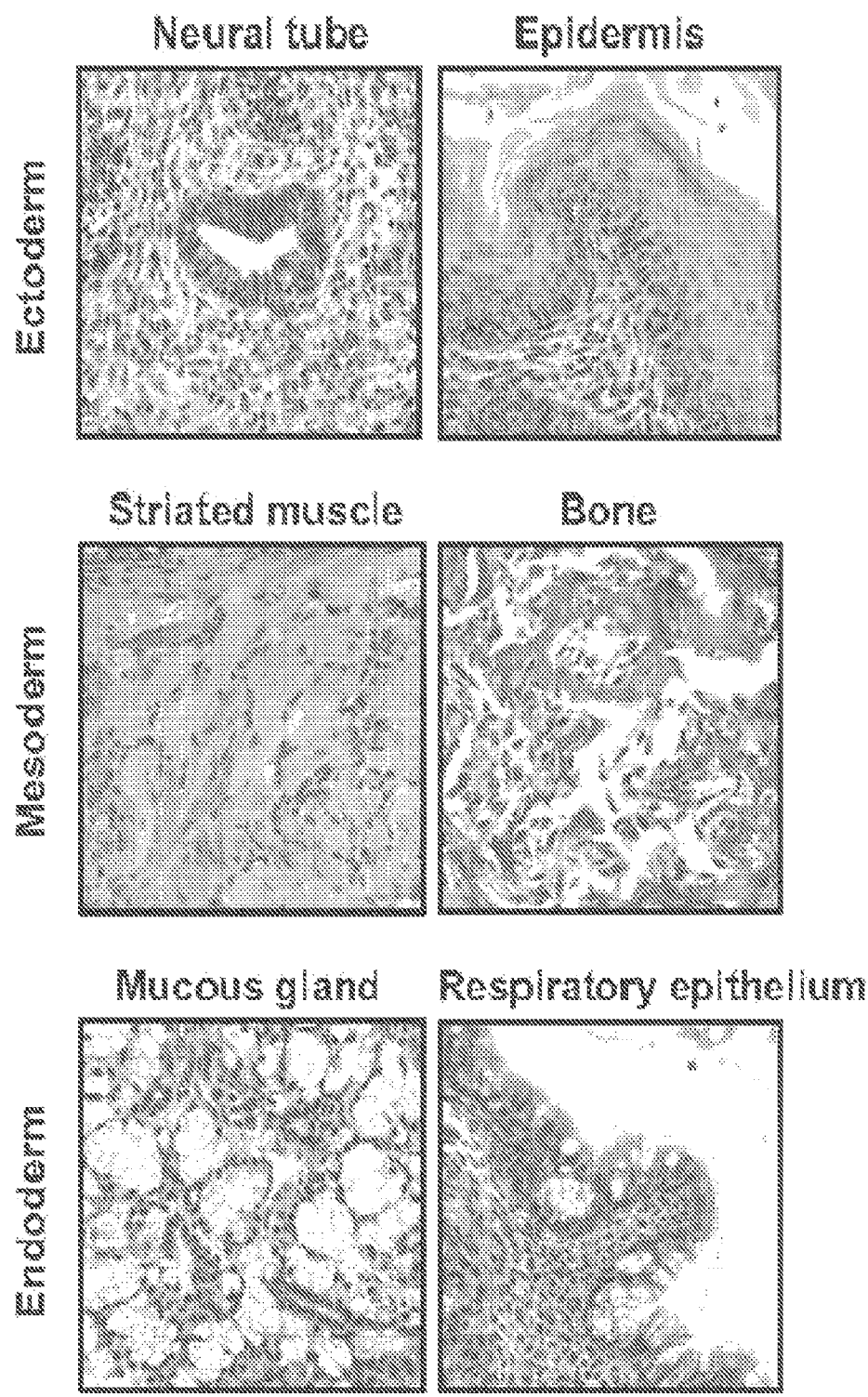
Figure 3D:
Figure 3F:
Figure 3C:
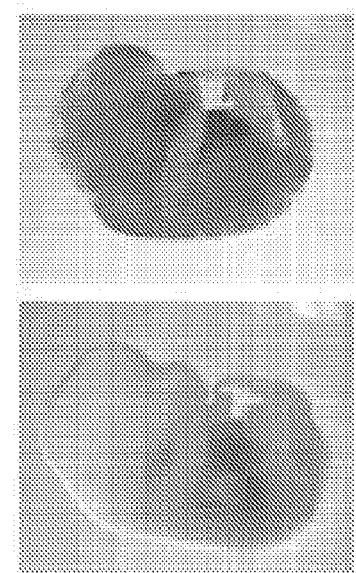
Figure 3E:
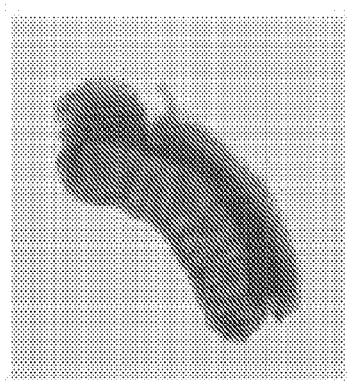

The pluripotency of iPSC clones prepared with $M_3O$-SKM following Protocol B ($M_3O$-iPSCs) was verified using three standard approaches. First, genome-wide transcript analysis demonstrated highly similar gene expression in $M_3O$-iPSCs and ESCs. Out of 41,160 probes, 3,293 were greater than 4-fold differentially expressed (up- or down-regulated) in both ESCs and cloned iPSCs compared to MEFs (FIG. 3A). The commonly up-regulated genes included eight ECS-enriched genes, such as Oct4, Sox2 and Nanog. In addition, Thy1, Col6a2 and Fgf7 were down-regulated more than 16-fold in both ESCs and iPSCs. Second, intramuscular injection of $M_3O$-iPSCs into an NOD/SCID mouse resulted in teratoma formation as shown by the presence of various tissues derived from the three germ layers (FIG. 3B). Third, aggregation of 8-cell stage embryos of the ICR strain with $M_3O$-iPSCs containing the Oct4-GFP allele and ROSA26-lacZ allele formed chimeric mice (FIG. 3C, 3D). $M_3O$-iPSCs contributed to germ cells in some chimeric mice (FIG. 3E). When one of the chimeric males (FIG. 3D left) was crossed with a wild-type female ICR mouse (FIG. 3F, white adult at bottom), all 11 pups showed agouti or black coat color (FIG. 3F).

Establishment of Human iPSCs with $M_3O$-SKM

Figure 4A:
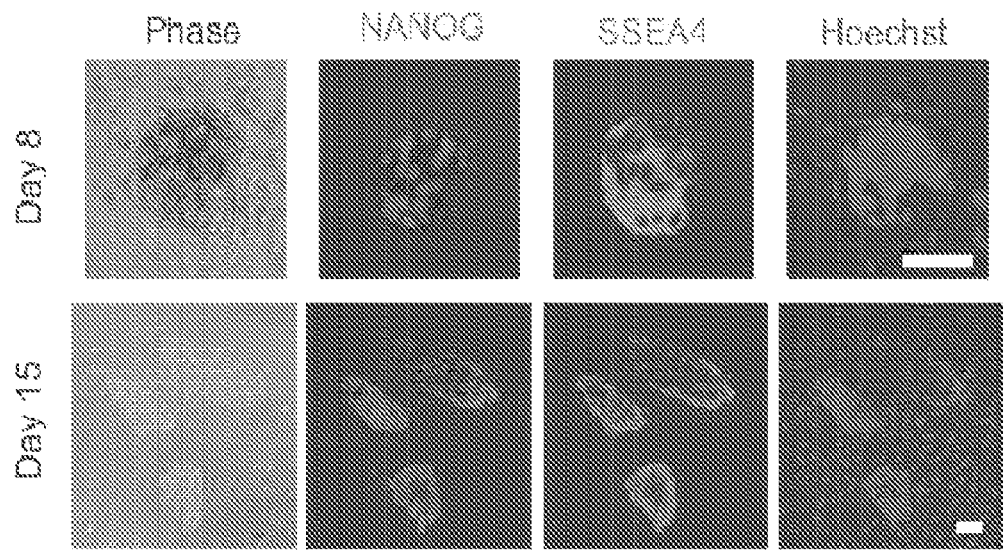
FIG. 4. Characterization of human iPSCs established with $M_3$O-SKM. (A) Immunofluorescence staining of NANOG and SSEA4 in human iPSC colonies on day 8 and 15 obtained with $M_3$O-SKM without subculture after day 3 when transferred onto Matrigel. Bar, 100 μm for (A) and (B). Note that day 15 colonies are substantially larger than day 8 colonies as indicated by the different magnifications. (B) Comparison of the efficiency of making NANOG-positive colonies between $M_3$O-SKM and OSKM. The number of NANOG-positive colonies was divided by the number of seeded dermal fibroblasts at each time point. (C) Immunofluorescence staining of pluripotency markers in cloned human iPSCs obtained with $M_3$O-SKM on day 28 after four passages. (D) Quantitative RT-PCR analysis of pluripotency genes expressed in cloned human iPSCs prepared with $M_3O$-SKM. Ten colonies were harvested on day 30 and the mean±SEM was obtained. The expression level of each gene in human ESCs H9 was defined as 1.0. Endogenous genes were amplified for OCT4, SOX2, KLF4 and c-MYC. (E) Karyotype analysis of a human iPSC established with $M_3O$-SKM. (F) Hematoxylin and eosin staining of teratoma sections derived from human iPSCs prepared with $M_3O$-SKM. Bar, 100 μm.
Figure 4B:
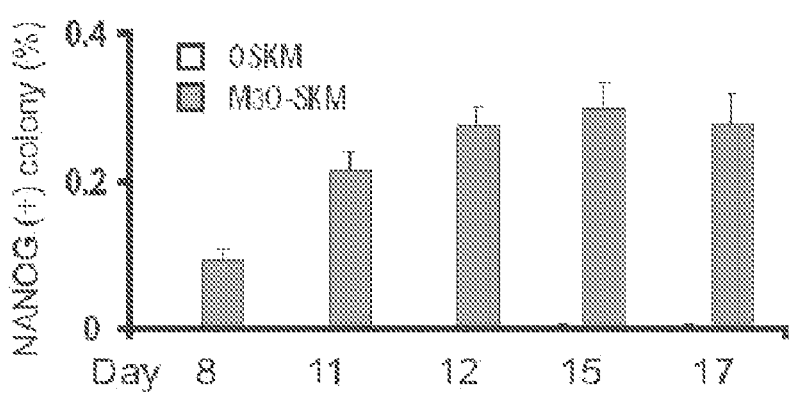
Figure 4C:
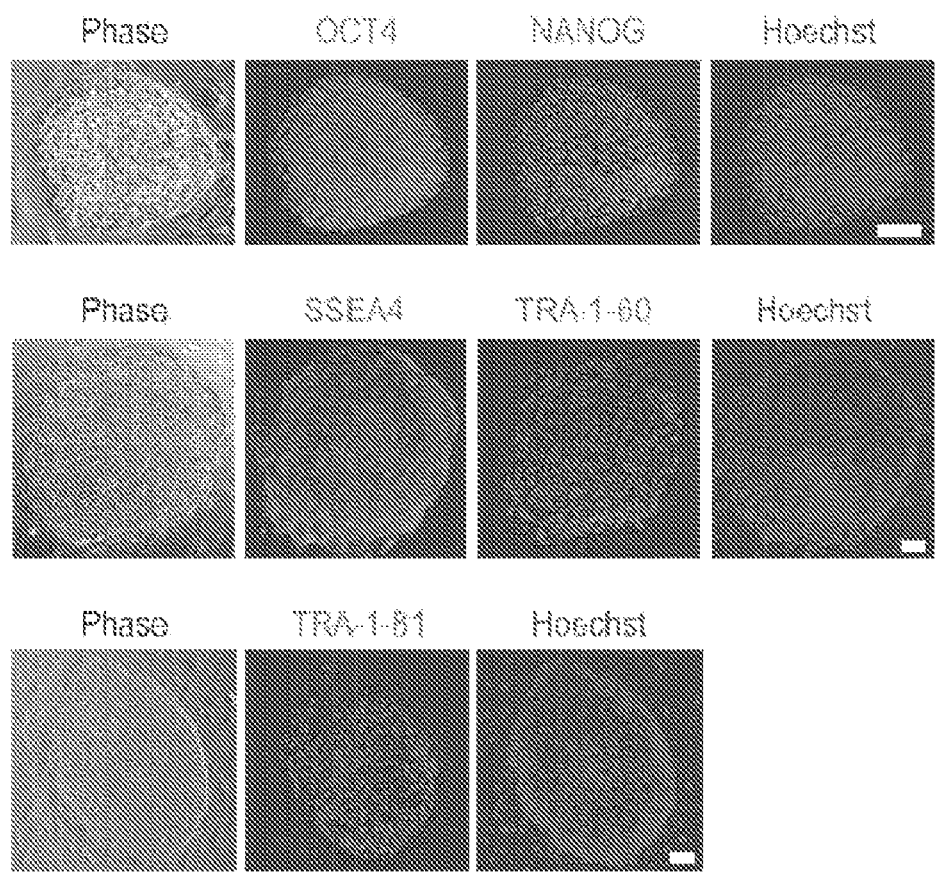
Figure 4D:
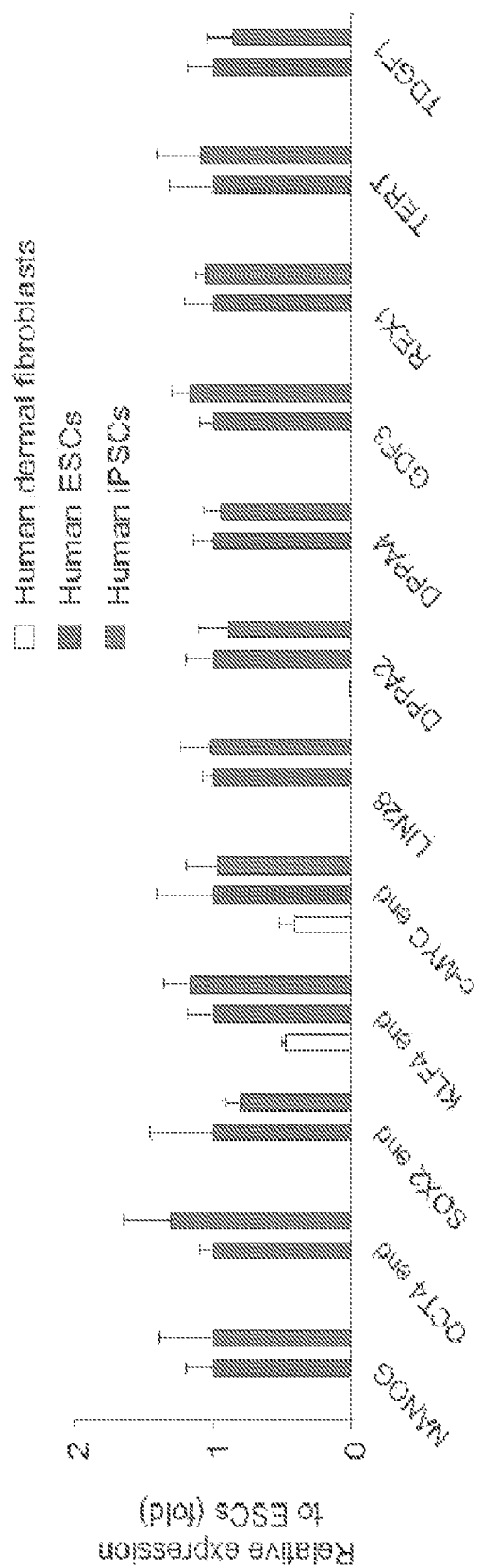
Figure 4E:
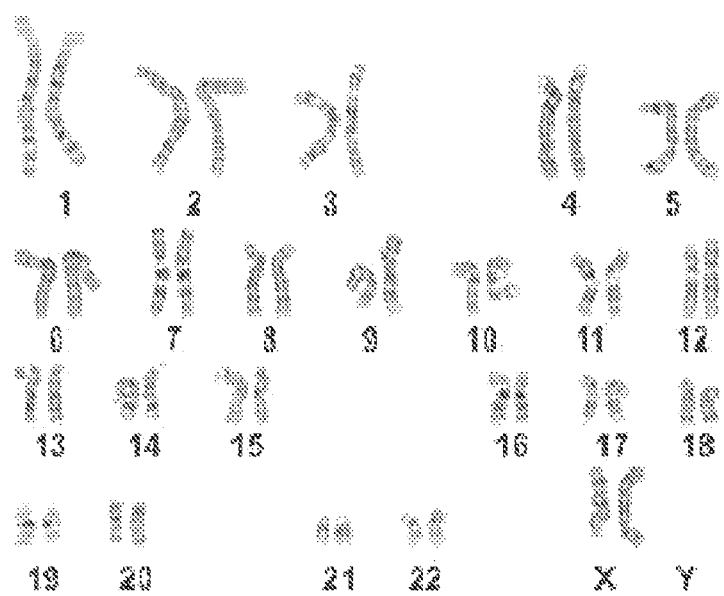
Figure 4F:
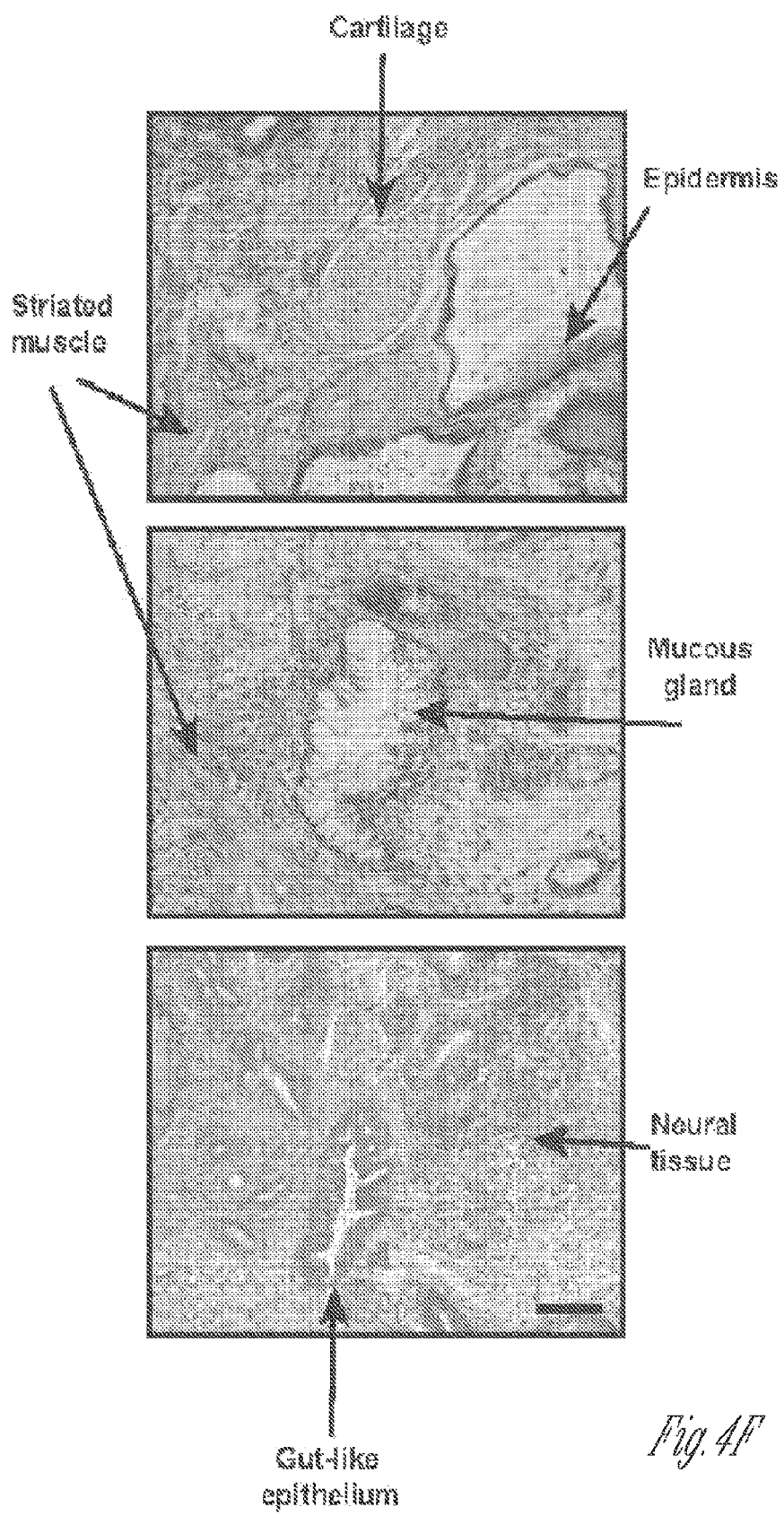

Next it was evaluated if $M_3O$ could also facilitate generation of human iPSCs in comparison to OSKM. Human $M_3O$-SKM and OSKM were transduced into human dermal fibroblasts prepared from a 34-year-old female. Because these cells did not harbor a transgene that could be used as a convenient marker for reprogramming, expression of the pluripotency protein NANOG was monitored by immunofluorescence staining as an iPSC indicator. NANOG-positive human ESC-like colonies emerged around day 8 with $M_3O$-SKM, with the number increasing by around day 15 when 0.30±0.033% of the original fibroblasts were converted to iPSC colonies (FIG. 4A, 4B). In contrast, when OSKM was transduced, NANOG-positive colonies did not emerge until around day 12 and eventually only 0.0052±0.0018% of the fibroblasts were turned into iPSC colonies. This indicates 58-fold increased efficiency with $M_3O$-SKM in comparison to OSKM. Furthermore, while less than 10% of the colonies that appeared with OSKM were NANOG positive, more than 90% of the colonies produced with $M_3O$-SKM were NANOG-positive, consistent with the results for mouse iPSCs. Cloned iPSCs prepared with $M_3O$-SKM also expressed endogenous OCT4 and surface markers SSEA4, TRA-1-60 and TRA-1-81 on day 28 (FIG. 4C). Transduced $M_3O$ was suppressed by this day (not shown). In addition, iPSCs prepared with $M_3O$-SKM expressed twelve pluripotency genes as demonstrated by quantitative RT-PCR (FIG. 4D). All twenty mitotic spreads prepared from a cloned $M_3O$-SKM iPSCs demonstrated normal karyotypes (FIG. 4E). Finally, they formed teratomas when injected into an NOD/SCID mouse (FIG. 4F), proving pluripotency of the cells.

Chromatin Analyses of Pluripotency Genes in M$_3$O-MEFs

Figure 5A:
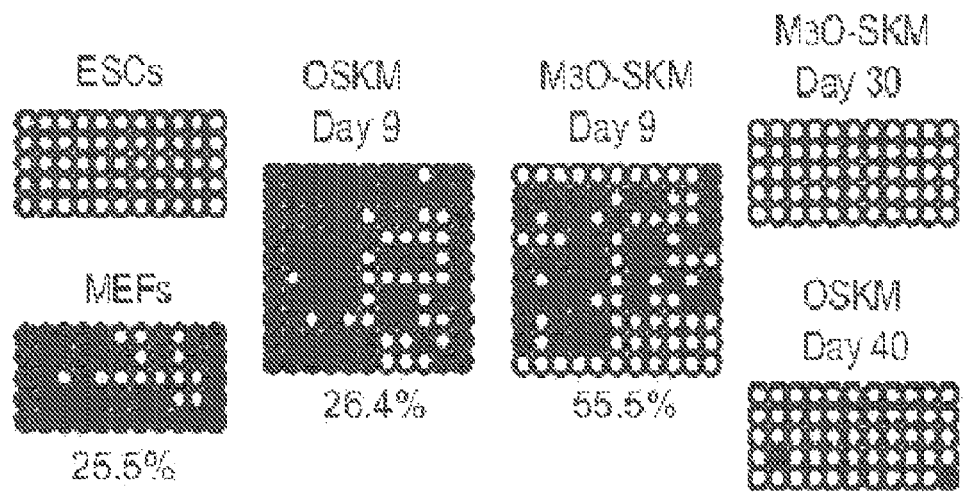
FIG. 5. Chromatin analyses of the Oct4 gene in MEFs transduced with $M_3O$-SKM ($M_3O$-MEFs) and those with OSKM (O-MEFs). (A) DNA methylation patterns at the proximal promoter of the Oct4 gene analyzed with bisulfite sequencing. Black circles indicate methylated CpG and open circles, unmethylated CpG. The proportion of unmethylated CpG sites was calculated by dividing the number of unmethylated CpG sites by the total number of CpG sites in each cell type. (B) Flow cytometry of O-MEFs and $M_3O$-MEFs prepared with Protocol B and harvested on day 9. (C) ChIP analyses of the binding levels of Oct4, Sox2, and the Paf1 complex subunits at the distal enhancer (Region 1) and initiation site (Region 2) of the Oct4 gene in $M_3O$-MEFs and O-MEFs. Data represent the mean±SEM of three independent experiments. All y axes indicate relative enrichment (fold). Relative enrichment in ESCs was defined as 1.0. ESCs and MEFs were mixed at a 13:87 ratio in the sample labeled as ESCs+MEFs (blue). The difference of the values between the two samples indicated by an asterisk was statistically significant ($p<0.01$). (D) Analyses of the accessibility of the restriction enzyme NsiI to chromatin at the distal enhancer of the Oct4 gene by Southern blotting. Locations of the enzyme recognition site and probe are shown in relation to the distal enhancer of the Oct4 gene (top). The transcription initiation site was defined as position 1. Appearance of new DNA fragments following digestion with NsiI are shown (bottom). Percentage of digested chromatin was obtained by dividing the combined signal intensity of the bands at 752 and 652 bp by the combined signal intensity of the two bands and the band at 1404 bp. Cloned O-iPSCs and $M_3O$-iPSCs were used for day 30 lanes. GFP-negative population was collected by a FACS and analyzed for the day 9 GFP (−) lane of $M_3O$-MEFs (far right). (E) ChIP analyses of the levels of three histone modifications associated with active genes at the initiation site (Region 2) and a coding region (Region 3) of the Oct4 gene. (F) ChIP analyses of the levels of two histone modifications associated with inactive genes at a coding region of the Oct4 gene (Region 3). Relative enrichment in MEFs was defined as 1.0.
Figure 5B:
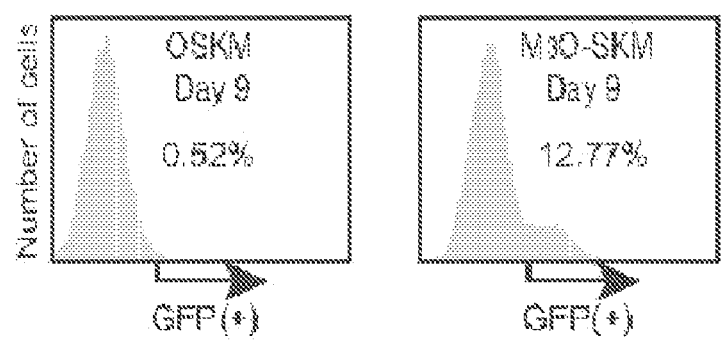

To understand how M$_3$O-SKM facilitated nuclear reprogramming at the molecular level, several chromatin changes at the Oct4 gene were examined during the early phase of iPSC generation. All analyses were performed with Protocol B on all MEFs in a culture dish including GFP-positive and -negative cells without subculture for 9 days. First, changes in DNA methylation at the promoter of the Oct4 gene were studied. CpG dinucleotides at the proximal promoter of the Oct4 gene are heavily methylated in MEFs, unlike in ESCs and iPSCs[22] (FIG. 5A), and this serves as a major inhibitory mechanism for Oct4 transcription. While the number of unmethylated CpG sites remained essentially the same on day 9 in O-MEFs, the number increased approximately twofold in M$_3$O-MEFs on the same day (FIG. 5A, 25.5% vs 55.5%). The more advanced demethylation in M$_3$O-MEFs than in O-MEFs is consistent with the higher percentage of GFP-positive cells in M$_3$O-MEFs than in O-MEFs on day 9 (12.77% vs 0.52%) as shown by flow cytometry (FIG. 5B).

Figure 5C:
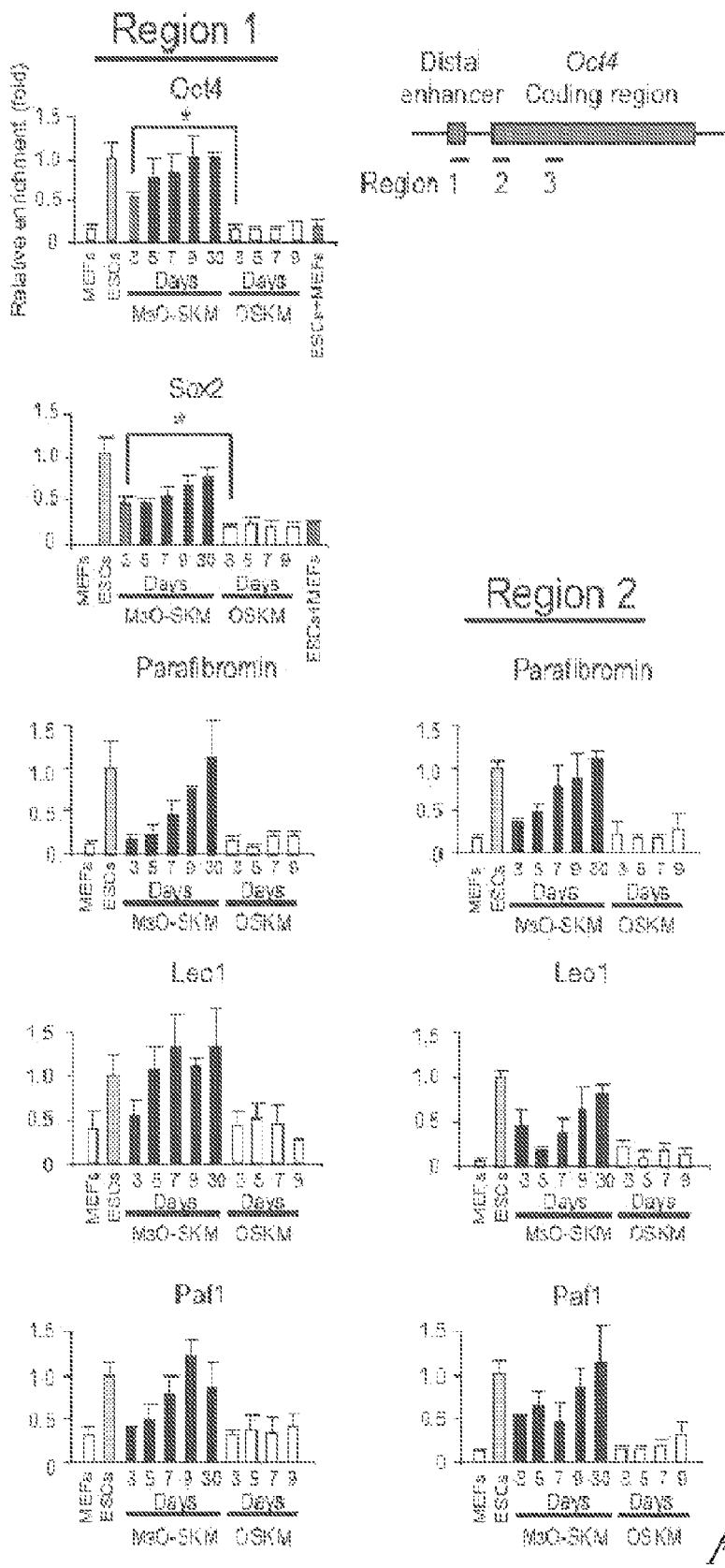
Figure 5D:
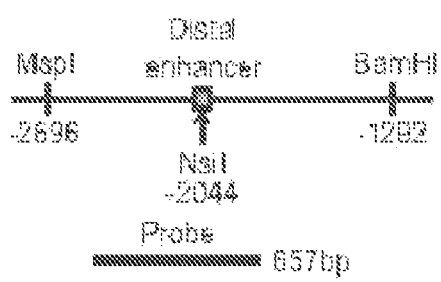
Figure 5D:
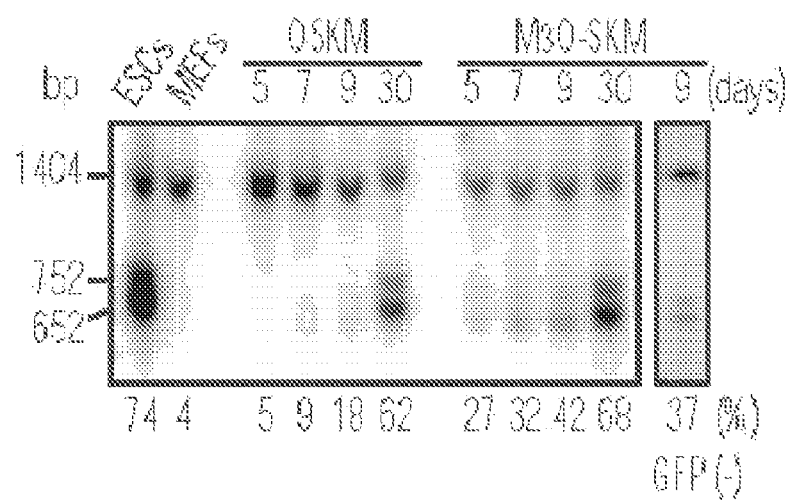

Next, the binding of Oct4 and Sox2 to the distal enhancer of the Oct4 gene[1] using chromatin immunoprecipitation (ChIP) was studied. The binding of Oct4 and Sox2 to the distal enhancer remained low with O-MEFs (FIG. 5C). However, Oct4, which was identical to M$_3$O in this case, was already highly bound to the Oct4 distal enhancer in M$_3$O-MEFs as early as day 3 when no GFP-positive colonies had yet appeared (FIG. 5C, the red column in the Oct4 panel). The Oct4-binding level gradually increased subsequently, eventually reaching the level comparable to that seen in ESCs on day 9. The chromatin binding of Sox2 displayed a similar tendency. The binding levels of these two proteins in the mixture of ESCs and MEFs at a 13:87 ratio was studied. This study showed substantially lower binding of Oct4 and Sox2 in comparison to the day 9 levels in M$_3$O-MEFs (FIG. 5C, ESCs+MEFs in blue). This observation indicates that Oct4 and Sox2 were bound to the Oct4 enhancer in the majority of M$_3$O-MEFs including GFP-negative cells on day 9. The increased binding of these two proteins to chromatin in M$_3$O-MEFs prompted us to investigate if chromatin accessibility at the distal enhancer was also increased in M$_3$O-MEFs. Increased chromatin accessibility is generally indicated by higher sensitivity to DNAses[23]. Chromatin from M$_3$O-MEFs and O-MEFs was digested with the restriction enzyme NsiI and analyzed DNA fragments using Southern blotting. Indeed, chromatin accessibility was consistently higher in M$_3$O-MEFs compared to O-MEFs between day 5 and day 9 (FIG. 5D). Additionally, GFP-negative M$_3$O-MEFs were selected with a FACS on day 9 followed by NsiI digestion analysis. This GFP-negative population also demonstrated increased sensitivity to NsiI (FIG. 5D, far right), indicating that the minor GFP-positive population did not significantly influence the overall result of chromatin accessibility.

Figure 5E:
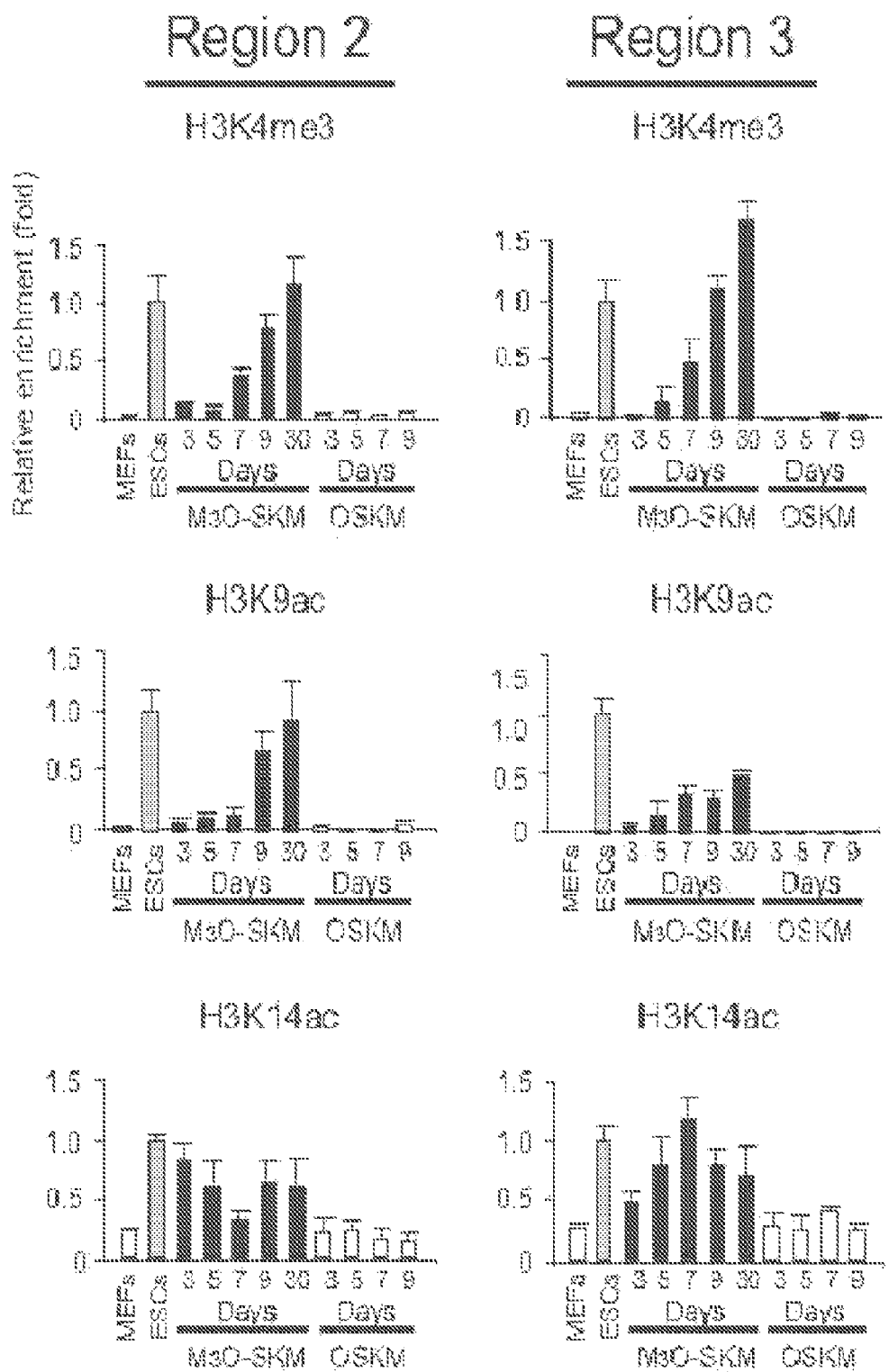
Figure 5F:
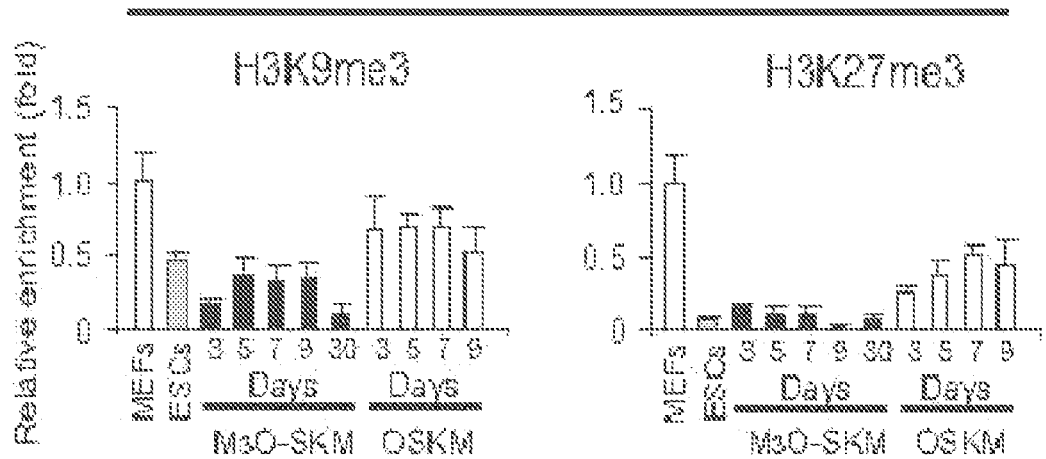

Previous reports have shown that the Paf1 complex is recruited to the distal enhancer of the Oct4 gene through binding to the Oct4 protein[24,25] and then generally moves to the coding region of the gene[26]. Three Paf1 complex subunits—parafibromin, Leo1 and Paf1—displayed a gradual increase of binding to the distal enhancer and coding region of the Oct4 gene in M$_3$O-MEFs, but not in O-MEFs, between days 3 and 9 following transduction (FIG. 5C). The Paf1 complex recruits the histone methyltransferase complex COMPASS, which catalyzes trimethylation of lysine 4 on histone H3 (H3K4me3)[26]. This histone modification, a marker for active genes, was also increased specifically in M$_3$O-MEFs in the coding region of the Oct4 gene (FIG. 5E). Two other markers for active genes, acetylation of lysines 9 and 14 on histone H3 (H3K9ac and H3K14ac)[27], were also increased in M$_3$O-MEFs (FIG. 5E). In addition, two markers for suppressed genes, trimethylation of H3K9 (H3K9me3) and H3K27 (H3K27me3)[27], were more decreased in M$_3$O-MEFs than those in O-MEFs (FIG. 5F). Similar results were observed at the Sox2 locus (FIG. 9). Among these chromatin changes, the levels of H3K9me3 and H3K27me3 in M$_3$O-MEFs most quickly reached the levels observed in ESCs (FIG. 5F), suggesting that the loss of these suppressive histone markers precedes other chromatin modifications. Taken together, these results demonstrate that chromatin at Oct4 and Sox2 loci was generally remodeled in majority of M$_3$O-MEFs, including the GFP-negative population, toward an ESC pattern during the first ten days after transduction, while chromatin in the majority of O-MEFs was not significantly altered.

Figure 6A:
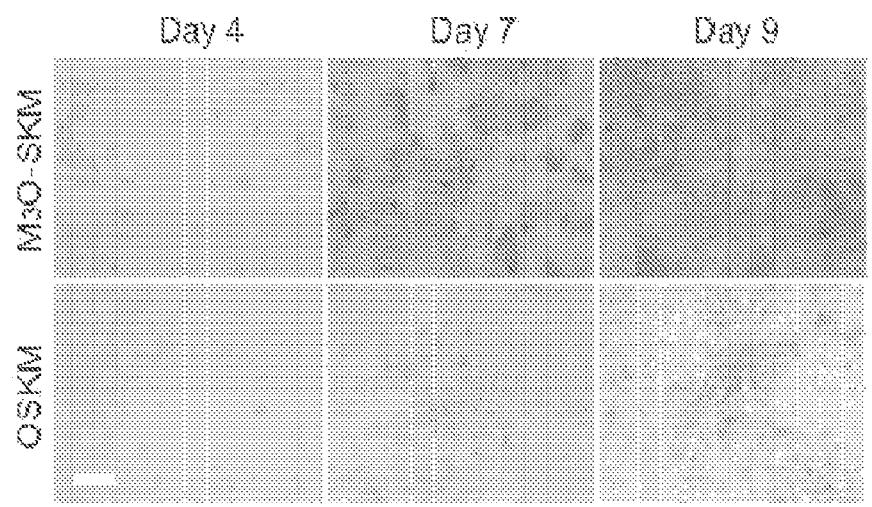
FIG. 6. Effects of $M_3O$-SKM and OSKM on expression of pluripotency markers and cell proliferation. (A) Temporal profiles of expression patterns of alkaline phosphatase. Bar, 100 μm. (B) Temporal profiles of expression patterns of SSEA1. Bar, 100 μm. (C) Flow cytometry comparing the expression level of SSEA1 between MEFs transduced with OSKM and those transduced with $M_3O$-SKM. (D) Cell proliferation patterns of MEFs transduced with $M_3O$ or Oct4. Means±SEM of three independent experiments are shown. (E) Cell proliferation patterns of MEFs transduced with $M_3O$-SKM or OSKM.
Figure 6B:
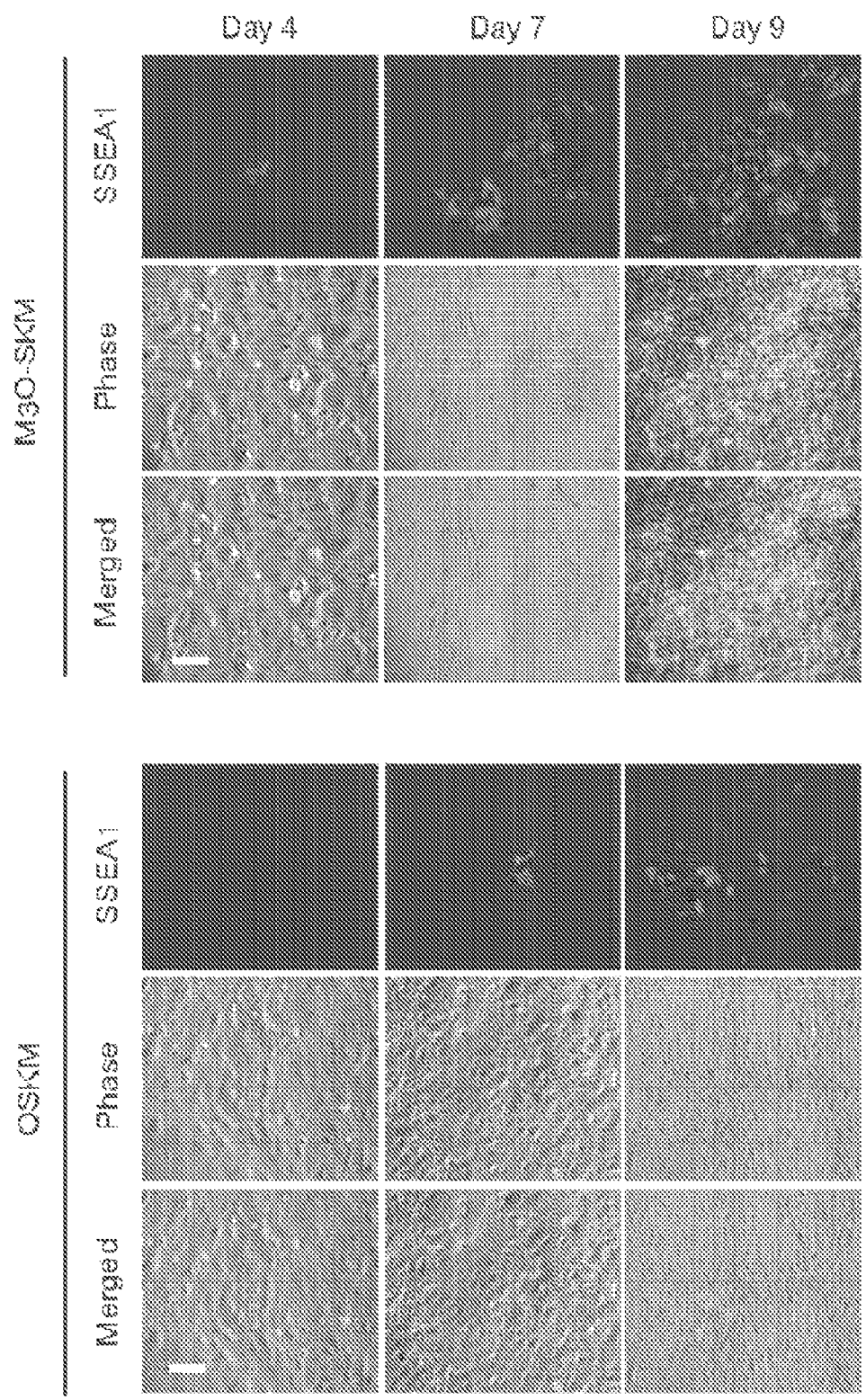
Figure 6C:
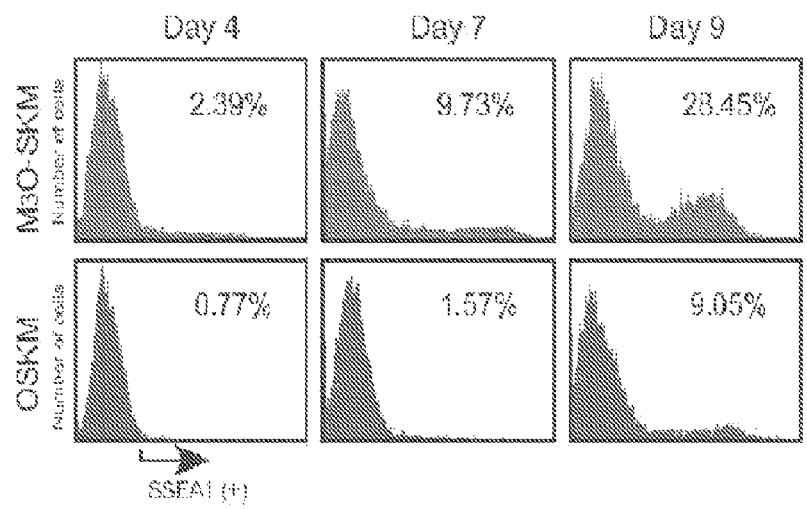
Figures 6D, 6E:
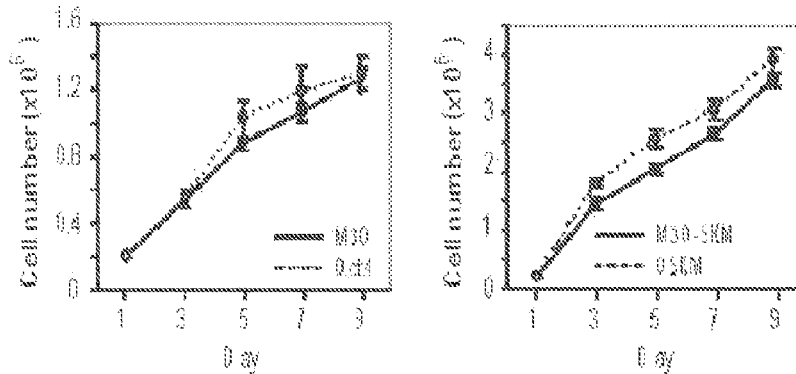

In addition to global chromatin remodeling, M$_3$O-SKM also elicited wider expression of two pluripotency markers than OSKM: alkaline phosphatase and SSEA1. Alkaline phosphatase was almost ubiquitously expressed by day 9 in M$_3$O-MEFs, unlike the weak and heterogeneous expression observed in O-MEFs (FIG. 6A). SSEA1 was also more widely expressed in M$_3$O-MEFs than in O-MEFs by day 9 as shown by immunofluorescence microscopy and flow cytometry (FIG. 6B, 6C). While alkaline phosphatase and SSEA1 are not exclusively expressed in pluripotent cells, these findings support the interpretation that M$_3$O-SKM remodeled the chromatin in much more wider population of the cells to a certain degree unlike OSKM. Rapid cell proliferation is known to facilitate iPSC generation as shown using p53-null MEFs[18]; however, neither M$_3$O-SKM nor M$_3$O alone facilitated MEF proliferation during the initial 9 days after transduction (FIG. 6D, 6E).

Chromatin Analyses of Pluripotency Genes without c-Myc

Figure 7A:
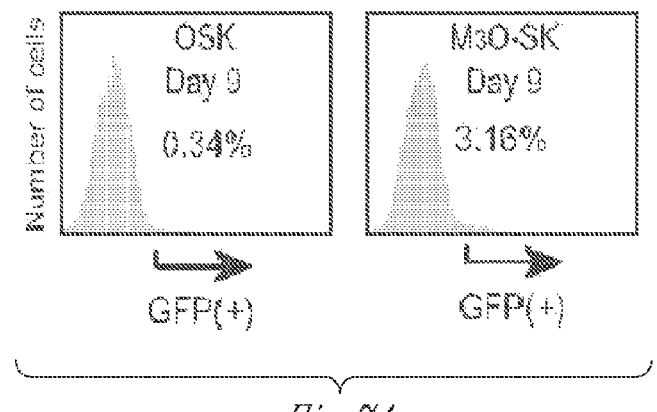
FIG. 7. Chromatin analyses of day 9 at the Oct4 gene comparing transduction of MEFs with different gene combinations. (A) Flow cytometry of MEFs transduced with $M_3O$-SK and OSK. (B) DNA methylation analysis by bisulfite sequencing. MEFs were transduced with one (1F), two (2F), or three (3F) transcription factor genes. (C) ChIP studies on transcription factor binding at the distal enhancer. (D) ChIP analyses on histone modifications associated with active genes. (E) ChIP studies on histone modifications associated with suppressed genes. (F) Hypothetical summary of epigenetic remodeling induced by $M_3O$-SKM (right) in comparison to the lack of remodeling with OSKM (left). Binding sites for Oct4 and Sox2 are located adjacent to each other at the distal enhancer of Oct4[1]. Transduced Oct4 and Sox2 cannot bind to their respective binding sites (blue box and gray box, respectively) in the majority of O-MEFs due to condensed chromatin. In contrast, $M_3O$ and Sox2 can effectively bind to each binding site in $M_3O$-MEFs through the effects of the unidentified binding proteins to the MyoD TAD domain. Recruitment of these proteins eventually contributes to DNA demethylation at the proximal promoter and a histone modification pattern typical of active genes at the coding region.
Figure 7B:
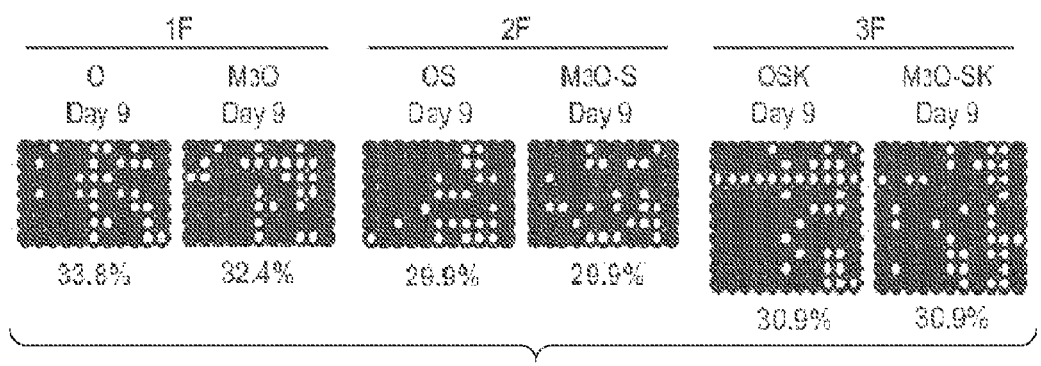

M$_3$O-SK induced GFP-positive colonies over 100-fold more efficiently than OSKM with Protocol B (0.44% with M$_3$O-SK in FIG. 1D vs 0.0035% with OSKM in FIG. 1F). This observation suggests that the M$_3$ domain could compensate for the lack of c-Myc when Oct4 activation was used as an indicator. Although several roles of c-Myc have been proposed, its precise function in iPSC formation remains elusive. To further understand the roles of c-Myc in the activation of pluripotency genes, chromatin analyses at the Oct4 and Sox2 loci were repeated comparing MEFs transduced with three genes (M$_3$O-SK or OSK) and four genes (M$_3$O-SKM of OSKM) on day 9 when the effects of M$_3$O-SKM were readily detectable. One gene (M$_3$O or Oct4) and two genes (M$_3$O+Sox2 or Oct4+Sox2) were transduced for comparison. At this time point, 3.16% of MEFs were GFP-positive with M$_3$O-SK (FIG. 7A), and no GFP-positive cells were observed with other combinations of one, two, or three genes. However, M$_3$O-SK did not significantly decrease the overall level of DNA methylation compared with other gene combinations (FIG. 7B).

Figure 7C:
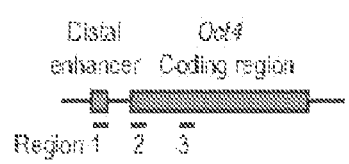
Figure 7C:
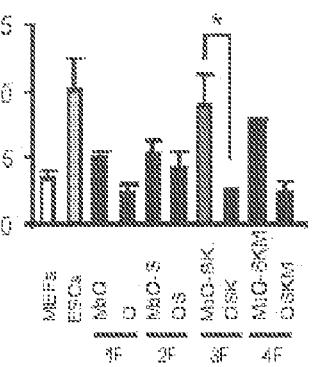
Figure 7C:
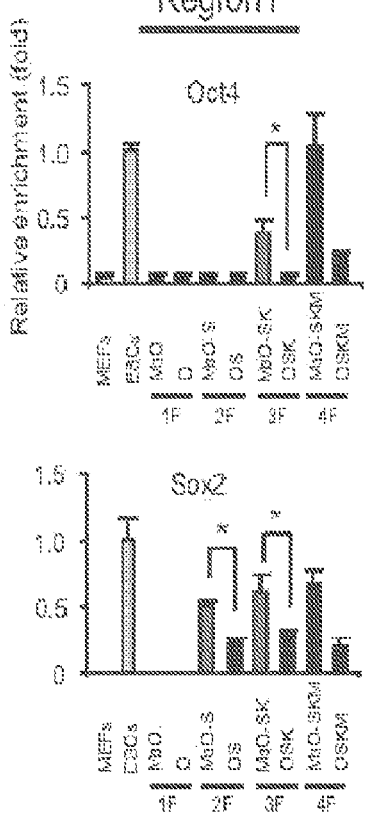
Figure 7C:
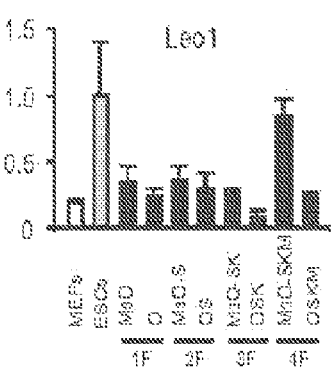
Figure 7C:
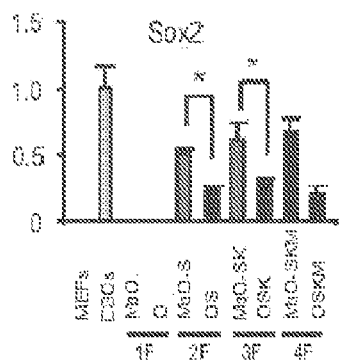
Figure 7C:
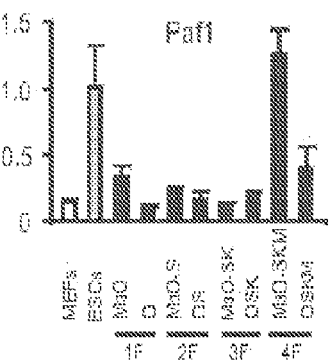
Figure 10A:
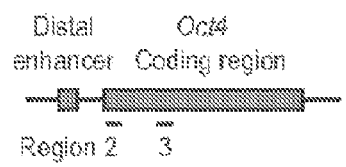
FIG. 10. ChIP analyses on day 9 of the Oct4 gene comparing transduction of one (1F), two (2F), three (3F) and four (4F) transcription factor genes. (A) Transcription factor binding. (B) Histone modifications associated with gene activation.
Figure 10A:
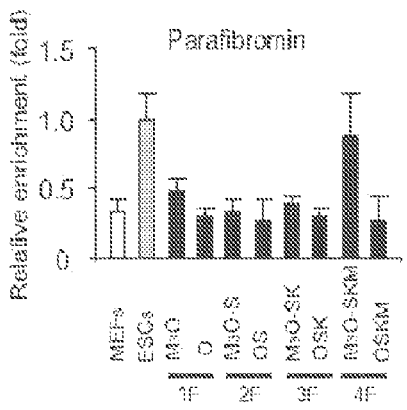
Figure 10A:
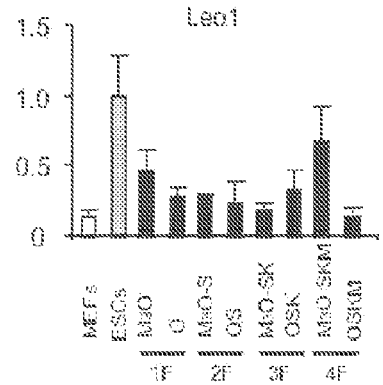
Figure 10A:
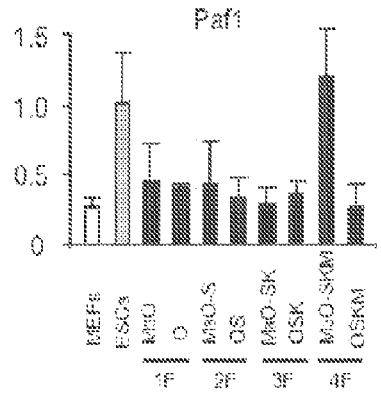
Figure 10B:
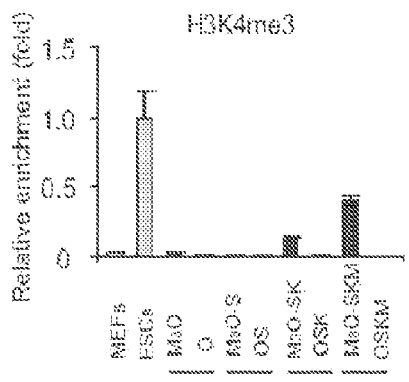
Figure 10B:
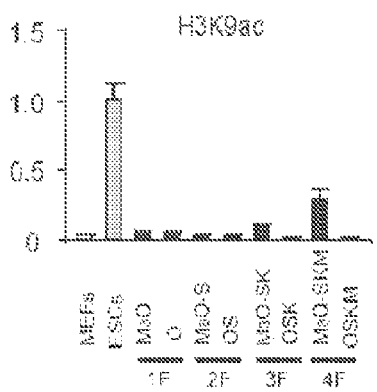
Figures 11A, 11B:
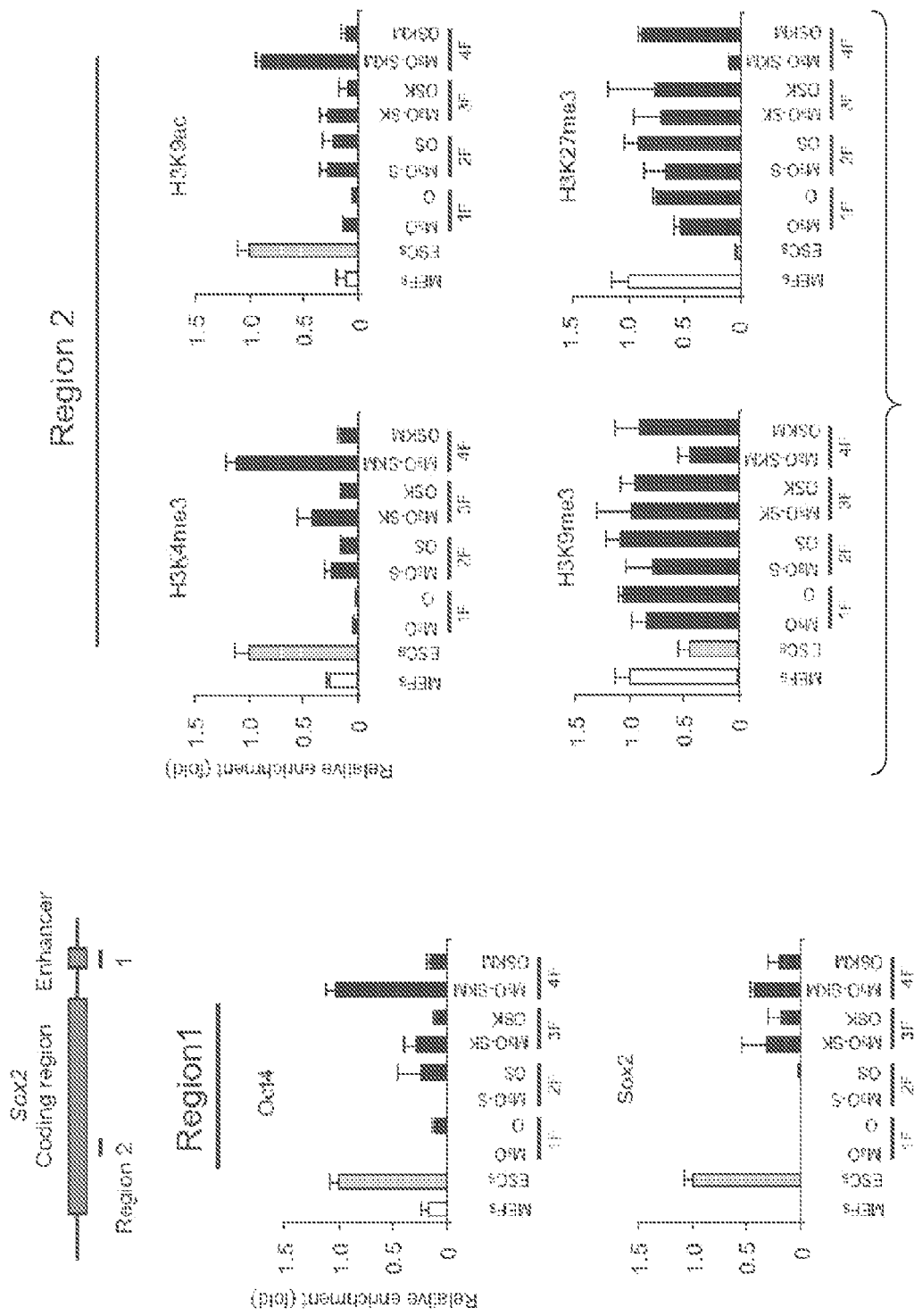
FIG. 11. ChIP analyses on day 9 of the Sox2 gene comparing transduction of one (1F), two (2F), three (3F) and four (4F) transcription factor genes. (A) Transcription factor binding at the enhancer. (B) Histone modifications associated with gene activation and suppression.

As for transcription factor binding to the enhancer, M$_3$O facilitated binding of Oct4, Sox2, and parafibromin in combination with Sox2 or Sox2 and Klf4 (FIG. 7C, red), with some of these binding levels comparable to levels achieved with M$_3$O-SKM. However, Leo1 and Paf1 were not recruited to the enhancer without c-Myc (FIG. 7C). The binding of parafibromin, Leo1, and Paf1 to the initiation site of Oct4 was also weak without c-Myc (FIG. 10A). Consistent with this partial assembly of the Paf1 complex at the Oct4 gene, the level of H3K4me3 remained low without c-Myc (FIG. 7D, 10B). Another active gene marker, H3K9ac, also remained low without c-Myc (FIG. 7D, 10B). Whereas H3K9me3 was effectively decreased by M$_3$O-S and M₃O-SK, H3K27me3 was more resistant to demethylation by any of the gene combinations without c-Myc (FIG. 7E). At the Sox2 gene, compared to the Oct4 gene, M₃O did not substantially increase the binding of Oct4 or Sox2 to the enhancer alone or in combination with Sox2 or Sox2 and Klf4 (FIG. 11A). The changes in the levels of H3K4me3, H3K9ac, H3K9me3 and H3K27me3 were all weak in the absence of c-Myc (FIG. 11B). Together, these chromatin studies indicate that while M₃O could facilitate formation of GFP-positive colonies without c-Myc, the overall level of chromatin remodeling in GFP-negative MEFs was low in the absence of c-Myc.

Discussion

Figure 7F:
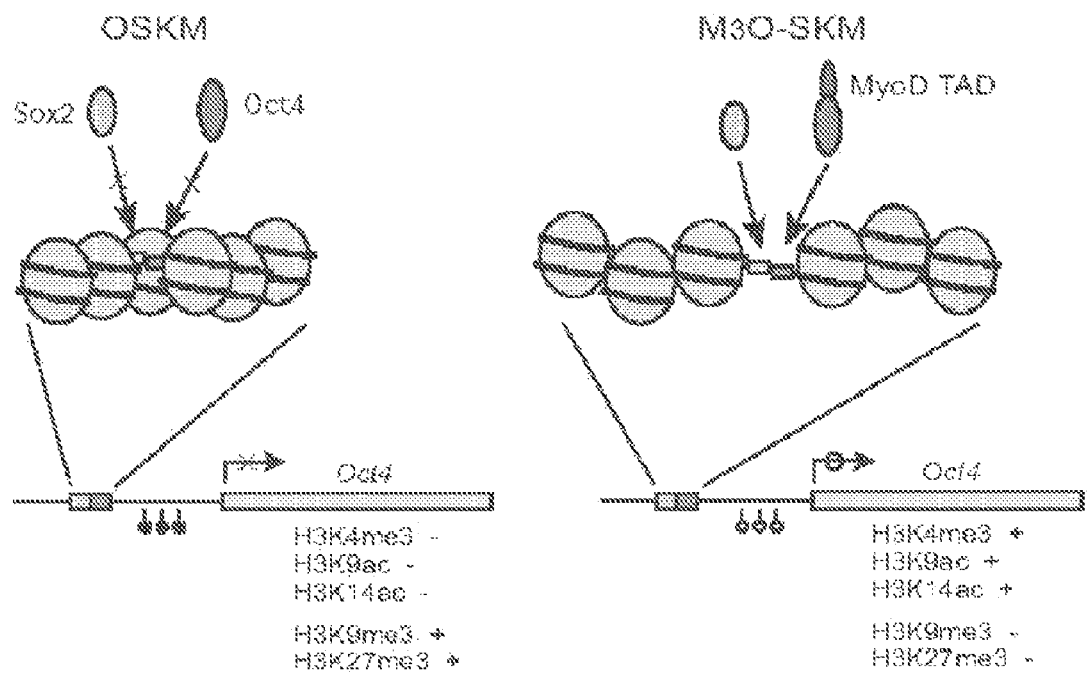

The present study advances the field of iPSC biology by showing that one of the rate-limiting steps in iPSC formation with OSKM is poor chromatin accessibility at pluripotency genes and that a strong transactivating domain can overcome this problem. Because iPSC formation was dramatically improved with M₃O-SKM, the factors required to increase chromatin accessibility most likely already exist within MEFs but are not effectively recruited to pluripotency genes when using OSKM. Our current working model is that the MyoD TAD overcomes the barrier of closed chromatin by effectively attracting chromatin modifying proteins and thereby facilitating the binding of Oct4 and other regulatory proteins as well as epigenetic modifications at pluripotency genes (FIG. 7F). Myc family proteins have been proposed to globally relax chromatin in part through activation of the histone acetyltransferase GCN5 and in part through direct binding to thousands of genomic loci[28,29]. The results also support c-Myc's potential roles in chromatin remodeling.

One of the central questions related to the molecular mechanisms of iPSC formation is how closed chromatin at the loci of Oct4, Sox2, and Nanog are opened by OSKM. Little is known about this mechanism. One potential mechanism is that chromatin disruption occurs during repeated DNA replication as suggested by a report that 92% of B lymphocytes derived from inducible OSKM transgenic mice become iPSCs after 18 weeks of culture[18]. Additionally, knockdown of p53 in B cells shortened both cell doubling time and the time required to form iPSCs by twofold. However, this does not seem to be the case for M₃O-SKM since it did not facilitate cell proliferation. Additionally, emerging GFP-positive colonies contained far less cells than their counterparts obtained from B cells. It has been difficult to perform biochemical analysis of the early process of iPSC formation, such as epigenetic remodeling at pluripotency genes, because of the presence of feeder cells and non-responsive MEFs that comprise more than 90% of transduced cells. However, the MyoD TAD eliminated the requirement for feeder cells and achieved significant levels of epigenetic remodeling even in those MEFs that eventually fell short of activating GFP with Protocol B. Thus, the MyoD TAD is expected to facilitate the dissection of epigenetic processes during the early phase of iPSC formation.

By combining transcription factors with TADs, this approach to nuclear reprogramming is expected to have a range of applications from inducing pluripotency, as shown in this study, to inducing direct conversion from one differentiated cell type to another without transitioning through iPSCs[17,33,34]. The strategy of TAD-fusion to potentiate transactivators will further advance the study of nuclear reprogramming. The effect of each TAD may be on dependent on cell types, host transcription factors, and target genes. Other TADs have been used to amplify the activity of transcription factors. For instance, the TAD of VP16 was fused to the transcription factor Pdx1 to facilitate conversion of hepatocytes to pancreatic cells[36,37]. However, the MyoD TAD has not been used in nuclear reprogramming. The TAD-fusion approach is applicable to combinations of many other transcription factors and TADs to amplify the activity of the host transcription factor and control cell fate decisions.

Sequence Information of the Plasmid Constructs

Following is a list of plasmid constructs used in the above work as well as two constructs based on the VP16 gene and data therefor.

1) Mouse M₃O

The M₃ domain of the mouse MyoD cDNA was fused to the amino terminus of the full-length mouse Oct4 cDNA using PCR and inserted into the EcoRI site of the pMXs-IP vector.

PCR for Mouse M₃O

The cDNA encoding the M₃ domain of mouse MyoD (amino acids 1-62) was amplified with two primer sets, MyoDOct4F4 (GAGAATTCGCCATGGAGCTTC-TATCGCCGCCAC; SEQ ID NO:1) and MOΔ63-109R1 (CAGGTGTCCAGCCATGTGCTCCTCCGGTTTCAG; SEQ ID NO:2). Full length Oct4 cDNA was amplified with two primer sets, MOΔ63-109F1 (CTGAAACCGGAG-GAGCACATGGCTGGACACCTG; SEQ ID NO:3) and MyoDOct4R5 (CGGAATTCTCTCAGTTTGAATG-CATGGGAGAG; SEQ ID NO:4). The two PCR products of each first PCR were used as a template for the secondary PCR with the primer set MyoDOct4F4 and MyoDOct4R5. M₃O was directly subcloned into EcoRI site of pMXs-IP.

PCR Parameters

| Denature | 94° C. | 2 min |
| Denature | 94° C. | 15 sec* |
| Anneal | 57° C. | 30 sec* |
| Extend | 68° C. | 1 min* |
| Final extension | 68° C. | 7 min |

*Repeat 25 cycles

The DNA Sequence of Mouse M₃O Taken from Mouse MyoD (SEQ ID NO: 5)
atggagcttctatcgccgccactccgggacatagacttgacaggccccgacggctctctctgctcctttgagaca gcagacgacttctatgatgatccgtgtttcgactcaccagacctgcgcttttttgaggacctggacccgcgcctg gtgcacgtgggagccctcctgaaaccggaggagcacatggctggacacctggcttcagacttcgccttctcaccc ccaccaggtgggggtgatgggtcagcagggctggagccgggctgggtggatcctcgaacctggctaagcttccaa gggcctccaggtgggcctggaatcggaccaggctcagaggtattggggatctccccatgtccgcccgcatacgag ttctgcggagggatggcatactgtggacctcaggttggactgggcctagtcccccaagttggcgtggagactttg -continued

```
cagcctgagggccaggcaggagcacgagtggaaagcaactcagagggaacctcctctgagccctgtgccgaccgc cccaatgccgtgaagttggagaaggtggaaccaactcccgaggagtcccaggacatgaaagccctgcagaaggag ctagaacagtttgccaagctgctgaagcagaagaggatccacttggggtacacccaggccgacgtggggctcacc ctgggcgttctctttggaaaggtgttcagccagaccaccatctgtcgcttcgaggccttgcagctcagccttaag aacatgtgtaagctgcggcccctgctggagaagtgggtggaggaagccgacaacaatgagaaccttcaggagata tgcaaatcggagaccctggtgcaggcccggaagagaaagcgaactagcattgagaaccgtgtgaggtggagtctg gagaccatgtttctgaagtgcccgaagccctccctacagcagatcactcacatcgccaatcagcttgggctagag aaggatgtggttcgagtatggttctgtaaccggcgccagaagggcaaaagatcaagtattgagtattcccaacga gaagagtatgaggctacagggacacctttcccagggggggctgtatcctttcctctgccccaggtccccacttt ggcaccccaggctatggaagccccacttcaccacactctactcagtcccttttcctgagggcgaggcctttccc tctgttcccgtcactgctctgggctctcccatgcattcaaactga
```

Mouse M₃O Primer Sequences

MyoDOct4F4: GAGAATTCGCCATGGGAGCTTCTATCGCCGCCAC (SEQ ID NO: 6)

MOΔ63-109R1: CAGGTGTCCAGCCATGTGCTCCTCCGGTTTCAG (SEQ ID NO: 7)

MOΔ63-109F1: CTGAAACCGGAGGAGCACATGGCTGGACACCTG (SEQ ID NO: 8)

MyoDOct4R5: CGGAATTCTCTCAGTTTGAATGCATGGGAGAG (SEQ ID NO: 9)

Accession Numbers
Mouse MyoD: M84918, NM_010866
Mouse Oct4 (POU5F1): NM_013633

2) Mouse OM₃

The M₃ domain of the mouse MyoD cDNA was fused to the carboxy terminus of the mouse full length Oct4 cDNA. PCR for Mouse 0M₃

The M3 domain was prepared with PCR using the primer pair M₃F1 and M₃R1 and inserted into the EcoRI and the XhoI sites of the pMXs-IP vector to create the pMXs-IP M₃ vector. Oct4 was then PCR amplified with the primer pair Oct4F1 and Oct4R1, and inserted into the EcoRI site of pMXs-IP M₃ vector.

Mouse OM₃ Sequence (SEQ ID NO: 10)
```
atggctggacacctggcttcagacttcgccttctcaccccaccaggtggggtgatgggtcagcagggctggag ccgggctgggtggatcctcgaacctggctaagcttccaagggcctccaggtgggcctggaatcggaccaggctca gaggtattggggatctccccatgtccgcccgcatacgagttctgcggagggatggcatactgtggacctcaggtt ggactgggcctagtcccccaagttggcgtggagactttgcagcctgagggccaggcaggagcacgagtggaaagc aactcagagggaacctcctctgagccctgtgccgaccgccccaatgccgtgaagttggagaaggtggaaccaact cccgaggagtcccaggacatgaaagccctgcagaaggagctagaacagtttgccaagctgctgaagcagaagagg atccacttggggtacacccaggccgacgtggggctcacc ctgggcgttctctttggaaaggtgttcagccagacc accatctgtcgcttcgaggccttgcagctcagccttaagaacatgtgtaagctgcggcccctgctggagaagtgg gtggaggaagccgacaacaatgagaaccttcaggagatatgcaaatcggagaccctggtgcaggcccggaagaga aagcgaactagcattgagaaccgtgtgaggtggagtctggagaccatgtttctgaagtgcccgaagccctcccta cagcagatcactcacatcgccaatcagcttgggctagagaaggatgtggttcgagtatggttctgtaaccggcgc cagaagggcaaaagatcaagtattgagtattcccaacgagaagagtatgaggctacagggacacctttcccaggg ggggctgtatcctttcctctgccccaggtccccactttggcaccccaggctatggaagccccacttcaccaca ctctactcagtcccttttcctgagggcgaggcctttccctctgttcccgtcactgctctgggctctcccatgcat tcaaacgaattcatggagcttctatcgccgccactccgggacatagacttgacaggccccgacggctctctctgc tcctttgagacagcagacgacttctatgatgatccgtgtttcgactcaccagacctgcgcttttttgaggacctg gacccgcgcctggtgcacgtgggagccctcctgaaaccggaggagcactga
```

Mouse OM₃ Primer Sequences

```
                                           (SEQ ID NO: 11)
Oct4F1:  CGAGAATTCATGGCTGGACACCTG (SEQ ID NO: 12)
Oct4R1:  CGAGAATTCGTTTGAATGCATGGGAGAG (SEQ ID NO: 13)
M₃F1:    CGAGAATTCATGGAGCTTCTATCGCCGCCAC (SEQ ID NO: 14)
M₃R1:    CGACTCGAGTCAGTGCTCCTCCGGTTTCAG
```

PCR Parameters

| Denature | 94° C. | 2 min |
|---|---|---|
| Denature | 94° C. | 15 sec* |
| Anneal | 57° C. | 30 sec* |
| Extend | 68° C. | 1 min* |
| Final extension | 68° C. | 7 min |

*Repeat 25 cycles

Accession Number for Mouse OM₃
Mouse MyoD: M84918, NM_010866
Mouse Oct4 (POU5F1): NM_013633
Activity Test of Making iPSCs
OM₃ converts 3.2% of MEFs to iPSCs.

3) Mouse M₃OM₃

Mouse M₃ was fused to both the amino and carboxy termini of mouse Oct4.
PCR for Mouse M₃OM₃

Mouse M₃ domain was prepared from the mouse MyoD cDNA with PCR using the primer pair M₃OF1 and M₃OR1. Mouse full length Oct4 was prepared with PCR using the primer set M₃OF2 and Oct4R1. To make M₃O, the above two PCR products were used as templates for PCR with the primer pair M₃OF1 and Oct4R1. Finally, to make M₃OM₃, M₃O was inserted into the EcoRI site of the pMXs-IP M₃ vector prepared in the OM₃ construct above.

Mouse M₃OM₃ Sequence

```
                                                               (SEQ ID NO: 15)
atggagcttctatcgccgccactccgggacatagacttgacaggccccgacggctctctctgctcctttgagaca
gcagacgacttctatgatgatccgtgtttcgactcaccagacctgcgcttttttgaggacctggacccgcgcctg
gtgcacgtgggagccctcctgaaaccggaggagcacatggctggacacctggcttcagacttcgccttctcaccc
ccaccaggtgggggtgatgggtcagcagggctggagccgggctgggtggatcctcgaacctggctaagcttccaa
gggcctccaggtgggcctggaatcggaccaggctcagaggtattggggatctccccatgtccgccgcatacgag
ttctgcggagggatggcatactgtggacctcaggttggactgggcctagtcccccaagttggcgtggagactttg
cagcctgagggccaggcaggagcacgagtggaaagcaactcagagggaacctcctctgagccctgtgccgaccgc
cccaatgccgtgaagttggagaaggtggaaccaactcccgaggagtcccaggacatgaaagccctgcagaaggag
ctagaacagtttgccaagctgctgaagcagaagaggatcaccttggggtacacccaggccgacgtggggctcacc
ctgggcgttctctttggaaaggtgttcagccagaccaccatctgtcgcttcgaggccttgcagctcagccttaag
aacatgtgtaagctgcggcccctgctggagaagtgggtggaggaagccgacaacaatgagaaccttcaggagata
tgcaaatcggagaccctggtgcaggcccggaagagaaagcgaactagcattgagaaccgtgtgaggtggagtctg
gagaccatgtttctgaagtgcccgaagccctccctacagcagatcactcacatcgccaatcagcttgggctagag
aaggatgtggttcgagtatggttctgtaaccggcgccagaagggcaaaagatcaagtattgagtattcccaacga
gaagagtatgaggctacagggacacctttcccagggggggctgtatcctttcctctgccccaggtccccacttt
ggcaccccaggctatggaagcccccacttcaccacactctactcagtcccttttcctgagggcgaggcctttccc
tctgttcccgtcactgctctgggctctcccatgcattcaaacgaattcatggagcttctatcgccgccactccgg
gacatagacttgacaggccccgacggctctctctgctcctttgagacagcagacgacttctatgatgatccgtgt
ttcgactcaccagacctgcgcttttttgaggacctggacccgcgcctggtgcacgtgggagccctcctgaaaccg
gaggagcactga
```

Mouse M₃OM₃ Primer Sequences

```
                                                   (SEQ ID NO: 16)
M₃OF1:  GAGAATTCGCCATGGAGCTTCTATCGCCGCCAC (SEQ ID NO:17)
M₃OR1:  CAGGTGTCCAGCCATATCAGCGTTGGTGGTC (SEQ ID NO: 18)
M₃OF2:  GACCACCAACGCTGATATGGCTGGACACCTG (SEQ ID NO: 19)
Oct4R1: CGAGAATTCGTTTGAATGCATGGGAGAG
```

PCR Parameters: The Same as that for OM₃

| Denature | 94° C. | 2 min |
|---|---|---|
| Denature | 94° C. | 15 sec* |
| Anneal | 57° C. | 30 sec* |
| Extend | 68° C. | 1 min* |
| Final extension | 68° C. | 7 min |

*Repeat 25 cycles

Accession Number for Mouse $M_3OM_3$
Mouse MyoD: M84918, NM_010866
Mouse Oct4 (POU5F1): NM_013633

4) Human $M_3O$ DNA

The $M_3$ domain of the human MyoD cDNA was fused to the amino terminus of the full-length human Oct4 cDNA using PCR and inserted into the EcoRI site of the pMXs-IP vector.

PCR for Human $M_3O$

The $M_3$ domain of human MyoD was PCR amplified with the primer pair of $hM_3OF1$ (see below for sequence) and $hM_3OR1$. Human full length Oct4 was PCR amplified with the primer pair of $hM_3OF2$ and $hM_3OR2$. These two PCR products were used as templates for the third PCR with the primers $hM_3OF1$ and $hM_3OR2$.

PCR Parameters

| | | |
|---|---|---|
| Denature | 94° C. | 2 min |
| Denature | 94° C. | 15 sec* |
| Anneal | 57° C. | 30 sec* |
| Extend | 68° C. | 1 min* |
| Final extension | 68° C. | 7 min |

*Repeat 25 cycles

The DNA Sequence of Human $M_3O$ Taken from Human MyoD

```
atggagctactgtcgccaccgctccgcgacgtagacctgacggccccgacggctctctctgctcctttgccaca
acggacgacttctatgacgacccgtgtttcgactccccggacctgcgcttcttcgaagacctggacccgcgcctg
atgcacgtgggcgcgctcctgaaacccgaagagcacatggcgggacacctggcttcggatttcgccttctcgccc
cctccaggtggtggaggtgatgggccagggggccggagccgggctgggttgatcctcggacctggctaagcttc
caaggccctcctggagggcaggaatcggccgggggttgggccaggctctgaggtgtgggggattcccccatgc
ccccgccgtatgagttctgtgggggatggcgtactgtgggcccaggttggagtggggctagtgcccaaggc
ggcttggagacctctcagcctgagggcgaagcaggagtcggggtggagagcaactccgatggggcctccccggag
ccctgcaccgtcacccctggtgccgtgaagctggagaaggagaagctggagcaaaacccggaggagtcccaggac
atcaaagctctgcagaaagaactcgagcaatttgccaagctcctgaagcagaagaggatcaccctgggatataca
caggccgatgtgggggctcaccctgggggttctatttgggaaggtattcagccaaacgaccatctgccgcttttgag
gctctgcagcttagcttcaagaacatgtgtaagctgcggcccttgctgcagaagtgggtggaggaagctgacaac
aatgaaaatcttcaggagatatgcaaagcagaaaccctcgtgcaggcccgaaagagaaagcgaaccagtatcgag
aaccgagtgagaggcaacctggagaatttgttcctgcagtgcccgaaacccacactgcagcagatcagccacatc
gcccagcagcttgggctcgagaaggatgtggtccgagtgtggttctgtaaccggcgccagaagggcaagcgatca
agcagcgactatgcacaacgagaggattttgaggctgctgggtctcctttctcaggggggaccagtgtcctttcct
ctggccccagggccccattttggtaccccaggctatgggagccctcacttcactgcactgtactcctcggtccct
ttccctgagggggaagcctttcccctgtctccgtcaccactctgggctctcccatgcattcaaactga
```

Human $M_3O$ Primer Sequences (SEQ ID NO: 21)
$hM_3OF1$: CGAGAATTCGCCATGGAGCTACTGTCGCCAC (SEQ ID NO: 22)
$hM_3OR1$: CAGGTGTCCCGCCATGTGCTCTTCGGGTTTCAG (SEQ ID NO: 23)
$hM_3OF2$: CTGAAACCCGAAGAGCACATGGCGGGACACCTG (SEQ ID NO: 24)
$hM_3OR2$: CGTGAATTCCTCGAGTCTCAGTTTGAATGCATGGGAGAG Accession Numbers Human MyoD: NM_002478

Human Oct4 (POU5F1): NM_002701

5) VP16LO

The full length of the TAD (amino acids 411-490) of VP16 was fused to the amino terminus of the mouse full-length Oct4 cDNA. VP16 is a protein expressed by the herpes simplex virus type 1 and its transactivation domain is highly powerful.

PCR for VP16LO

The cDNA encoding the transactivation domain of VP16 (amino acids 411-490) was amplified by PCR and inserted into the BamHI and XhoI sites of the pMXs-IP vector to create the pMXs VP16-IP vector. Then the full-length mouse Oct4 cDNA was inserted into the EcoRI and XhoI sites of the pMXs VP16-IP vector.

PCR Primers for VP16

(SEQ ID NO: 25)
VP16F1: CGAGGATCCGCCATGTCGACGGCCCCCCCGACCGATGTC (SEQ ID NO: 26)
VP16R1: CGACTCGAGGAATTCCCCACCGTACTCGTC

PCR Parameters

| | | |
|---|---|---|
| Denature | 94° C. | 2 min |
| Denature | 94° C. | 15 sec* |

| Anneal | 57° C. | 30 sec* |
| Extend | 68° C. | 1 min* |
| Final extension | 68° C. | 7 min |

*Repeat 25 cycles

VP16LO DNA Sequence (SEQ ID NO: 27)

```
atgtcgacgcccccccgaccgatgtcagcctggggggacgagctccacttagacggcgaggacgtggcgatggcgc
atgccgacgcgctagacgatttcgatctggacatgttgggggacggggattccccgggtccgggatttaccccc
acgactccgcccctacggcgctctggatatggccgacttcgagtttgagcagatgtttaccgatgcccttggaa
ttgacgagtacggtggggaattcatggctggacacctggcttcagacttcgccttctcaccccaccaggtgggg
gtgatgggtcagcagggctggagccgggctgggtggatcctcgaacctggctaagcttccaagggcctccaggtg
ggcctggaatcggaccaggctcagaggtattgggatctccccatgtccgcccgcatacgagttctgcggaggga
tggcatactgtggacctcaggttggactgggcctagtccccaagttggcgtggagactttgcagcctgagggcc
aggcaggagcacgagtggaaagcaactcagagggaacctcctctgagccctgtgccgaccgccccaatgccgtga
agttggagaaggtggaaccaactcccgaggagtcccaggacatgaaagccctgcagaaggagctagaacagtttg
ccaagctgctgaagcagaagaggatcaccttgggtacacccaggccgacgtgggctcaccctgggcgttctct
ttggaaaggtgttcagccagaccaccatctgtcgcttcgaggccttgcagctcagccttaagaacatgtgtaagc
tgcggcccctgctggagaagtgggtggaggaagccgacaacaatgagaaccttcaggagatatgcaaatcggaga
ccctggtgcaggcccggaagagaaagcgaactagcattgagaaccgtgtgaggtggagtctggagaccatgtttc
tgaagtgcccgaagccctccctacagcagatcactcacatcgccaatcagcttgggctagagaaggatgtggttc
gagtatggttctgtaaccggcgccagaagggcaaaagatcaagtattgagtattcccaacgagaagagtatgagg
ctacagggacacctttcccagggggggctgtatcctttcctctgccccaggtcccactttggcacccaggct
atggaagccccacttcaccacactctactcagtccctttcctgagggcgaggcctttccctctgttcccgtca
ctgctctgggctctcccatgcattcaaactga
```

Accession Number for VP16
Human herpesvirus 1 complete genome: X14112.1
Tegument protein VP16 from human herpes simplex virus type 1: NP_044650

Activity Test of Making iPSCs
VP16LO-SKM converts around 0.5% of mouse embryonic fibroblasts to iPSCs, which is lower than $M_3O$-S KM (5.3%) but still higher than OSKM (0.08%). In addition, VP16LO-SKM does not require feeder cells, unlike OSKM, to make iPSCs.

6) VP16SO
A part of the TAD (amino acids 446-490) of VP16 was fused to the amino terminus of the mouse full-length Oct4 cDNA.

PCR for VP16SO
The cDNA encoding a part of the transactivation domain of VP16 (amino acids 446-490) was amplified with two primer sets, V16F4 (CGAGAATTCGCCATGTTGGGGGACGGGGATTC; SEQ ID NO: 28) and V16OR (CAGGTGTCCAGCCATCCCACCGTACTCGTC; SEQ ID NO:29). Full length Oct4 cDNA was amplified with two primer sets, VP16OF (GACGAGTACGGTGGGATGGCTGGACACCTG; SEQ ID NO: 30) and Oct4R1 (GCGCTCGAGTCTCAGTTTGAATGCATGGGAGAG; SEQ ID NO:31). The two PCR products of each first PCR were used as a template for the secondary PCR with the primer set V16F4 and Oct4R1. VP16OS was directly subcloned into EcoRI and XhoI site of pMXs-IP.

PCR Primers for VP16SO (SEQ ID NO: 32)
V16F4: CGAGAATTCGCCATGTTGGGGGACGGGGATTC (SEQ ID NO: 33)
V16OR: CAGGTGTCCAGCCATCCCACCGTACTCGTC (SEQ ID NO: 34)
VP16OF: GACGAGTACGGTGGGATGGCTGGACACCTG (SEQ ID NO: 35)
Oct4R1: GCGCTCGAGTCTCAGTTTGAATGCATGGGAGAG PCR Parameters

| Denature | 94° C. | 2 min |
| Denature | 94° C. | 15 sec* |
| Anneal | 57° C. | 30 sec* |
| Extend | 68° C. | 1 min* |
| Final extension | 68° C. | 7 min |

*Repeat 25 cycles

VP16SO DNA Sequence (SEQ ID NO: 36)

```
atgttgggggacggggattccccgggtccggatttaccccccacgactccgcccctacggcgctctggatatg
gccgacttcgagtttgagcagatgtttaccgatgccettggaattgacgagtacggtgggatggctggacacctg
gcttcagacttcgccttctcaccceccaccaggtggggtgatgggtcagcagggctggagccgggctgggtggat
cctcgaacctggctaagcttccaagggcctccaggtgggcctggaatcggaccaggctcagaggtattggggatc
tccccatgtccgcccgcatacgagttctgcggagggatggcatactgtggacctcaggttggactgggcctagtc
ccccaagttggcgtggagactttgcagcctgagggccaggcaggagcacgagtggaaagcaactcagagggaacc
tcctctgagccctgtgccgaccgccccaatgccgtgaagttggagaaggtggaaccaactcccgaggagtcccag
gacatgaaagccctgcagaaggagctagaacagtttgccaagctgctgaagcagaagaggatcaccttggggtac
acccaggccgacgtggggctcaccctgggcgttctctttggaaaggtgttcagccagaccaccatctgtcgcttc
gaggccttgcagctcagccttaagaacatgtgtaagctgcggccctgctggagaagtgggtggaggaagccgac
aacaatgagaaccttcaggagatatgcaaatcggagaccctggtgcaggcccggaagagaaagcgaactagcatt
gagaaccgtgtgaggtggagtctggagaccatgtttctgaagtgcccgaagccctcctacagcagatcactcac
atcgccaatcagcttgggctagagaaggatgtggttcgagtatggttctgtaaccggcgccagaagggcaaaaga
tcaagtattgagtattcccaacgagaagagtatgaggctacagggacacctttcccagggggggctgtatcctttt
cctctgcccccaggtccccactttggcaccccaggctatggaagcccccacttcaccacactctactcagtccct
tttcctgagggcgaggcctttccctctgttcccgtcactgctctgggctctcccatgcattcaaactga
```

Accession Number for VP16
Human herpesvirus 1 complete genome: X14112.1
Tegument protein VP16 from human herpes simplex virus type 1: NP_044650
The combination of VP16SO and SKM induced mouse iPSCs at a frequency of around 1%.

Example 2

MEFs transduced with M₃O-SKM were seeded onto feeder cells at the density of 2000 cells/well of a 12-well plate. This cell density is around 15-fold lower than the density used in protocol described above. In addition, 10% fetal bovine serum was replaced with 15% KnockOut Serum Replacement (KSR, Invitrogen) in the culture medium. Combination of the decreased cell density and KSR increased the efficiency of making iPSCs to around 27% by day 12. In contrast, the efficiency with OSKM was around 1% under the same condition.

The herpes simplex virus type 1 protein VP16 is a powerful transactivator. To test if the VP16 TAD could also raise the efficiency of making iPSCs, two fusion genes were prepared between mouse Oct4 and the VP16 TAD. The first fusion gene called VP16LO is composed of the full-length VP16 TAD (amino acids 411-490) fused to the amino terminus of Oct4. The second fusion gene called VP16SO comprises the second half of the VP16 TAD (amino acids 446-490) fused to the amino terminus of Oct4. The efficiency of making mouse iPSCs was around 5% with VP16LO-SKM and around 14% with VP16SO-SKM on day 12 under the above-mentioned culture conditions (with decreased cell density and KSR). The efficiency with these two combinations was higher than the efficiency with OSKM.

BIBLIOGRAPHY

1. Chew, J. L. et al. *Mol Cell Biol* 25, 6031-46 (2005).
2. Nakagawa, M. et al. *Nat Biotechnol* 26, 101-6 (2008).
3. Wernig, M., Meissner, A., Cassady, J. P. & Jaenisch, R. *Cell Stem Cell* 2, 10-2 (2008).
4. Kitamura, T. et al. *Exp Hematol* 31, 1007-14 (2003).
5. Carey, B. W. et al. *Proc Natl Acad Sci USA* 106, 157-62 (2009).
6. Morita, S., Kojima, T. & Kitamura, T. *Gene Ther* 7, 1063-6 (2000).
7. Lengner, C. J. et al. *Cell Stem Cell* 1, 403-15 (2007).
8. Takahashi, K. & Yamanaka, *Cell* 126, 663-76 (2006).
9. Gerber, A. N et al. *Genes Dev* 11, 436-50 (1997).
10. Huangfu, D. et al. *Nat Biotechnol* 26, 795-7 (2008).
11. Weintraub, H. et al. *Genes Dev* 5, 1377-86 (1991).
12. Niwa, H. et al. *Cell* 123, 917-29 (2005).
13. Boxus, M. et al. *Retrovirology* 5, 76 (2008).
14. Romani, B., Engelbrecht, S. & Glashoff, R. H. *J Gen Virol* 91, 1-12 (2010).
15. Pumfery, A. et al. *Curr HIV Res* 1, 343-62 (2003).
16. Cirillo, L. A. et al. *Mol Cell* 9, 279-89 (2002).
17. Ieda, M. et al. *Cell* 142, 375-386 (2010).
18. Hanna, J. et al. *Nature* 462, 595-601 (2009).
19. Stadtfeld, M. et al. *Cell Stem Cell* 2, 230-40 (2008).
20. Gonzalez, F. et al. *Proc Natl Acad Sci USA* 106, 8918-22 (2009).
21. Maherali, N. et al. *Cell Stem Cell* 1, 55-70 (2007).
22. Okita, K., Ichisaka, T. & Yamanaka, S. *Nature* 448, 313-7 (2007).
23. Carey, M. F., Peterson, C. L. & Smale, S. T. In vivo analysis of an endogenous control region. in *Transcriptional regulation in eukaryotes* (eds. Carey, M. F., Peterson, C. L. & Smale, S. T.) 261-322 (Cold Spring Harbor Laboratory Press, 2009).
24. Ding, L. et al. *Cell Stem Cell* 4, 403-15 (2009).
25. Ponnusamy, M. P. et al. *Stem Cells* 27, 3001-11 (2009).
26. Gerber, M. & Shilatifard, *J Biol Chem* 278, 26303-6 (2003).

27. Kouzarides, T. *Cell* 128, 693-705 (2007).
28. Knoepfler, P. S. *Cell Stem Cell* 2, 18-21 (2008).
29. Knoepfler, P. S. et al. *EMBO J* 25, 2723-34 (2006).
33. Zhou, Q. et al. *Nature* 455, 627-32 (2008).
34. Vierbuchen, T. et al. *Nature* 463, 1035-41 (2010).
35. Yamanaka, S. & Blau, H. M. *Nature* 465, 704-12 (2010).
36. Horb, M. E., Shen, C. N., Tosh, D. & Slack, J. M. *Curr Biol* 13, 105-15 (2003).
37. Kaneto, H. et al. *Diabetes* 54, 1009-22 (2005).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method to increase efficiency of reprogramming cells to form induced pluripotent stem cells (iPSC) comprising a) introducing i) a nucleic acid encoding a fusion protein comprising a transactivation domain from MyoD fused to the N-terminus or C-terminus of Oct4 operably linked to a promoter, and ii) at least one nucleic acid encoding Sox2, Klf4, and optionally c-Myc operably linked to a promoter into a somatic cell, wherein the somatic cell expresses the nucleic acids of i) and ii); and
  b) culturing said somatic cell for a time to reprogram into a pluripotent stein cell, wherein the fusion protein increases the efficiency of reprogramming the somatic cell into a iPSC.

2. The method of claim 1, wherein the transactivation domain of MyoD comprises an N terminus region of MyoD.

3. The method of claim 1, wherein the nucleic acid encoding the fusion protein comprises the sequence set forth in SEQ ID NO: 20 or a sequence that is at least 95% identical thereto.

4. The method of claim 1, wherein the cell is mammalian.

5. The method of claim 4, wherein the mammalian cell is human.

6. The method of claim 1, wherein the somatic cells are placed in cell culture medium comprising a serum replacement.

7. An in vivo method comprising: (a) isolating a somatic cell from a subject; (b) reprogramming said somatic cell by the method of claim 1 to produce an iPSC; (c) differentiating the iPSC ex vivo into a differentiated cell; and (d) administering the differentiated cell to the subject.

8. The method of claim 7, wherein the subject is a mammal.

9. The method of claim 1, wherein the presence of the transactivation domain of MyoD increases the efficiency of iPSC production by greater than 40 fold as compared to when the transactivation domain of MyoD is absent.

10. The method of claim 1, wherein the presence of the transactivation domain of MyoD increases the efficiency of iPSC production by greater than 50 fold as compared to when the transactivation domain of MyoD is absent.

11. The method of claim 1, wherein the presence of the transactivation domain of MyoD increases the efficiency of iPSC production by greater than 100 fold as compared to when the transactivation domain of MyoD is absent.

12. A method to accelerate reprogramming cells to form iPSC comprising: a) introducing i) a nucleic acid encoding a fusion protein comprising a transactivation domain of MyoD fused to the N-terminus or C-terminus of Oct4 operably linked to a promoter, and ii) at least one nucleic acid encoding Sox2, Klf4, and optionally c-Myc operably linked to a promoter into a somatic cell, wherein the somatic cell expresses the nucleic acids of i) and ii); and b) culture said somatic cell for a time to reprogram into a pluripotent stem cell, where the fusion protein accelerates the reprogramming of the somatic cell into an iPSC.

13. The method of claim 11, wherein the iPSC is present by day 5 of culturing.

14. The method of claim 11, wherein the iPSC is present by day 7 of culturing.

* * * * *